United States Patent
Hanke et al.

(10) Patent No.: US 7,981,430 B2
(45) Date of Patent: Jul. 19, 2011

(54) MULTI-CLADE CHIMERIC IMMUNOGENS DERIVED FROM HIGHLY CONSERVED REGIONS OF THE HUMAN IMMUNODEFICIENCY VIRUS TYPE 1 (HIV-1) CONSENSUS PROTEOME

(75) Inventors: Tomas Hanke, The John Radcliffe (GB); Andrew James McMichael, The John Radcliffe (GB)

(73) Assignee: Medical Research Council, London (GB)

( * ) Notice: Subject to any disclaimer, the term of this patent is extended or adjusted under 35 U.S.C. 154(b) by 238 days.

(21) Appl. No.: 11/844,301

(22) Filed: Aug. 23, 2007

(65) Prior Publication Data

US 2008/0089901 A1 Apr. 17, 2008

Related U.S. Application Data

(63) Continuation-in-part of application No. PCT/IB2006/001909, filed on Feb. 23, 2006.

(60) Provisional application No. 60/655,764, filed on Feb. 24, 2005.

(51) Int. Cl.
*A61K 39/21* (2006.01)
*A61K 39/295* (2006.01)

(52) U.S. Cl. ................ 424/208.1; 424/188.1; 424/202.1

(58) Field of Classification Search .................. None
See application file for complete search history.

(56) References Cited

FOREIGN PATENT DOCUMENTS

| WO | WO 01/47955 | * | 7/2001 |
| WO | WO 01/91536 | | 12/2001 |

OTHER PUBLICATIONS

Woodberry, T., et al., 1999, Immunogenicity of a Human Immunodeficiency Virus (HIV) Polytope Vaccine Containing Multiple HLA A2 HIV CD8+ Cytotoxic T-Cell Epitopes, J. Virol. 73(7):5320-5325.*

Ayyavoo, V., et al., 2000, Immunogenicity of a Novel DNA Vaccine Cassette Expressing Multiple Human Immunodeficiency Virus (HIV-1) Accessory Genes, AIDS 14(1):1-9.*

Woodberry T et al: "Immunogenicity of a human immunodeficiency virus (HIV) polytope vacine containing multiple HLA A2 HIV CD8+ cytotoxic T-cell epitopes" Journal of Virology, The American Society for Microbiology, US, vol. 73, No. 7, Jul. 1999, pp. 5320-5325.

Kang C Yong et al: "Development of HIV/AIDS Vaccine Using Chimeric GAG-ENV Virus-Like Particles" Biological Chemistry, vol. 380, No. 3, Mar. 1999, pp. 353-364.

(Continued)

*Primary Examiner* — Jeffrey Parkin
(74) *Attorney, Agent, or Firm* — Vedder Price P.C.; Thomas J. Kowalski; Deborah L. Lu

(57) ABSTRACT

The present invention provides artificial fusion proteins (AFPs) designed to elicit an anti-HIV immune response, as well as nucleic acid molecules and expression vectors encoding those proteins. The AFPs of the invention may comprise domains from various HIV proteins, such as Gag, Pol, Vif, and Env proteins, which are partial sequences. HIVCON is an AFP in which the HIV domains are from several HIV clade consensus sequences and which optionally contains additional domains which may be useful, for example, in monitoring expression levels or laboratory animal immune responses. Other aspects of the invention may include compositions and methods for inducing an anti-HIV immune response in a subject, preferably with a DNA prime-MVA boost strategy, and to induce a cell-mediated immune response.

2 Claims, 13 Drawing Sheets

| Ga | Ga | Ga | Po | Po | Vi | Po | Po | En | Po | Po | Po | Po | En |
| C | D | A | B | C | D | A | B | C | D | A | B | C | D |

☐ Mamu epitope  ▨ H-2 epitope  ■ mAb epitope

OTHER PUBLICATIONS

Kong Wing-Pui et al: "Immunogenicity of multiple gene and clade human immunodeficiency virus type 1 DNA vaccines" Journal of Virology, The American Society for Microbiology, US, vol. 77, No. 23, Dec. 2003, pp. 12764-12772.

G. Ferrari, et al., Identification Of Highly Conserved And Broadly . . . ; AIDS Research And Human Retroviruses (2000) vol. 16, No. 14, p. 1433-1443.

A. J. McMichael, et al., HIV Vaccines 1983-2003, Nature Medicine (2003) vol. 9, No. 7, p. 874-880.

J.P. Nkolola, et al., Engineering RENTA, a DNA prime-MVA Boost, Gene Therapy (2004) vol. 11, p. 1068-1080.

Cara C. Wilson, et al., Development Of a DNA Vaccine Designed . . . , Journal of Immunology (2003) vol. 171, p. 5611-5623.

Sven Letourneau, et al., Design and Pre-Clinical Evaluation Of a Universal . . . , PLoS One (Oct. 2007) Issue 10, e984, p. 1-11.

\* cited by examiner

SEQ ID NO:1

```
atggaggaga aggccttcag ccctgaggtg atccccatgt tcaccgccct gtccgagggc  60
gccacccccc aggacctgaa caccatgctg aacaccgtgg gcggccacca ggccgccatg 120
cagatgctga aggacaccat caacgaggag gccgccagt gggaccgcat ctacaagcgc 180
tggatcatcc tgggcctgaa caagatcgtg cgcatgtact ccccgtgtc catcctggac 240
atccgccagg gccccaagga gcccttccgc gactacgtgg accgcttcgc ccgcaactgc 300
cgcgccctc gcaagaaggg ctgctggaag tgcggcaagg agggccacca gatgaaggac 360
tgcaccgagc gccaggccaa cttcctgggc aagatctggc cctcccgctg gaagcccaag 420
atgattggcg ggatcggcgg cttcatcaag gtgcgccagt acgaccagat cctgatcgag 480
atctgcggcc acaaggccat cggcaccgtg ctcgtgggcc caccccgt gaacatcatc 540
ggccgcaacc tgctgaccca gatcggctgc accctgaact tccccatctc ccccatcgag 600
accgtgcccg tgaagctgaa gcccggcatg gacggcccca aggtgaagca gtggcccctg 660
accgaggaga agatcaaggc cctggtggag atctgcaccg agatggagaa ggagggcaag 720
atctccaaga tcggccccga gaaccctac aacaccccg tgttcgccat caagaagaag 780
gactccacca gtggcgcaa actggtggac ttccgcgagc tgaacaagcg cacccaggac 840
ttctgggagg tgcagctggg catccccac cctgccggcc tgaagaagaa gaagtccgtg 900
accgtgctgg acgtgggcga cgcctacttc tccgtgcccc tggacgaggg cttccgcaag 960
tacaccgcct tcaccatccc ctccatcaac aacgagaccc ccggcatccg ctaccagtac 1020
aacgtgctgc ccagggctg aagggctcc ccgccatct tccagtcctc catgaccaag 1080
atcctggagc ccttccgcgc ccagaacccc gagatcgtga tctaccagta catggacgac 1140
ctgtacgtgg gctccgacct ggagatcggc cagcaccgca tggagaaccg ctggcaggtg 1200
atgatcgtgt ggcaggtgga ccgcatgcgc atccgcacct ggaagtccct ggtgaagcac 1260
cacctgaccg aggaggccga gctggagctg gccgagaacc gcgagatcct gaaggacccc 1320
gtgcacggcg tgtactacga ccctccaag gacctgatcg ccgagatcca gtactggcag 1380
gccacctgga tccccgagtg ggagttcgtg aacaccccac cctggtgaa gctgtggtac 1440
cagctggaga agaacgtgac cgagaacttc aacatgtgga gaacgacat ggtggaccag 1500
atgcacgagg acatcatctc cctgtgggac cagtccctga gccctgcgt gaagctgacc 1560
ccctgggtgc ccgcccacaa gggcatcggc ggcaacgagc aggtggacaa gctggtgtcc 1620
cagggcatcc gcaaggtgct gttcctggac ggcatcgaca aggcccaggc caaggagatc 1680
gtggcctcct gcgacaagtg ccagctgaag ggcgaggcca tgcacggcca ggtggactgc 1740
tcccccggca tctggcagct ggactgcacc cacctggagg caaggtgat cctggtggcc 1800
gtgcacgtgg cctccggcta catcgaggcc gaagtgattc ccgccgagac cggccaggag 1860
accgcctact tcctgctgaa gctggccatg aacaaggagc tgaagaagat catcggccag 1920
gtgcgcgacc aggccgagca cctgaagacc gccgtgcaga tggccgtgtt catccacaac 1980
ttcaagcgca agggcggaat cggcggctac tccgccggcg agcgcatctg gaagggcccc 2040
gccaagctgc tgtggaaggg cgagggcgcc gtggtgatcc aggacaactc cgacatcaag 2100
gtggtgcccc ccgcaaggc caagatcatc cgcgactacg caagcagat ggccggtgcc 2160
gactgcgtgt cctgggcgc tgccggctcc accatgggcg ccgcctccat gacactgacc 2220
gtgcaggccc gccagctgct gtccggcatc gtgcagcagc agaacaacct gctgcgcgcc 2280
atcgaggccc agcagcacct gctgcagctg accgtgtggg gcatcaagca gtag       2334
```

FIG. 2

SEQ ID NO:2

MEEKAFSPEVIPMFTALSEGATPQDLNTMLNTVGGHQAAMQMLKDTINEE
AAEWDRIYKRWIILGLNKIVRMYSPVSILDIRQGPKEPFRDYVDRFARNC
RAPRKKGCWKCGKEGHQMKDCTERQANFLGKIWPSRWKPKMIGGIGGFIK
VRQYDQILIEICGHKAIGTVLVGPTPVNIIGRNLLTQIGCTLNFPISPIE
TVPVKLKPGMDGPKVKQWPLTEEKIKALVEICTEMEKEGKISKIGPENPY
NTPVFAIKKKDSTKWRKLVDFRELNKRTQDFWEVQLGIPHPAGLKKKKSV
TVLDVGDAYFSVPLDEGFRKYTAFTIPSINNETPGIRYQYNVLPQGWKGS
PAIFQSSMTKILEPFRAQNPEIVIYQYMDDLYVGSDLEIGQHRMENRWQV
MIVWQVDRMRIRTWKSLVKHHLTEEAELELAENREILKDPVHGVYYDPSK
DLIAEIQYWQATWIPEWEFVNTPPLVKLWYQLEKNVTENFNMWKNDMVDQ
MHEDIISLWDQSLKPCVKLTPWVPAHKGIGGNEQVDKLVSQGIRKVLFLD
GIDKAQAKEIVASCDKCQLKGEAMHGQVDCSPGIWQLDCTHLEGKVILVA
VHVASGYIEAEVIPAETGQETAYFLLKLAMNKELKKIIGQVRDQAEHLKT
AVQMAVFIHNFKRKGGIGGYSAGERIWKGPAKLLWKGEGAVVIQDNSDIK
VVPRRKAKIIRDYGKQMAGADCVFLGAAGSTMGAASMTLTVQARQLLSGI
VQQQNNLLRAIEAQQHLLQLTVWGIKQ

FIG. 3

SEQ ID NO:3

```
atggaggaga aggccttcag ccctgaggtg atccccatgt tcaccgccct gtccgagggc   60
gccaccccc aggacctgaa caccatgctg aacaccgtgg gcggccacca ggccgccatg  120
cagatgctga aggacaccat caacgaggag gccgccagt gggaccgcat ctacaagcgc  180
tggatcatcc tgggcctgaa caagatcgtg cgcatgtact ccccgtgtc catcctggac  240
atccgccagg gccccaagga gcccttccgc gactacgtg accgcttcgc ccgcaactgc  300
cgcgccctc gcaagaaggg ctgctggaag tgcggcaagg agggccacca gatgaaggac  360
tgcaccgagc gccaggccaa cttcctgggc aagatctggc cctcccgctg gaagcccaag  420
atgattggcg ggatcggcgg cttcatcaag gtgcgccagt acgaccagat cctgatcgag  480
atctgcggcc acaaggccat cggcaccgtg ctcgtgggcc ccacccccgt gaacatcatc  540
ggccgcaacc tgctgaccca gatcggctgc accctgaact tccccatctc ccccatcgag  600
accgtgcccg tgaagctgaa gccggcatg acggcccca aggtgaagca gtggcccctg  660
accgaggaga agatcaaggc cctggtggag atctgcaccg agatggagaa ggagggcaag  720
atctccaaga tcggccccga gaaccctac aacacccccg tgttcgccat caagaagaag  780
gactccacca agtggcgcaa actggtggac ttccgcgagc tgaacaagcg cacccaggac  840
ttctgggagg tgcagctggg catcccccac cctgccggcc tgaagaagaa gaagtccgtg  900
accgtgctgg acgtgggcga cgcctacttc tccgtgccc tggacgaggg cttccgcaag  960
tacaccgcct tcaccatccc ctccatcaac aacgagaccc ccggcatccg ctaccagtac 1020
aacgtgctgc ccaggctg gaagggctcc cccgccatct tccagtcctc catgaccaag 1080
atcctggagc ccttccgcgc ccagaacccc gagatcgtga tctaccagta catggacgac 1140
ctgtacgtgg gctccgacct ggagatcggc cagcaccgca tggagaaccg ctggcaggtg 1200
atgatcgtgt ggcaggtgga ccgcatgcgc atccgcacct ggaagtccct ggtgaagcac 1260
cacctgaccg aggaggccga gctggagctg gccgagaacc gcgagatcct gaaggacccc 1320
gtgcacggcg tgtactacga cccctccaag gacctgatcg ccgagatcca gtactggcag 1380
gccacctgga tccccgagtg ggagttcgtg aacacccca ccctggtgaa gctgtggtac 1440
cagctggaga agaacgtgac cgagaacttc aacatgtgga agaacgacat ggtggaccag 1500
atgcacgagg acatcatctc cctgtgggac cagtccctga gccctgcgt gaagctgacc 1560
ccctgggtgc ccgcccacaa gggcatcggc ggcaacgagc aggtggacaa gctggtgtcc 1620
cagggcatcc gcaaggtgct gttcctggac ggcatcgaca aggcccaggc caaggagatc 1680
gtggcctcct gcgacaagtg ccagctgaag ggcgaggcca tgcacggcca ggtggactgc 1740
tcccccggca tctggcagct ggactgcacc cacctggagg gcaaggtgat cctggtggcc 1800
gtgcacgtgg cctccggcta catcgaggcc gaagtgattc ccgccgagac cggccaggag 1860
accgcctact tcctgctgaa gctggccatg aacaaggagc tgaagaagat catcggccag 1920
gtgcgcgacc aggccgagca cctgaagacc gccgtgcaga tggccgtgtt catccacaac 1980
ttcaagcgca agggcggaat cggcggctac tccgccggcg agcgcatctg gaagggcccc 2040
gccaagctgc tgtggaaggg cgagggcgcc gtggtgatcc aggacaactc cgacatcaag 2100
gtggtgcccc gccgcaaggc caagatcatc cgcgactacg caagcagat ggccggtgcc 2160
gactgcgtgt tcctgggcgc tgccggctcc accatgggcg ccgcctccat gaccctgacc 2220
gtgcaggccc gccagctgct gtccggcatc gtgcagcagc agaacaacct gctgcgcgcc 2280
atcgaggccc agcagcacct gctgcagctg accgtgtggg catcaagca ggcctgcacc 2340
ccctacgaca tcaaccagat gctgagaggc cccggtcgcg ccttcgtgac catcccaac 2400
cccctgctgg gcctggacta g                                         2421
```

FIG. 4

SEQ ID NO:4

MEEKAFSPEVIPMFTALSEGATPQDLNTMLNTVGGHQAAMQMLKDTINEE
AAEWDRIYKRWIILGLNKIVRMYSPVSILDIRQGPKEPFRDYVDRFARNC
RAPRKKGCWKCGKEGHQMKDCTERQANFLGKIWPSRWKPKMIGGIGGFIK
VRQYDQILIEICGHKAIGTVLVGPTPVNIIGRNLLTQIGCTLNFPISPIE
TVPVKLKPGMDGPKVKQWPLTEEKIKALVEICTEMEKEGKISKIGPENPY
NTPVFAIKKKDSTKWRKLVDFRELNKRTQDFWEVQLGIPHPAGLKKKKSV
TVLDVGDAYFSVPLDEGFRKYTAFTIPSINNETPGIRYQYNVLPQGWKGS
PAIFQSSMTKILEPFRAQNPEIVIYQYMDDLYVGSDLEIGQHRMENRWQV
MIVWQVDRMRIRTWKSLVKHHLTEEAELELAENREILKDPVHGVYYDPSK
DLIAEIQYWQATWIPEWEFVNTPPLVKLWYQLEKNVTENFNMWKNDMVDQ
MHEDIISLWDQSLKPCVKLTPWVPAHKGIGGNEQVDKLVSQGIRKVLFLD
GIDKAQAKEIVASCDKCQLKGEAMHGQVDCSPGIWQLDCTHLEGKVILVA
VHVASGYIEAEVIPAETGQETAYFLLKLAMNKELKKIIGQVRDQAEHLKT
AVQMAVFIHNFKRKGGIGGYSAGERIWKGPAKLLWKGEGAVVIQDNSDIK
VVPRRKAKIIRDYGKQMAGADCVFLGAAGSTMGAASMTLTVQARQLLSGI
VQQQNNLLRAIEAQQHLLQLTVWGIKQACTPYDINQMLRGPGRAFVTIPN
PLLGLD*

FIG. 5

SEQ ID NO:5

```
ccgattaagc ttcccgggcc cgccgccacc atggaggaga aggccttctc ccccgaggtg 60
atccccatgt tcaccgccct gtccgagggc gccaccccc aggacctgaa caccatgctg 120
aacaccgtgg gcggccacca ggccgccatg cagatgctga aggacaccat caacgaggag 180
gccgccgagt gggaccgcat ctacaagcgc tggatcatcc tgggcctgaa caagatcgtg 240
cgcatgtact ccccgtgtc catcctggac atcgccagg gccccaagga gcccttccgc 300
gactacgtgg accgcttcgc ccgcaactgc cgcgcccccc gcaagaaggg ctgctggaag 360
tgcggcaagg agggccacca gatgaaggac tgcaccgagc gccaggccaa cttcctgggc 420
aagatctggc cctcccgctg gaagcccaag atgatcggcg catcggcgg cttcatcaag 480
gtgcgccagt acgaccagat cctgatcgag atctgcggcc acaaggccat cggcaccgtg 540
ctggtgggcc ccaccccgt gaacatcatc ggccgcaacc tgctgaccca gatcggctgc 600
accctgaact tccccatctc ccccatcgag accgtgcccg tgaagctgaa gcccggcatg 660
gacggcccca aggtgaagca gtggcccctg accgaggaga agatcaaggc cctggtggag 720
atctgcaccg agatggagaa ggagggcaag atctccaaga tcggccccga gaacccctac 780
aacaccccg tgttcgccat caagaagaag gactccacca gtggcgcaa gctggtggac 840
ttccgcgagc tgaacaagcg cacccaggac ttctgggagg tgcagctggg catcccccac 900
cccgccggcc tgaagaagaa gaagtccgtg accgtgctgg acgtgggcga cgcctacttc 960
tccgtgcccc tggacgaggg cttccgcaag tacaccgcct tcaccatccc ctccatcaac 1020
aacgagaccc ccggcatccg ctaccagtac aacgtgctgc cccagggctg gaagggctcc 1080
cccgccatct tccagtcctc catgaccaag atcctggagc ccttccgcgc ccagaacccc 1140
gagatcgtga tctaccagta catggacgac ctgtacgtgg gctccgacct ggagatcggc 1200
cagcaccgca tggagaaccg ctggcaggtg atgatcgtgt ggcaggtgga ccgcatgcgc 1260
atccgcacct ggaagtccct ggtgaagcac cacctgaccg aggaggccga gctggagctg 1320
gccgagaacc gcgagatcct gaaggacccc gtgcacggcg tgtactacga ccccctccaag 1380
gacctgatcg ccgagatcca gtactggcag gccacctgga tccccgagtg ggagttcgtg 1440
aacacccccc ccctggtgaa gctgtggtac cagctggaga agaacgtgac cgagaacttc 1500
aacatgtgga gaacgacat ggtggaccag atgcacgagg acatcatctc cctgtgggac 1560
cagtccctga gccctgcgt gaagctgacc cctgggtgc ccgcccacaa gggcatcggc 1620
ggcaacgagc aggtggacaa gctggtgtcc cagggcatcc gcaaggtgct gttcctggac 1680
ggcatcgaca aggcccaggc caaggagatc gtggcctcct gcgacaagtg ccagctgaag 1740
ggcgaggcca tgcacggcca ggtggactgc tccccggca tctggcagct ggactgcacc 1800
cacctggagg caaggtgat cctggtggcc gtgcacgtgg cctccggcta tcgaggcc 1860
gaggtgatcc ccgccgagac cggccaggag accgcctact tcctgctgaa gctggccatg 1920
aacaaggagc tgaagaagat catcggccag gtgcgcgacc aggccagca cctgaagacc 1980
gccgtgcaga tggccgtgtt catccacaac ttcaagcgca gggcggcat cggcggctac 2040
tccgccggcg aggcgatctg gaagggcccc gccaagctgc tgtggaaggg cgagggcgcc 2100
gtggtgatcc aggacaactc cgacatcaag gtggtgcccc gcgcaaggc caagatcatc 2160
cgcgactacg caagcagat ggccggcgcc gactgcgtgt cctgggcgc cgccggctcc 2220
accatgggcg ccgcctccat gaccctgacc gtgcaggccc gcagctgct gtccggcatc 2280
gtgcagcagc agaacaacct gctgcgcgcc atcgaggccc agcagcacct gctgcagctg 2340
accgtgtggg gcatcaagca gtagcccggg tctagaggac ga                     2382
```

FIG. 6

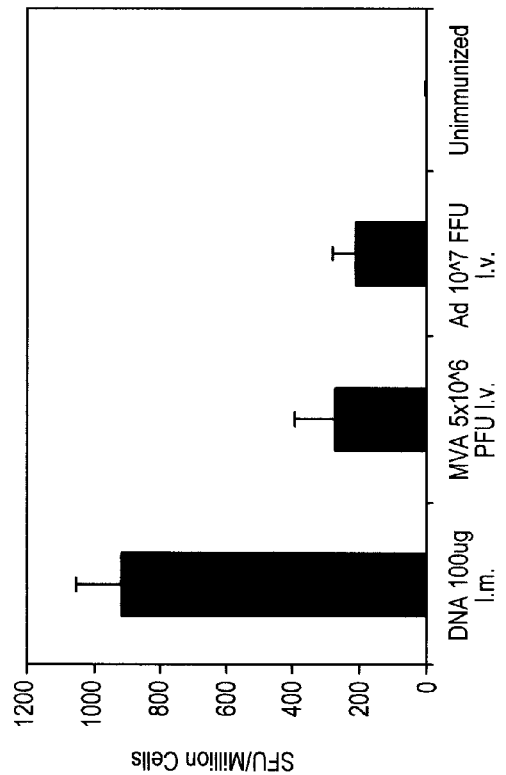
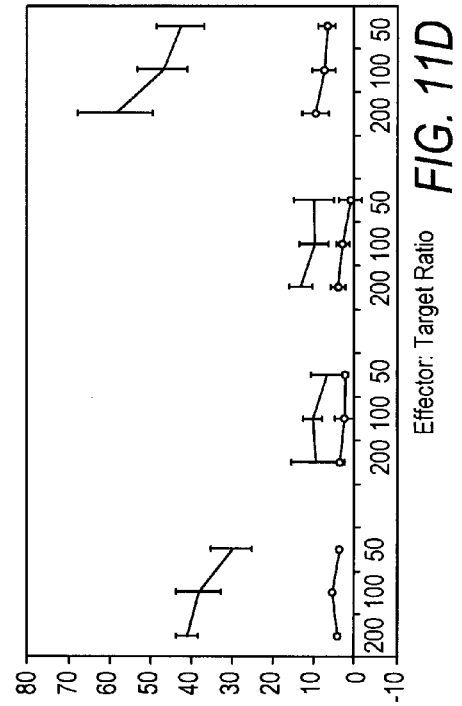
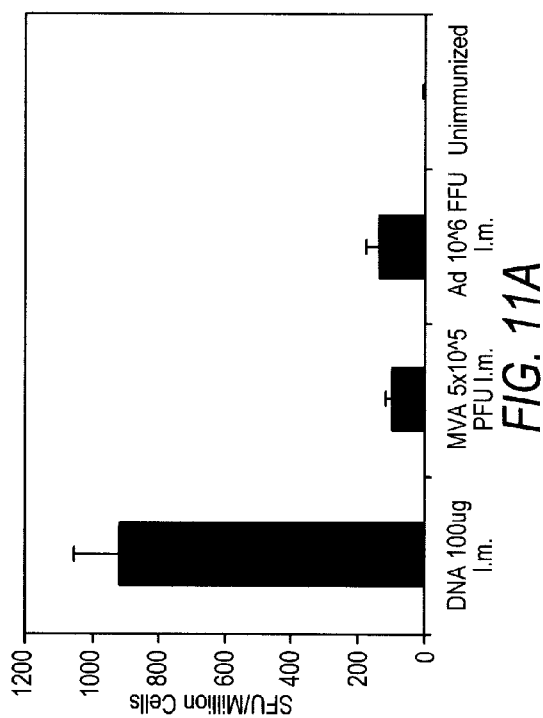
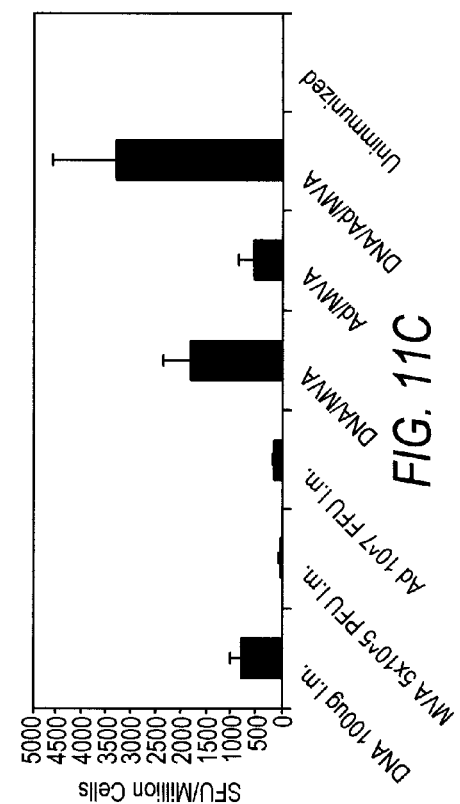

SEQUENCE LISTING

<160> NUMBER OF SEQ ID NOS: 16

<210> SEQ ID NO 1
<211> LENGTH: 2334
<212> TYPE: DNA
<213> ORGANISM: Artificial Sequence
<220> FEATURE:
<223> OTHER INFORMATION: Description of Artificial Sequence: Synthetic
      HIV construct

<400> SEQUENCE: 1

```
atggaggaga aggccttcag ccctgaggtg atccccatgt tcaccgccct gtccgagggc      60
gccacccccc aggacctgaa caccatgctg aacaccgtgg gcggccacca ggccgccatg     120
cagatgctga aggacaccat caacgaggag gccgccgagt gggaccgcat ctacaagcgc     180
tggatcatcc tgggcctgaa caagatcgtg cgcatgtact ccccgtgtc catcctggac      240 atcgccagg gccccaagga gcccttccgc gactacgtgg accgcttcgc ccgcaactgc     300
cgcgcccctc gcaagaaggg ctgctggaag tgcggcaagg agggccacca gatgaaggac     360
tgcaccgagc gccaggccaa cttcctgggc aagatctggc cctcccgctg gaagcccaag     420
atgattggcg ggatcggcgg cttcatcaag gtgcgccagt acgaccagat cctgatcgag     480
atctgcggcc acaaggccat cggcaccgtg ctcgtgggcc ccaccccgt gaacatcatc      540 ggccgcaacc tgctgaccca gatcggctgc accctgaact tccccatctc ccccatcgag     600
accgtgcccg tgaagctgaa gccggcatg gacgccccca aggtgaagca gtggcccctg      660
accgaggaga agatcaaggc cctggtggag atctgcaccg agatggagaa ggagggcaag     720
atctccaaga tcggccccga gaaccctac aacacccccg tgttcgccat caagaagaag      780
gactccacca gtggcgcaa actggtggac ttccgcgagc tgaacaagcg cacccaggac      840
ttctggggag tgcagctggg catcccccac cctgccggcc tgaagaagaa gaagtccgtg     900
accgtgctgg acgtgggcga cgcctacttc tccgtgcccc tggacgaggg cttccgcaag     960
tacaccgcct tcaccatccc ctccatcaac aacgagaccc ccggcatccg ctaccagtac    1020
aacgtgctgc cccagggctg gaagggctcc cccgccatct tccagtcctc catgaccaag    1080
atcctggagc ccttccgcgc ccagaacccc gagatcgtga tctaccagta catggacgac    1140
ctgtacgtgg gctccgacct ggagatcggc cagcaccgca tggagaaccg ctggcaggtg    1200
atgatcgtgt ggcaggtgga ccgcatgcgc atccgcacct ggaagtccct ggtgaagcac    1260
cacctgaccg aggaggccga gctggagctg gccgagaacc gcgagatcct gaaggacccc    1320
gtgcacggcg tgtactacga cccctccaag gacctgatcg ccgagatcca gtactggcag    1380
gccacctgga tccccgagtg ggagttcgtg aacaccccac ccctggtgaa gctgtggtac    1440
cagctggaga gaacgtgac cgagaacttc aacatgtgga gaacgacat ggtggaccag     1500 atgcacgagg acatcatctc cctgtgggac cagtccctga gccctgcgt gaagctgacc    1560 ccctgggtgc ccgcccacaa gggcatcggc ggcaacgagc aggtggacaa gctggtgtcc    1620
```

-continued

```
cagggcatcc gcaaggtgct gttcctggac ggcatcgaca aggcccaggc caaggagatc    1680
gtggcctcct gcgacaagtg ccagctgaag ggcgaggcca tgcacggcca ggtggactgc    1740
tcccccggca tctggcagct ggactgcacc cacctggagg gcaaggtgat cctggtggcc    1800
gtgcacgtgg cctccggcta catcgaggcc gaagtgattc cgccgagac cggccaggag     1860 accgcctact tcctgctgaa gctggccatg aacaaggagc tgaagaagat catcggccag    1920
gtgcgcgacc aggccgagca cctgaagacc gccgtgcaga tggccgtgtt catccacaac    1980
ttcaagcgca agggcggaat cggcggctac tccgccggcg agcgcatctg aagggcccc     2040 gccaagctgc tgtggaaggg cgagggcgcc gtggtgatcc aggacaactc cgacatcaag    2100
gtggtgcccc gccgcaaggc caagatcatc cgcgactacg caagcagat ggccggtgcc     2160 gactgcgtgt cctgggcgc tgccggctcc accatgggcg ccgcctccat gaccctgacc     2220
gtgcaggccc gccagctgct gtccggcatc gtgcagcagc agaacaacct gctgcgcgcc    2280
atcgaggccc agcagcacct gctgcagctg accgtgtggg gcatcaagca gtag          2334
```

<210> SEQ ID NO 2
<211> LENGTH: 777
<212> TYPE: PRT
<213> ORGANISM: Artificial Sequence
<220> FEATURE:
<223> OTHER INFORMATION: Description of Artificial Sequence: Synthetic
      HIV construct

<400> SEQUENCE: 2

```
Met Glu Glu Lys Ala Phe Ser Pro Glu Val Ile Pro Met Phe Thr Ala
1               5                   10                  15

Leu Ser Glu Gly Ala Thr Pro Gln Asp Leu Asn Thr Met Leu Asn Thr
            20                  25                  30

Val Gly Gly His Gln Ala Ala Met Gln Met Leu Lys Asp Thr Ile Asn
        35                  40                  45

Glu Glu Ala Ala Glu Trp Asp Arg Ile Tyr Lys Arg Trp Ile Ile Leu
    50                  55                  60

Gly Leu Asn Lys Ile Val Arg Met Tyr Ser Pro Val Ser Ile Leu Asp
65                  70                  75                  80

Ile Arg Gln Gly Pro Lys Glu Pro Phe Arg Asp Tyr Val Asp Arg Phe
                85                  90                  95

Ala Arg Asn Cys Arg Ala Pro Arg Lys Lys Gly Cys Trp Lys Cys Gly
            100                 105                 110

Lys Glu Gly His Gln Met Lys Asp Cys Thr Glu Arg Gln Ala Asn Phe
        115                 120                 125

Leu Gly Lys Ile Trp Pro Ser Arg Trp Lys Pro Lys Met Ile Gly Gly
    130                 135                 140

Ile Gly Gly Phe Ile Lys Val Arg Gln Tyr Asp Gln Ile Leu Ile Glu
145                 150                 155                 160

Ile Cys Gly His Lys Ala Ile Gly Thr Val Leu Val Gly Pro Thr Pro
                165                 170                 175

Val Asn Ile Ile Gly Arg Asn Leu Leu Thr Gln Ile Gly Cys Thr Leu
            180                 185                 190

Asn Phe Pro Ile Ser Pro Ile Glu Thr Val Pro Val Lys Leu Lys Pro
        195                 200                 205

Gly Met Asp Gly Pro Lys Val Lys Gln Trp Pro Leu Thr Glu Glu Lys
    210                 215                 220

Ile Lys Ala Leu Val Glu Ile Cys Thr Glu Met Glu Lys Glu Gly Lys
225                 230                 235                 240
```

```
Ile Ser Lys Ile Gly Pro Glu Asn Pro Tyr Asn Thr Pro Val Phe Ala
            245                 250                 255

Ile Lys Lys Lys Asp Ser Thr Lys Trp Arg Lys Leu Val Asp Phe Arg
        260                 265                 270

Glu Leu Asn Lys Arg Thr Gln Asp Phe Trp Glu Val Gln Leu Gly Ile
    275                 280                 285

Pro His Pro Ala Gly Leu Lys Lys Lys Ser Val Thr Val Leu Asp
290                 295                 300

Val Gly Asp Ala Tyr Phe Ser Val Pro Leu Asp Glu Gly Phe Arg Lys
305                 310                 315                 320

Tyr Thr Ala Phe Thr Ile Pro Ser Ile Asn Asn Glu Thr Pro Gly Ile
                325                 330                 335

Arg Tyr Gln Tyr Asn Val Leu Pro Gln Gly Trp Lys Gly Ser Pro Ala
            340                 345                 350

Ile Phe Gln Ser Ser Met Thr Lys Ile Leu Glu Pro Phe Arg Ala Gln
        355                 360                 365

Asn Pro Glu Ile Val Ile Tyr Gln Tyr Met Asp Asp Leu Tyr Val Gly
    370                 375                 380

Ser Asp Leu Glu Ile Gly Gln His Arg Met Glu Asn Arg Trp Gln Val
385                 390                 395                 400

Met Ile Val Trp Gln Val Asp Arg Met Arg Ile Arg Thr Trp Lys Ser
                405                 410                 415

Leu Val Lys His His Leu Thr Glu Glu Ala Glu Leu Glu Leu Ala Glu
            420                 425                 430

Asn Arg Glu Ile Leu Lys Asp Pro Val His Gly Val Tyr Tyr Asp Pro
        435                 440                 445

Ser Lys Asp Leu Ile Ala Glu Ile Gln Tyr Trp Gln Ala Thr Trp Ile
    450                 455                 460

Pro Glu Trp Glu Phe Val Asn Thr Pro Pro Leu Val Lys Leu Trp Tyr
465                 470                 475                 480

Gln Leu Glu Lys Asn Val Thr Glu Asn Phe Asn Met Trp Lys Asn Asp
                485                 490                 495

Met Val Asp Gln Met His Glu Asp Ile Ile Ser Leu Trp Asp Gln Ser
            500                 505                 510

Leu Lys Pro Cys Val Lys Leu Thr Pro Trp Val Pro Ala His Lys Gly
        515                 520                 525

Ile Gly Gly Asn Glu Gln Val Asp Lys Leu Val Ser Gln Gly Ile Arg
    530                 535                 540

Lys Val Leu Phe Leu Asp Gly Ile Asp Lys Ala Gln Ala Lys Glu Ile
545                 550                 555                 560

Val Ala Ser Cys Asp Lys Cys Gln Leu Lys Gly Glu Ala Met His Gly
                565                 570                 575

Gln Val Asp Cys Ser Pro Gly Ile Trp Gln Leu Asp Cys Thr His Leu
            580                 585                 590

Glu Gly Lys Val Ile Leu Val Ala Val His Val Ala Ser Gly Tyr Ile
        595                 600                 605

Glu Ala Glu Val Ile Pro Ala Glu Thr Gly Gln Glu Thr Ala Tyr Phe
    610                 615                 620

Leu Leu Lys Leu Ala Met Asn Lys Glu Leu Lys Lys Ile Ile Gly Gln
625                 630                 635                 640

Val Arg Asp Gln Ala Glu His Leu Lys Thr Ala Val Gln Met Ala Val
                645                 650                 655

Phe Ile His Asn Phe Lys Arg Lys Gly Gly Ile Gly Gly Tyr Ser Ala
            660                 665                 670
```

```
Gly Glu Arg Ile Trp Lys Gly Pro Ala Lys Leu Leu Trp Lys Gly Glu
            675                 680                 685

Gly Ala Val Val Ile Gln Asp Asn Ser Asp Ile Lys Val Val Pro Arg
        690                 695                 700

Arg Lys Ala Lys Ile Ile Arg Asp Tyr Gly Lys Gln Met Ala Gly Ala
705                 710                 715                 720

Asp Cys Val Phe Leu Gly Ala Ala Gly Ser Thr Met Gly Ala Ala Ser
                725                 730                 735

Met Thr Leu Thr Val Gln Ala Arg Gln Leu Leu Ser Gly Ile Val Gln
            740                 745                 750

Gln Gln Asn Asn Leu Leu Arg Ala Ile Glu Ala Gln Gln His Leu Leu
        755                 760                 765

Gln Leu Thr Val Trp Gly Ile Lys Gln
    770                 775

<210> SEQ ID NO 3
<211> LENGTH: 2421
<212> TYPE: DNA
<213> ORGANISM: Artificial Sequence
<220> FEATURE:
<223> OTHER INFORMATION: Description of Artificial Sequence: Synthetic
      HIV construct

<400> SEQUENCE: 3
atggaggaga aggccttcag ccctgaggtg atccccatgt tcaccgccct gtccgagggc      60
gccacccccc aggacctgaa caccatgctg aacaccgtgg cgggccacca ggccgccatg     120
cagatgctga aggacaccat caacgaggag ccgccgagtg ggaccgcat ctacaagcgc      180 tggatcatcc tgggcctgaa caagatcgtg cgcatgtact cccccgtgtc catcctggac     240
atccgccagg gccccaagga gcccttccgc gactacgtgg accgcttcgc ccgcaactgc     300
cgcgcccctc gcaagaaggg ctgctggaag tgcggcaagg agggccacca gatgaaggac     360
tgcaccgagc gccaggccaa cttcctgggc aagatctggc cctcccgctg gaagcccaag     420
atgattggcg ggatcggcgg cttcatcaag gtgcgccagt acgaccagat cctgatcgag     480
atctgcggcc acaaggccat cggcaccgtg ctcgtgggcc ccacccccgt gaacatcatc     540
ggccgcaacc tgctgaccca gatcggctgc accctgaact tccccatctc ccccatcgag     600
accgtgcccg tgaagctgaa gcccggcatg gacggcccca aggtgaagca gtggcccctg     660
accgaggaga gatcaaggc cctggtggag atctgcaccg atgaggagaa ggagggcaag     720
atctccaaga tcggccccga gaaccctac aacaccccg tgttcgccat caagaagaag     780
gactccacca gtggcgcaa actggtggac ttccgcgagc tgaacaagcg cacccaggac     840 ttctggagg tgcagctggg catccccac cctgccggcc tgaagaagaa gaagtccgtg     900
accgtgctgg acgtgggcga cgcctacttc tccgtgcccc tggacgaggg cttccgcaag     960
tacaccgcct tcaccatccc ctccatcaac aacgagaccc ccggcatccg ctaccagtac    1020
aacgtgctgc cccagggctg gaagggctcc cccgccatct ccagtcctc catgaccaag    1080 atcctggagc ccttccgcgc ccagaacccc gagatcgtga tctaccagta catggacgac    1140
ctgtacgtgg gctccgacct ggagatcggc cagcaccgca tggagaaccg ctggcaggtg    1200
atgatcgtgt ggcaggtgga ccgcatgcgc atccgcacct ggagtccct ggtgaagcac    1260 cacctgaccg aggaggccga gctggagctg gccgagaacc gcgagatcct gaaggacccc    1320
gtgcacggcg tgtactacga ccctccaag gacctgatcg ccgagatcca gtactggcag    1380 gccaccctgga tccccgagtg ggagttcgtg aacacccac ccctggtgaa gctgtggtac    1440
```

-continued

```
cagctggaga agaacgtgac cgagaacttc aacatgtgga agaacgacat ggtggaccag    1500
atgcacgagg acatcatctc cctgtgggac cagtccctga agccctgcgt gaagctgacc    1560
ccctgggtgc cgcccacaa gggcatcggc ggcaacgagc aggtggacaa gctggtgtcc     1620
cagggcatcc gcaaggtgct gttcctggac ggcatcgaca aggcccaggc caaggagatc    1680
gtggcctcct gcgacaagtg ccagctgaag ggcgaggcca tgcacggcca ggtggactgc    1740
tcccccggca tctggcagct ggactgcacc cacctggagg caaggtgat cctggtggcc     1800 gtgcacgtgg cctccggcta catcgaggcc gaagtgattc cgccgagac cggccaggag     1860 accgcctact tcctgctgaa gctggccatg aacaaggagc tgaagaagat catcggccag    1920
gtgcgcgacc aggccgagca cctgaagacc gccgtgcaga tggccgtgtt catccacaac    1980
ttcaagcgca agggcggaat cggcggctac tccgccggcg agcgcatctg gaagggcccc    2040
gccaagctgc tgtggaaggg cgagggcgcc gtggtgatcc aggacaactc cgacatcaag    2100
gtggtgcccc gccgcaaggc caagatcatc cgcgactacg gcaagcagat ggccggtgcc    2160
gactgcgtgt tcctgggcgc tgccggctcc accatgggcg ccgcctccat gaccctgacc    2220
gtgcaggccc gccagctgct gtccggcatc gtgcagcagc agaacaacct gctgcgcgcc    2280
atcgaggccc agcagcacct gctgcagctg accgtgtggg gcatcaagca ggcctgcacc    2340
ccctacgaca tcaaccagat gctgagaggc cccggtcgcg ccttcgtgac catccccaac    2400
cccctgctgg gcctggacta g                                              2421
```

```
<210> SEQ ID NO 4
<211> LENGTH: 806
<212> TYPE: PRT
<213> ORGANISM: Artificial Sequence
<220> FEATURE:
<223> OTHER INFORMATION: Description of Artificial Sequence: Synthetic
      HIV construct

<400> SEQUENCE: 4
```

```
Met Glu Glu Lys Ala Phe Ser Pro Glu Val Ile Pro Met Phe Thr Ala
1               5                   10                  15

Leu Ser Glu Gly Ala Thr Pro Gln Asp Leu Asn Thr Met Leu Asn Thr
            20                  25                  30

Val Gly Gly His Gln Ala Ala Met Gln Met Leu Lys Asp Thr Ile Asn
        35                  40                  45

Glu Glu Ala Ala Glu Trp Asp Arg Ile Tyr Lys Arg Trp Ile Ile Leu
    50                  55                  60

Gly Leu Asn Lys Ile Val Arg Met Tyr Ser Pro Val Ser Ile Leu Asp
65                  70                  75                  80

Ile Arg Gln Gly Pro Lys Glu Pro Phe Arg Asp Tyr Val Asp Arg Phe
                85                  90                  95

Ala Arg Asn Cys Arg Ala Pro Arg Lys Lys Gly Cys Trp Lys Cys Gly
            100                 105                 110

Lys Glu Gly His Gln Met Lys Asp Cys Thr Glu Arg Gln Ala Asn Phe
        115                 120                 125

Leu Gly Lys Ile Trp Pro Ser Arg Trp Lys Pro Lys Met Ile Gly Gly
    130                 135                 140

Ile Gly Gly Phe Ile Lys Val Arg Gln Tyr Asp Gln Ile Leu Ile Glu
145                 150                 155                 160

Ile Cys Gly His Lys Ala Ile Gly Thr Val Leu Val Gly Pro Thr Pro
                165                 170                 175

Val Asn Ile Ile Gly Arg Asn Leu Leu Thr Gln Ile Gly Cys Thr Leu
```

```
                    180                 185                 190
Asn Phe Pro Ile Ser Pro Ile Glu Thr Val Pro Val Lys Leu Lys Pro
                195                 200                 205

Gly Met Asp Gly Pro Lys Val Lys Gln Trp Pro Leu Thr Glu Glu Lys
            210                 215                 220

Ile Lys Ala Leu Val Glu Ile Cys Thr Glu Met Glu Lys Glu Gly Lys
225                 230                 235                 240

Ile Ser Lys Ile Gly Pro Glu Asn Pro Tyr Asn Thr Pro Val Phe Ala
                245                 250                 255

Ile Lys Lys Lys Asp Ser Thr Lys Trp Arg Lys Leu Val Asp Phe Arg
            260                 265                 270

Glu Leu Asn Lys Arg Thr Gln Asp Phe Trp Glu Val Gln Leu Gly Ile
        275                 280                 285

Pro His Pro Ala Gly Leu Lys Lys Lys Ser Val Thr Val Leu Asp
    290                 295                 300

Val Gly Asp Ala Tyr Phe Ser Val Pro Leu Asp Glu Gly Phe Arg Lys
305                 310                 315                 320

Tyr Thr Ala Phe Thr Ile Pro Ser Ile Asn Asn Glu Thr Pro Gly Ile
                325                 330                 335

Arg Tyr Gln Tyr Asn Val Leu Pro Gln Gly Trp Lys Gly Ser Pro Ala
            340                 345                 350

Ile Phe Gln Ser Ser Met Thr Lys Ile Leu Glu Pro Phe Arg Ala Gln
        355                 360                 365

Asn Pro Glu Ile Val Ile Tyr Gln Tyr Met Asp Asp Leu Tyr Val Gly
    370                 375                 380

Ser Asp Leu Glu Ile Gly Gln His Arg Met Glu Asn Arg Trp Gln Val
385                 390                 395                 400

Met Ile Val Trp Gln Val Asp Arg Met Arg Ile Arg Thr Trp Lys Ser
                405                 410                 415

Leu Val Lys His His Leu Thr Glu Glu Ala Leu Glu Leu Ala Glu
            420                 425                 430

Asn Arg Glu Ile Leu Lys Asp Pro Val His Gly Val Tyr Tyr Asp Pro
        435                 440                 445

Ser Lys Asp Leu Ile Ala Glu Ile Gln Tyr Trp Gln Ala Thr Trp Ile
450                 455                 460

Pro Glu Trp Glu Phe Val Asn Thr Pro Pro Leu Val Lys Leu Trp Tyr
465                 470                 475                 480

Gln Leu Glu Lys Asn Val Thr Glu Asn Phe Asn Met Trp Lys Asn Asp
                485                 490                 495

Met Val Asp Gln Met His Glu Asp Ile Ile Ser Leu Trp Asp Gln Ser
            500                 505                 510

Leu Lys Pro Cys Val Lys Leu Thr Pro Trp Val Pro Ala His Lys Gly
        515                 520                 525

Ile Gly Gly Asn Glu Gln Val Asp Lys Leu Val Ser Gln Gly Ile Arg
    530                 535                 540

Lys Val Leu Phe Leu Asp Gly Ile Asp Lys Ala Gln Ala Lys Glu Ile
545                 550                 555                 560

Val Ala Ser Cys Asp Lys Cys Gln Leu Lys Gly Glu Ala Met His Gly
                565                 570                 575

Gln Val Asp Cys Ser Pro Gly Ile Trp Gln Leu Asp Cys Thr His Leu
            580                 585                 590

Glu Gly Lys Val Ile Leu Val Ala Val His Val Ala Ser Gly Tyr Ile
        595                 600                 605
```

```
Glu Ala Glu Val Ile Pro Ala Glu Thr Gly Gln Glu Thr Ala Tyr Phe
            610                 615                 620
Leu Leu Lys Leu Ala Met Asn Lys Glu Leu Lys Lys Ile Ile Gly Gln
625                 630                 635                 640
Val Arg Asp Gln Ala Glu His Leu Lys Thr Ala Val Gln Met Ala Val
                645                 650                 655
Phe Ile His Asn Phe Lys Arg Lys Gly Gly Ile Gly Gly Tyr Ser Ala
            660                 665                 670
Gly Glu Arg Ile Trp Lys Gly Pro Ala Lys Leu Leu Trp Lys Gly Glu
        675                 680                 685
Gly Ala Val Val Ile Gln Asp Asn Ser Asp Ile Lys Val Val Pro Arg
    690                 695                 700
Arg Lys Ala Lys Ile Ile Arg Asp Tyr Gly Lys Gln Met Ala Gly Ala
705                 710                 715                 720
Asp Cys Val Phe Leu Gly Ala Ala Gly Ser Thr Met Gly Ala Ala Ser
                725                 730                 735
Met Thr Leu Thr Val Gln Ala Arg Gln Leu Leu Ser Gly Ile Val Gln
            740                 745                 750
Gln Gln Asn Asn Leu Leu Arg Ala Ile Glu Ala Gln Gln His Leu Leu
        755                 760                 765
Gln Leu Thr Val Trp Gly Ile Lys Gln Ala Cys Thr Pro Tyr Asp Ile
    770                 775                 780
Asn Gln Met Leu Arg Gly Pro Gly Arg Ala Phe Val Thr Ile Pro Asn
785                 790                 795                 800
Pro Leu Leu Gly Leu Asp
            805

<210> SEQ ID NO 5
<211> LENGTH: 2382
<212> TYPE: DNA
<213> ORGANISM: Artificial Sequence
<220> FEATURE:
<223> OTHER INFORMATION: Description of Artificial Sequence: Synthetic
      HIV construct

<400> SEQUENCE: 5
ccgattaagc ttcccgggcc cgccgccacc atggaggaga aggccttctc ccccgaggtg      60
atccccatgt tcaccgccct gtccgagggc gccaccccc aggacctgaa caccatgctg    120
aacaccgtgg cggccacca ggccgccatg cagatgctga aggacaccat caacgaggag    180
gccgccgagt gggaccgcat ctacaagcgc tggatcatcc tgggcctgaa caagatcgtg    240
cgcatgtact ccccgtgtc catcctggac atccgccagg cccccaagga gcccttccgc    300
gactacgtgg accgcttcgc cgcaactgc cgcgccccc gcaagaaggg ctgctggaag    360
tgcggcaagg agggccacca gatgaaggac tgcaccgagc gccaggccaa cttcctgggc    420
aagatctggc cctcccgctg gaagcccaag atgatcggcg gcatcggcgg cttcatcaag    480
gtgcgccagt acgaccagat cctgatcgag atctgcggcc acaaggccat cggcaccgtg    540
ctggtgggcc ccaccccgt gaacatcatc ggccgcaacc tgctgaccca gatcggctgc    600
accctgaact tccccatctc ccccatcgag accgtgcccg tgaagctgaa gcccggcatg    660
gacggccccca aggtgaagca gtggcccctg accgaggaga gatcaaggc cctggtggag    720
atctgcaccg agatggagaa ggagggcaag atctccaaga tcggccccga gaacccctac    780
aacacccccg tgttcgccat caagaagaag gactccacca gtggcgcaa gctggtggac    840
ttccgcgagc tgaacaagcg cacccaggac ttctgggagg tgcagctggg catccccac     900
```

```
cccgccggcc tgaagaagaa gaagtccgtg accgtgctgg acgtgggcga cgcctacttc    960
tccgtgcccc tggacgaggg cttccgcaag tacaccgcct tcaccatccc ctccatcaac   1020
aacgagaccc ccggcatccg ctaccagtac aacgtgctgc ccagggctg aagggctcc     1080
cccgccatct tccagtcctc catgaccaag atcctggagc ccttccgcgc ccagaacccc   1140
gagatcgtga tctaccagta catggacgac ctgtacgtgg gctccgacct ggagatcggc   1200
cagcaccgca tggagaaccg ctggcaggtg atgatcgtgt ggcaggtgga ccgcatgcgc   1260
atccgcacct ggaagtccct ggtgaagcac cacctgaccg aggaggccga gctggagctg   1320
gccgagaacc gcgagatcct gaaggacccc gtgcacggcg tgtactacga cccctccaag   1380
gacctgatcg ccgagatcca gtactggcag gccacctgga tccccgagtg ggagttcgtg   1440
aacaccccc ccctggtgaa gctgtggtac cagctggaga gaacgtgac cgagaacttc    1500
aacatgtgga agaacgacat ggtggaccag atgcacgagg acatcatctc cctgtgggac   1560
cagtccctga agccctgcgt gaagctgacc ccctgggtgc ccgcccacaa gggcatcggc   1620
ggcaacgagc aggtggacaa gctggtgtcc cagggcatcc gcaaggtgct gttcctggac   1680
ggcatcgaca aggcccaggc caaggagatc gtggcctcct gcgacaagtg ccagctgaag   1740
ggcgaggcca tgcacggcca ggtggactgc tcccccggca tctggcagct ggactgcacc   1800
cacctggagg gcaaggtgat cctggtggcc gtgcacgtgg cctccggcta catcgaggcc   1860
gaggtgatcc ccgccgagac cggccaggag accgcctact tcctgctgaa gctggccatg   1920
aacaaggagc tgaagaagat catcggccag gtgcgcgacc aggccgagca cctgaagacc   1980
gccgtgcaga tggccgtgtt catccacaac ttcaagcgca agggcggcat cggcggctac   2040
tccgccggcg aggcgatctg gagggccccc gccaagctgc tgtggaaggg cgagggcgcc   2100
gtggtgatcc aggacaactc cgacatcaag gtggtgcccc gccgcaaggc caagatcatc   2160
cgcgactacg gcaagcagat ggccggcgcc gactgcgtgt cctgggcgc cgccggctcc    2220
accatgggcg ccgcctccat gaccctgacc gtgcaggccc ccagctgct gtccggcatc    2280
gtgcagcagc agaacaacct gctgcgcgcc atcgaggccc agcagcacct gctgcagctg   2340
accgtgtggg gcatcaagca gtagcccggg tctagaggac ga                      2382
```

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Pro Asn Pro Leu Leu Gly Leu Asp
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Thr Pro Glu Ser Ala Asn Leu
1               5

<210> SEQ ID NO 8
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Tyr Ile Pro Ser Ala Glu Lys Ile
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Cys Thr Pro Tyr Asp Ile Asn Gln Met Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Thr Pro Tyr Asp Ile Asn Gln Met
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Gly Pro Gly Arg Ala Phe Val Thr Ile
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Pro Tyr Asp Val Pro Asp Tyr Ala
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Tyr Lys Asp Asp Asp Asp Lys
```

```
<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Thr Asp Ile Glu Met Asn Arg Leu Gly Lys
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Tyr Met Pro Met Glu
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Thr Pro Asp Tyr Asn Gln Met
1               5
```

MULTI-CLADE CHIMERIC IMMUNOGENS DERIVED FROM HIGHLY CONSERVED REGIONS OF THE HUMAN IMMUNODEFICIENCY VIRUS TYPE 1 (HIV-1) CONSENSUS PROTEOME

CROSS-REFERENCE TO RELATED APPLICATIONS

This application is a continuation-in-part application of international patent application Serial No. PCT/IB2006/001909 filed 23 Feb. 2006, which published as PCT Publication No. 2006/123256 on 23 Nov. 2006, which claims benefit of U.S. provisional patent application Ser. No. 60/655,764 filed 24 Feb. 2005.

The foregoing application, and all documents cited therein ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

This work was funded, in part, by a grant from the Medical Research Council of the United Kingdom.

FIELD OF THE INVENTION

This invention relates to artificial fusion proteins (AFPs) designed to elicit an anti-HIV immune response in a subject, as well as nucleic acid molecules and expression vectors encoding those proteins. The AFPs, as well as nucleic acids and expression vectors encoding these proteins, may be administered alone or in combination to a subject to generate an anti-HIV immune response. The AFPs of the invention may comprise domains from various HIV proteins, for example, Gag, Pol, Env, and Vif proteins. The HIV proteins that form the domains are partial protein sequences and biologically inactivated for one or more of the normal activities of those proteins. HIVCON is an AFP in which the HIV domains are from multiple HIV clade consensus sequences. HIVCON may also contain additional domains useful, for example, in monitoring protein expression levels or laboratory animal immune responses. Such domains are optionally included in the AFPs. Other aspects of the invention include compositions and methods for inducing an anti-HIV immune response in a subject, preferably using a DNA prime-MVA boost strategy and preferably to induce a cell-mediated immune response.

BACKGROUND OF THE INVENTION

AIDS, or acquired immunodeficiency syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural regulatory proteins. The Gag gene encodes core structural proteins of the nucleocapsid core and matrix. The Pol gene encodes reverse transcriptase, integrase, and viral protease enzymes required for viral replication. The tat gene encodes a protein that is required for elongation of viral transcripts. The rev gene encodes a protein that promotes the nuclear export of incompletely spliced or unspliced viral RNAs. The Vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The Env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas, pp. 454-456).

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

The different isolates of HIV-1 have been classified into three groups: M (main), O (outlier) and N (non-M, non-O). The HIV-1 M group dominates the global HIV pandemic (Gaschen et al., (2002) Science 296: 2354-2360). Since the HIV-1 M group began its expansion in humans roughly 70 years ago (Korber et al., Retroviral Immunology, Pantaleo et al., eds., Humana Press, Totowa, N.J., 2001, pp. 1-31), it has diversified rapidly (Jung et al., (2002) Nature 418: 144). The HIV-1 M group consists of a number of different clades (also known as subtypes) as well as variants resulting from the combination of two or more clades, known as circulating recombinant forms (CRFs). Subtypes are defined as having genomes that are at least 25% unique (AIDS epidemic update, December 2002). Eleven clades have been identified and a letter designates each subtype. When clades combine with each other and are successfully established in the environment, as can occur when an individual is infected with two different HIV subtypes, the resulting virus is known as a CRF. Thus far, roughly 13 CRFs have been identified. HIV-1 clades also exhibit geographical preference. For example, Clade A, the second-most prevalent clade, is prevalent in West Africa, while Clade B is common in Europe, the Americas and Australia. Clade C, the most common subtype, is widespread in southern Africa, India and Ethiopia (AIDS epidemic update, December 2002).

This genetic variability of HIV creates a scientific challenge to vaccine development. HIV-1 is a highly variable virus, for which intra-subtype variation can be as high as 20% and inter-subtype differences can reach 35% of the amino acid sequence (Thomson, M. M. et al (2002) Lancet Infect Dis. 2: 461-471). Although some reports have demonstrated that cross-clade immune responses can be detected (Cao, H. et al. (1997) J. Virol. 71: 8615-8623; Ferrari, G. et al. (1997) Blood 90: 2406-2416; Walker, B. D. et al. (2001) Nat. Immunol. 2: 473-475), other studies conflict (Burrows, S. R. et al. (1992) Eur. J. Immunol. 22: 191-195; McMichael, A. J. et al (2002) Nat. Rev. Immunol. 2: 283-291). Thus, unless clear evidence for very broad cross-clade reactivity becomes available and it is shown that vaccines can induce strong T-cell responses to many epitopes, it is prudent to match the vaccine immunogens to the Clades and/or CRFs in the target population.

Traditional approaches to vaccine development, such as immunization with live attenuated virus, killed virus or viral subunits, are not proving feasible for HIV. For example, in the macaque-SIV model, live attenuated vaccines cause persistent infection, with some macaques developing AIDS. Moreover, it has been difficult to generate effective neutralizing antibodies to clinical isolates of virus. Combinations of traditional and new approaches with novel immunogens designed to elicit humoral and/or cellular immunity may prove necessary and are being actively sought.

With the difficulties encountered for neutralizing antibodies, another approach to HIV vaccine development is to induce cell-mediated immune responses. Such responses are predominantly mediated by cytotoxic T lymphocytes (CTLs). CTLs, also known as CD8+ T-cells, participate in an organism's defense in at least two different ways: by killing virus-infected cells and by secreting a variety of cytokines and chemokines that directly or indirectly contribute to the suppression of virus replication. The induction and maintenance of strong CD8+ T cell responses require "help" provided by CD4+ T-lymphocytes (helper T-cells).

CTLs recognize peptides that originate from both surface and inner structural and nonstructural HIV proteins. Unlike antibodies, they cannot prevent cell-free HIV from infecting host cells. Therefore, the vaccine-induced prophylactic CTLs must act quickly. For that, they may have to be in sufficient numbers, which may or may not require persistent vaccine stimulation or regular re-vaccinations. Preferably, vaccine-induced CTLs should recognize early and/or abundant HIV proteins of the transmitting virus/clade, target multiple CTL epitopes in functionally conserved protein regions to make it difficult for HIV to escape, and kill target cells efficiently.

To induce CTLs, a prime-boost immunization strategy using plasmid DNA encoding an immunogen as a priming immunization, followed by a boosting immunization with a recombinant virus encoding the same immunogen, has demonstrated efficacy to stimulate CD8+ T cell responses in mice (Hanke et al., (1998a) Vaccine 16:439-445; Schneider et al., (1998) Nat. Med. 4: 397-402; Kent et al., (1998) J. Virol. 72:10180-10188). This strategy has been confirmed and extended for non-human primates (Hanke et al, (1999) J. Virol 73:7524-7532; Allen et al., (2000a) J. Immunol. 164: 4968-4978; Amara et al., (2001) Science 292:69-74; Allen et al., (2002) J. Virol. 76:10507-10511; Shiver et al., (2002) Nature 415:331-335) and humans (McConkey et al., (2003) Nat. Med. 9:729-35). WO 98/56919 discloses a prime-boost immunization strategy to generate a CTL-mediated immune response against malarial and other antigens, such as viral and tumor antigens. This immunization strategy uses priming and boosting compositions, which deliver the same CTL epitope in different vectors, where the vector for the boosting composition is a replication-defective poxvirus vector.

Another aspect of vaccine development is to find formulations capable of inducing CTL responses specific for multiple HIV epitopes. Such vaccines could make it relatively difficult for HIV to escape and would have a better chance to suppress HIV replication. Theoretically, several smaller immunogens delivered individually by separate vaccine vectors would be advantageous over one large multigenic protein expressed from a single vector, because the former immunogens may reach separate antigen-presenting cells and each induce at least one immunodominant response (Singh, R. A. et al., (2002) J. Immunol. 168:379-391). With a multigenic protein, unless cross-priming plays a role in immune stimulation, each component is produced by one cell and thus competes with the others for presentation. Hence, a balance is needed between the breadth of elicited immune responses and practicalities of vaccine development and production, the former increasing and the latter decreasing the number of vaccine components.

Yet another aspect of vaccine development is to address HIV variability. First, vaccines could alternate HIV Clades using one protein from each Clade in their formulations. Second, a cocktail of all immunogens derived from the two or three most common HIV Clades could be used, because the immune system has the capacity to respond to many different epitopes. However, as for other vaccine approaches, "immunodominance" of epitopes could narrow the breadth of T cell responses and prevent prophylactic immunity in response to viral infection (Yewdell, J. W. et al. (1999) Ann. Rev. Immunol. 17: 51-88).

During the course of a viral infection, CTL responses develop a predictable bias in their pattern of epitope recognition. A hierarchy of epitope recognition develops, with most of the CTL response targeted to a very limited number of epitopes. This phenomenon is also known as "immunodominance". Experimental evidence suggests that immunodominance develops as a consequence of many factors, such as the variety of epitope affinities for the relevant cellular receptor, i.e., major histocompatibility complex (MHC) Class I molecule, the various copy numbers of the epitopes produced by the virus, and differences in epitope processing by the host cellular machinery. Therefore, vaccine strategies that can bypass the hierarchy of epitope bias could result in a broad CTL response that provides a protective immune response against viral infection.

With a few exceptions, most of the known CTL epitopes have been identified in chronically infected individuals and responses to these epitopes have heretofore failed to protect against HIV infection. However, other studies have illustrated that the dominant response is not necessarily the most protective (Gallimore, A. et al (1998) J. Exp. Med. 187: 1647-

1657). It is therefore a highly desirable advance in the art to develop HIV immunogens based on conserved protein regions, which are, by definition, common to all Clades (Wilson, C. C. et al. (2003) J. Immunol. 171: 5611-5623). Such an immunogen could comprise conserved protein regions that do not necessarily contain epitopes that are naturally processed by HIV-infected cells, but also comprise subdominant or cryptic epitopes that may be protective. An immunogen capable of inducing strong responses against subdominant epitopes could avoid the problem of immunodominance and therefore, induce broad T-cell responses. Further, cross-clade or clade-universal CTL reactivity could allow for less localized geographic use of such an immunogen.

Citation or identification of any document in this application is not an admission that such document is available as prior art to the present application.

SUMMARY OF THE INVENTION

It has now been surprisingly discovered that the sequences selected from the most highly conserved regions of selected HIV proteins, such as Gag, Pol, Vif, and Env, can induce immune responses against HIV that are not restricted by HIV Clade or CRF. The present invention therefore, in certain embodiments, provides an artificial fusion protein (hereinafter "AFP") comprising HIV sequences from Gag, Pol, Vif, and Env, wherein the sequences may comprise the most highly conserved regions of Gag, Pol, Vif, and Env, and which are selected irrespective of Clade, CRF, or the presence or abundance of dominant CTL epitopes. Also provided are isolated nucleic acids expressing the AFP, expression vectors and host cells which may comprise the nucleic acid expressing the AFP, methods for expressing the AFP, and methods for inducing immune responses to the AFP in a subject.

Accordingly, one aspect of the present invention provides an AFP which may comprise an HIV Gag domain, one or more HIV Pol domains, an HIV Vif domain, and one or more HIV Env domains. In one embodiment, each of the HIV Gag, Pol, Vif, and Env may be selected so that the AFP induces an immune response to a pre-determined HIV Clade. In an alternative embodiment, the amino acid sequences for each of the HIV Gag, Pol, Vif, and Env domains may be selected from HIV consensus sequences for different HIV Clades. Preferably, the HIV Clade may be selected from the group consisting of Clade A, A1, A2, B, C, and D.

Another embodiment relates to the amino acid sequences for each of HIV Gag, Pol, Vif, and Env, which may vary by from about 0% to about 10% between HIV Clades. Preferably, the sequences may vary from about 0% to about 8% between Clades, and even more preferably, from about 0% to about 6% between Clades.

In another embodiment, the domains may be present from N- to C-terminus in any order that does not recreate a naturally-occurring protein. Preferably, the domains may be present from N- to C-terminus in order of: HIV Gag domain, a first HIV Pol domain, HIV Vif domain, a second HIV Pol domain, a first HIV Env domain, a third HIV Pol domain, and a second HIV Env domain. The domains may be joined with or without intervening sequences.

The HIV Gag domains preferably may comprise a sequence of amino acids from an HIV isolate or an HIV consensus sequence corresponding to amino acids 1-135 of SEQ ID NO: 2. The HIV Gag domain may comprise three HIV Gag subdomains, which can be from the same HIV Clade, or from different HIV Clades. In a preferred embodiment, the first HIV Gag subdomain may comprise amino acids 1-56 of SEQ ID NO: 2 and the sequence is from HIV Clade C. The second HIV Gag subdomain preferably comprises amino acids 57-96 of SEQ ID NO: 2 and the sequence may be from HIV Clade D. The third HIV Gag subdomain preferably may comprise amino acids 97-135 of SEQ ID NO: 2 and the sequence may be from HIV Clade A.

The HIV Pol domains preferably may comprise three HIV Pol domains, wherein the first HIV Pol domain preferably may comprise amino acids 136-393 of SEQ ID NO: 2, the second HIV Pol domain preferably may comprise amino acids 422-484 of SEQ ID NO: 2, and the third HIV Pol domain preferably may comprise amino acids 522-723 of SEQ ID NO: 2. Preferably, each HIV Pol domain may comprise at least two HIV Pol subdomains. The at least two HIV Pol subdomains may be from the same or different HIV Clades. The first HIV Pol subdomain of the first HIV Pol domain preferably may comprise amino acids 136-265 of SEQ ID NO: 2 and the sequence may be from HIV Clade B. The second HIV Pol subdomain of the first HIV Pol domain preferably may comprise amino acids 266-393 of SEQ ID NO: 2 and the sequence may be from HIV Clade C. The first HIV Pol subdomain of the second HIV Pol domain preferably may comprise amino acids 432-467 of SEQ ID NO: 2 and the sequence may be from HIV Clade A. The second HIV Pol subdomain of the second HIV Pol domain preferably may comprise amino acids 468-494 of SEQ ID NO: 2 and the sequence may be from HIV Clade B. The first HIV Pol subdomain of the third HIV Pol domain preferably may comprise amino acids 522-556 of SEQ ID NO: 2 and the sequence may be from HIV Clade D. The second HIV Pol subdomain of the third HIV Pol domain preferably may comprise amino acids 557-629 of SEQ ID NO: 2 and the sequence may be from HIV Clade A. The third HIV Pol subdomain of the third HIV Pol domain preferably comprises amino acids 630-676 of SEQ ID NO: 2 and the sequence may be from HIV Clade B. The fourth HIV Pol subdomain of the third HIV Pol domain preferably may comprise amino acids 677-723 of SEQ ID NO: 2 and the sequence may be from HIV Clade C.

The HIV Vif domain preferably may comprise amino acids 394-421 of SEQ ID NO: 2 and the sequence may be from HIV Clade D. The first HIV Env domain preferably may comprise amino acids 485-521 of SEQ ID NO: 2 and the second HIV Env domain preferably may comprise amino acids 724-777 of SEQ ID NO: 2. The first HIV Env domain may be preferably from HIV Clade C, and the second HIV Env domain may be preferably from HIV Clade D.

The present invention also provides an AFP comprising amino acids 1-777 of SEQ ID NO: 2. The AFPs of the present invention may also further comprise one or more non-human CTL domains for monitoring immune responses to the AFP in a laboratory animal, such as those selected from the group consisting of the SIV tat CTL epitope, the pb9 epitope, the P18-I10 epitope, and the SIV gag p27 epitope. The AFPs of the present invention may also further comprise a marker domain selected from the group consisting of Pk, Flag, HA, myc, GST or His epitopes. A further aspect of the invention provides an AFP comprising amino acids 1-806 of SEQ ID NO: 2.

Another aspect of the present invention provides isolated nucleic acids which may have a nucleotide sequence encoding the AFPs of the invention. Further, the invention also provides expression vectors comprising a nucleic acid having a nucleotide sequence encoding the AFP of the present invention, operably linked to at least one nucleic acid control sequence. The nucleic acids and vectors of the invention are particularly useful for providing genetic vaccines, i.e. vaccines for delivering the nucleic acids encoding the AFPs of the present invention to a subject such as a human, such that the AFPS are then expressed in the subject to elicit an immune response.

The expression vector may be a plasmid vector, a viral vector, an insect vector, a yeast vector, or a bacterial vector. Preferably, the plasmid vector is pTH or pTHr.

The viral vector may be an alphavirus replicon vector, an adeno-associated virus vector, an adenovirus vector, a retrovirus vector, a poxvirus vector, or any other suitable viral vector. When the vector is a poxvirus vector, the poxvirus vector is selected from the group consisting of vaccinia virus and avipox virus. The poxvirus may be an attenuated poxvirus, such as MVA, NYVAC, TROVAC, or ALVAC.

The expression vector may also be a bacterial vector, such as a live attenuated *Salmonella* or a *Shigella* vector.

In preferred embodiments, the nucleic acid control sequence may be a cytomegalovirus (CMV) immediate early promoter.

Preferably, the codons encoding the AFPs of the invention may be those of highly expressed genes for a target subject or host cell in which the AFP is to be expressed. The subject is advantageously a human. In certain embodiments, the expression vector pTH or pTHr may contain the HIVCON coding sequence and is referred to as pTH.HIVCON or pTHr.HIVCON, respectively. Alternatively, the expression vector MVA may be used resulting in and nucleic acid referred to as MVA.HIVCON.

A further aspect of the present invention provides host cells comprising the expression vectors of the invention.

The invention also provides a method of preparing an AFP, which may comprise (a) culturing the host cell of the invention for a time and under conditions to express the AFP; and (b) recovering the AFP.

Another aspect provides methods for introducing into and expressing an AFP in an animal, which may comprise delivering an expression vector of the invention into the animal and thereby obtaining expression of the AFP in the animal.

Methods for expressing an AFP in animal cells are also provided, which may comprise (a) introducing an expression vector of the present invention into the animal cells; and (b) culturing those cells under conditions sufficient to express the AFP.

A further aspect of the present invention provides methods for inducing an immune response in an animal, which may comprise delivering an expression vector of the invention into the animal, wherein the AFP is expressed at a level sufficient to induce an immune response to the AFP.

Methods of inducing an immune response against HIV in a human subject are also provided, which may comprise administering an immunogen one or more times to a subject, wherein the immunogen is selected from the group consisting of (i) an AFP of the invention, (ii) a nucleic acid encoding the AFP, and (iii) an expression vector encoding the AFP; and wherein the AFP is administered in an amount or expressed at a level sufficient to induce an HIV-specific CTL immune response in the subject. Preferably, the subject receives at least two administrations of the immunogen, or a vector or nucleic acid encoding the immunogen, at intervals of at least two weeks or at least four weeks. Another embodiment provides another HIV immunogen administered at the same time or at different times as part of an overall immunization regime.

Yet another aspect of the present invention provides methods of inducing an immune response against HIV in a human subject, which may comprise administering to the subject at least one priming dose of an HIV immunogen and at least one boosting dose of an HIV immunogen, wherein the immunogen in each dose can be the same or different, provided that at least one of the immunogens is an AFP of the invention, or is a nucleic acid or an expression vector encoding the AFP, wherein the immunogens are administered in an amount or expressed at a level sufficient to induce an HIV-specific T-cell immune response in the subject.

The interval between each dose can be at least two weeks or at least four weeks. Preferably, pTHr.HIVCON is administered one or more times as a priming dose and MVA.HIVCON is administered one or more times as a boosting dose. An alternative embodiment comprises administering two priming doses and administering two boosting doses, wherein the immunogen used for the priming doses is a plasmid vector and the immunogen used for the boosting doses is a viral vector. The viral vector can be an MVA vector. Each of the priming doses can be a mixture of vectors selected from the group consisting of pTHr.HIVA, pTHr.RENTA, and pTHr.HIVCON and each of the boosting doses can be a mixture of vectors selected from the group consisting of MVA.RENTA, MVA.HIVA, and MVA.HIVCON.

Another aspect of the invention provides immunogenic compositions comprising an AFP of the invention, or a nucleic acid encoding the AFP, or an expression vector encoding the AFP; and a pharmaceutically acceptable carrier. The compositions may further comprise an adjuvant selected from the group consisting of mineral salts, polynucleotides, polyarginines, ISCOMs, saponins, monophosphoryl lipid A, imiquimod, CCR-5 inhibitors, toxins, polyphosphazenes, cytokines, immunoregulatory proteins, immunostimulatory fusion proteins, co-stimulatory molecules, and combinations thereof. Such compositions may be useful as vaccines against HIV. The nucleic acids and vectors of the invention may be particularly useful for providing genetic vaccines, i.e. vaccines for delivering the nucleic acids encoding the AFPs of the present invention to a subject such as a human, such that the AFPS are then expressed in the subject to elicit an immune response.

The present invention also provides a library of immunogenic polypeptides, comprising a plurality of polypeptides comprising at least 8-15 successive amino acids of SEQ ID NO: 2 or SEQ ID NO: 4, wherein each immunogenic polypeptide corresponds to at least a portion or fragment of SEQ ID NO: 2 or SEQ ID NO: 4. In one embodiment, the plurality of immunogenic polypeptides correspond in total to the entire length of SEQ ID NO: 2 or SEQ ID NO: 4. Preferably, a portion of each polypeptide in the library comprises overlapping amino acid sequences, particularly by at least eleven amino acids.

Yet another aspect of the invention provides a method of identifying a CTL epitope against HIV from the library of immunogenic polypeptides of the invention in a cell expressing MHC Class I protein, which may comprise the steps of contacting the cell with the library of the invention, selectively binding the library with the MHC protein of the cell, isolating a polypeptide of the library that selectively binds to MHC, and sequencing the polypeptide, thereby identifying the CTL epitope. The cell may be an antigen-presenting cell, preferably a splenocyte. The cell may be a human cell. When the cell is a human cell, the MHC Class I protein is human leukocyte antigen (HLA). In one embodiment, selective binding is measured by flow cytometry. In another embodiment, the polypeptide is isolated by chromatography.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following Detailed Description, given by way of example, but not intended to limit the invention to the specific embodiments described, may be best understood in conjunction with the accompanying Figures.

FIG. 2 is the nucleotide sequence of SEQ ID NO. 1, a 2334 nucleotide sequence that encodes an HIVCON immunogen that does not comprise the three additional epiptopes (monkey CTL epitope (Mamu), mouse CTL epitope (P18-I10/H2) and mAb epitope Pk) following the last Env domain. SEQ ID NO. 1 starts at the first ATG (encoding the first methionine) and terminates with a stop codon (TAG) after the nucleotides encoding the last amino acid of the last Env domain.

FIG. 3 is the amino acid sequence of SEQ ID NO. 2, the 777 amino acid immunogen encoded by SEQ ID NO. 1. This HIVCON immunogen does not comprise the three additional epiptopes (monkey CTL epitope (Mamu), mouse CTL epitope (P18-I10/H2) and mAb epitope Pk) following the last Env domain.

FIG. 4 is the nucleotide sequence of SEQ ID NO. 3, a 2421 bp nucleotide sequence that encodes an HIVCON immunogen comprising a monkey CTL epitope (Mamu), a mouse CTL epitope (P18-I10/H2) and a mAb epitope (Pk) following the last Env domain. The first 2331 nucleotides are the same as the 2331 coding nucleotides of SEQ ID NO. 1 (i.e. the sequence of SEQ ID NO. 1 without the last stop codon). The last 90 nucleotides are those that encode the monkey CTL epitope (Mamu), the mouse CTL epitope (P18-I10/H2) and the mAb epitope (Pk).

FIG. 5 is the amino acid sequence of SEQ ID NO. 4, an 806 amino acid immunogen that encodes an HIVCON immunogen comprising a monkey CTL epitope (Mamu), a mouse CTL epitope (P18-I10/H2) and a mAb epitope (Pk) following the last Env domain. The first 777 amino acids are the same as SEQ ID NO. 2. The last 29 amino acids are those that encode the monkey CTL epitope (Mamu), the mouse CTL epitope (P18-I10/H2) and the mAb epitope (Pk).

FIG. 6 is the nucleotide sequence of SEQ ID NO. 5, 2382 nucleotide sequence encoding an HIVCON immunogen. The first 18 nucleotides comprise two restriction sites (a SmaI/XmaI site and a XbaI site). These sites can be used to insert/remove the HIVCON coding sequence into vectors such as the pTH or pTHr vectors described herein. The next 12 nucleotides comprise the Kozak consensus leader sequence CAC-CATG (underlined). Nucleotides 30-2364 are the HIVCON coding sequence of FIG. 2 (SEQ ID NO: 1) and encode the HIVCON immunogen of FIG. 3 (SEQ ID NO. 4)—i.e. without the additional three epitopes added. Nucleotides 30-2364 are shown in bold typeface. The last 18 nucleotides comprise two restriction sites (a SmaI/XmaI site and a XbaI site) that can be used to insert/remove the HIVCON coding sequence into various vectors such as the pTH or pTHr vectors described herein.

FIG. 11. Immunogenicity of HIVCON vaccines in BALB/c mice. (A) Immunogenicities of the individual vaccine components. Splenocytes from individual animals were tested ex vivo for the production of IFN-γ in an ELISPOT assay using the RGPGRAFVTI (SEQ ID NO. 11) epitope. (B) As for A, but with higher doses for the MVA.HIVCON and Ad.HIVCON vaccines. (C) Immunogenicities of individual vaccine components compared to various prime-boost vaccination regimes, using an IFN-γ ELISPOT assay as above. (D) Immunogenicities of individual vaccine components compared to a DNA prime-MVA boost vaccination regime. Splenocytes from individual animals were restimulated for 5 days in 5 culture with the RGPGRAFVTI (SEQ ID NO. 11) peptide and tested in a $^{51}$Cr-release assay on peptide pulsed (full) or unpulsed (open) targets.

DETAILED DESCRIPTION OF THE INVENTION

Figure 1:
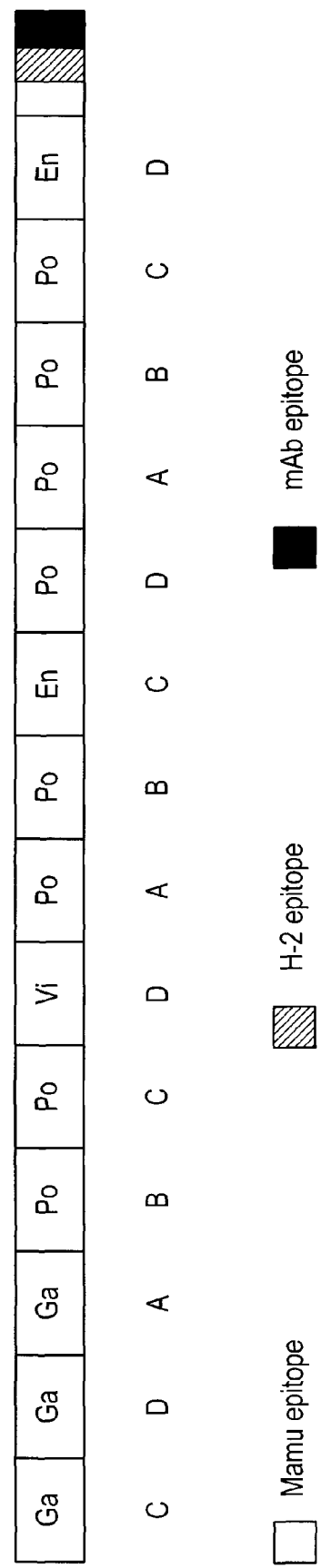
FIG. 1 is a schematic representation of the HIVCON immunogen. The HIVCON immunogen is a chimeric protein derived from highly conserved domains of HIV proteins. The gene of origin for each sequence domain is shown in the box, while the Clade of origin (of the consensus sequence) is shown below. Ga=Gag; Po=Pol; Vi=Vif, En=Env. The version of HIVCON shown in the figure also has one monkey CTL epitope (Mamu), one mouse CTL epitope (P18-10, discussed below and indicated as H-2 in the schematic) and a monoclonal antibody (mAb) epitope (Pk) following the last Env domain. Other versions of the HIVCON immunogen, as described herein, may not have these last three additional domains, and instead terminate at the last Env domain.

An "immunogen" refers to a substance that is recognized by the immune system and induces an immune response. A similar term used in this context is "antigen".

A "subject" in the context of the present invention may be a vertebrate, such as a mammal, bird, reptile, amphibian or fish; more advantageously a human, or a companion or domesticated or food-producing or feed-producing or livestock or game or racing or sport animal such as a cow, a dog, a cat, a goat, a sheep or a pig or a horse, or even fowl such as turkey, ducks or chicken. Preferably, the vertebrate is a human.

The terms "protein", "peptide", "polypeptide" and "polypeptide fragment" may be used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" polynucleotide or polypeptide may be one that is substantially free of the materials with which it is associated in its native environment. By substantially free, is meant at least 50%, advantageously at least 70%, more advantageously at least 80%, and even more advantageously at least 90% free of these materials.

The present invention relates to AFPs for promoting immune responses to HIV in a human subject. These AFPs are non-naturally occurring proteins that comprise multiple HIV domains. The AFPs of the invention can optionally comprise one or more additional domains useful for monitoring expression levels of an AFP in cells or laboratory animals and/or immune responses to the AFP in laboratory animals.

In particular, the AFPs of the invention comprise Gag, Pol, Vif, and Env sequences. These sequences encompass (a) an HIV Gag domain, (b) one or more HIV Pol domains; (C) an HIV Vif domain; and (d) one or more HIV Env domains. The amino acid sequence of the HIV domains can be selected so that the AFP predominantly induces an immune response to a pre-determined HIV Clade. For example, if an immune response against HIV Clade A is desired, then the amino acid sequences for Gag, Pol, Vif, and Env are preferably the Clade A consensus sequences for each of those proteins. Preferably, the AFPs of the invention comprise HIV domains that are selected from among several different Clades, so as to provide a cross-clade or clade-universal immunogen against HIV.

More particularly, an "artificial fusion protein" or "AFP" as used herein is a protein or polypeptide (these terms are used interchangeably) which does not naturally occur in nature, i.e., AFPs are the product of a design process and the entire AFP as designed is not naturally encoded in the genome of an organism. An AFP of the invention must have at least two distinct protein domains arranged in a non-naturally occurring manner, i.e., the two domains are arranged (or fused together) in a manner not normally found in a single protein. For domains originating from different proteins, the arrangement (or order of joining) is flexible. If the two domains are from the same protein or from a single polyprotein, such as a viral polyprotein, the domains are joined together in a manner to provide a primary linear structural arrangement that differs from the original primary structure associated with those domains, as they are encoded in the protein is in the genome of the organism from which the domains are derived. For example, contiguous domains from a single protein can be joined in reverse order or can be separated by an intervening domain. For example, an AFP could be made by figuratively cutting a protein in half and reordering the coding sequence for (or fusing) the fragments so that the sequence normally found at the carboxy end of the protein is now at the amino terminus of the AFP and the original amino-terminal amino acid is in the middle of the protein.

The domains of the AFPs can be joined by any means, including, without limitation, by covalent bonds, such as a peptide bond or via insertion of a chemical linker, or by non-covalent bonds, such as an ionic bond. Preferably, the domains of the AFPs are joined by covalent bonds. As used herein, "domain" means a region or sequence of amino acids from a protein or polypeptide without regard to whether that region or sequence forms a particular structural or functional unit. A "domain" can also comprise one or more "subdomains", which can comprise parts of proteins, or fragments of proteins or peptides. However, the selection of particular amino acids as a domain or subdomain does not preclude that domain or subdomain from also being a structural and/or functional unit of the protein or polypeptide or from having been selected on the basis of its structure or function.

The size of the domain can vary from a few (less than 10) to many hundreds of amino acids, with the actual domain size based on the reason that particular domain is included in the AFP. For example, a domain that serves as a spacer may range from 2-3 amino acids to 10-15 amino acids, with the exact number of amino acids determined as needed, e.g., to facilitate cloning sites, to avoid frameshifts in the reading frames of the coding sequences, to provide a particular distance between domains, or for any combination of these or other reasons. As another example, a domain whose function is to encode CTL epitopes may range from 5-12 amino acids if a single epitope is encoded, or may be several hundred amino acids if multiple epitopes are encoded. If desired, a domain in the AFP can consist of an entire protein or modified versions of an entire protein, again as dictated by the reason for including that domain in the AFP.

The amino acid sequence of a domain is determined by the nature of the individual domain of the present invention and described in detail below. In this regard, those sequences include naturally-occurring sequences, modified sequences, consensus sequences and the like. Sequence modifications can be achieved by deleting, inserting or changing one or more amino acids. New domains can be made by changing the normal arrangement of amino acids, e.g., by transposing different parts of the protein.

The amino acid sequence for the Gag, Pol, Vif, and Env domains in the AFPs of the invention can be from a consensus sequence for a specific Clade to preferentially generate an immune response to that specific Clade. Alternatively, the amino acid sequences of the domains can be selected to generate an immune response against any of the other HIV Clades, by using amino acid sequences conserved within, and characteristic of, the selected Clade. HIV Clades include Clades A, B, C, D, H, F, G, H, I, J, and K. Consensus sequences from CRFs can also be used.

The simplest form of a consensus sequence can be created by selecting the most frequent amino acid at each position of a protein in a set of aligned protein sequences. Thus, as the number of proteins being compared increases, the consensus sequence can also change. The consensus sequence for HIV proteins from different clades is regularly updated by the Los Alamos HIV database and is readily available to the public. While these compilations may evolve over time as additional isolates of HIV are analyzed and as Clade groupings are altered, this evolution does not affect the use of consensus sequences in the present invention. Any of these published consensus sequences or any consensus sequence derived from a desired group of sequences can be used in the invention.

To select the equivalent, corresponding, or correlating amino acids for the domains of the invention (these terms are used interchangeably), one of skill in the art can align the candidate HIV isolate or consensus sequence with the indicated amino acids of SEQ ID. NO: 2 and thereby determine the corresponding sequence, making allowances for deletions and insertions of amino acids in that region of sequence. It is well known that such alignments may not yield precisely the same length of amino acid sequences due to well known HIV variation. Consequently, the domains for equivalent sequences generally vary in size from 1 to 15 amino acids (or fewer, preferably from 1-10 or 1-5 amino acids and more preferably 1, 2 or 3 amino acids) to accommodate small insertions and deletions. Such insertions and deletions can occur within or at the ends of the equivalent sequence, provided that such length alterations are those one of skill in the art would obtain in maximizing the alignment between the candidate HIV sequence and the indicated portions of SEQ ID NO: 1. Alignment techniques, including manual methods or computerized algorithms, are known to those of skill in the art (Altschul, S. F. et al. (1990) J. Mol. Biol. 215: 403-410).

The domains of the AFPs can be arranged in a variety of different ways (e.g., in a linear order from N- to C-terminus or via chemical crosslinking) without significantly affecting the immunogenic character of the AFP. Accordingly, the AFPs can have the domains arranged in any order that preserves immunogenicity, preserves the required characteristics of the individual domains (e.g., abolishes the relevant biological activity), and does not recreate a naturally-occurring protein.

The AFPs can be synthesized by conventional chemical techniques, such as solid phase synthesis or produced by recombinant DNA technology, preferably the latter. Individually-produced domains can be purified and joined by chemical cross-linking or any other method known in the art. Methods of synthesis, recombinant DNA techniques to produce proteins and chemical cross-linking methods are well known to those of skill in the art. Hence, the invention includes methods of preparing AFPs by culturing a host cell containing an expression vector of the invention (see below) for a time and under conditions sufficient to express the AFP, and recovering the AFP. Methods useful to recover, and/or purify the AFP to homogeneity can be determined by those of skill in the art. Such methods include cesium chloride centrifugation, oligonucleotide affinity chromatography, ethanol precipitation, among others.

The domains and intervening sequences of the AFPs of the invention are described in detail below. A description of HIVCON, a preferred embodiment of the present invention, is also described below.

The HIV Gag domain of the AFPs preferably comprise three subdomains, but can contain one, two, or any number of subdomains, provided that the Gag sequences do not form a naturally-occurring protein. The HIV Gag subdomains preferably correlate to sequences of the most highly conserved regions of the Gag protein among the four most prevalent HIV clades A-D, with less than about 6% variability across HIV Clades A-D. The HIV Gag sequences need not contain dominant CTL epitopes, however the skilled artisan can readily identify and incorporate sequences that are rich in dominant CTL epitopes, so as to elicit or stimulate a targeted cell-mediated immune response. Without wanting to be bound by theory, it is believed that the presence of subdominant epitopes may elicit or stimulate a protective immune response, possibly without inducing the immunodominance effect observed with the use of dominant epitopes. In a preferred embodiment, the HIV Gag sequences of the invention are selected irrespective of the presence or abundance of dominant CTL epitopes.

The HIV Gag sequences can also be selected from the same Clade, thereby targeting the AFP of the invention to a specific target population where a particular Clade is prevalent. The HIV Gag domain can comprise one or more Gag subdomains that comprise sequences that exhibit more or less than about 6% variability across Clades. The Gag sequences can differ by about 0-10%, preferably about 0-8%, and more preferably, about 0-6%. Any HIV Gag sequence can be used in the AFPs of the invention, provided that the Gag sequences are highly conserved and exhibit the desired variability among the HIV clades and target population to be delivered, as well as preserving the desired immunogenicity. Additionally, the HIV Gag sequence should not be configured or positioned in the AFP to create a naturally-occurring Gag protein.

HIVCON, a preferred embodiment of the invention, comprises an HIV Gag domain having amino acids 1-135 of SEQ ID NO: 2 or SEQ ID NO: 4. The HIV Gag domain of the invention comprises three subdomains in HIVCON. Each of the three Gag subdomains in HIVCON comprise the following amino acids: Gag subdomain 1 comprises amino acids 1-56 of SEQ ID NO: 2 or SEQ ID NO: 4; Gag subdomain 2 comprises amino acids 57-96 of SEQ ID NO: 2 or SEQ ID NO: 4; and Gag subdomain 3 comprises amino acids 97-135 of SEQ ID NO: 2 or SEQ ID NO: 4 (see also Table 1).

The AFPs of the present invention preferably comprise three Pol domains, but can include any number of domains (and accordingly, subdomains within the domains), so long as the Pol sequences selected do not form a naturally-occurring protein, or additionally or alternatively, provided that the sequences retain their desired immunogenicity and provided that the sequences do not restore Pol enzymatic activity. Such enzymatic activity includes reverse transcriptase, integrase, protease, and RNase H. The first and second Pol domains each preferably comprise two Pol subdomains, while the third Pol domain preferably comprises four Pol subdomains. The Pol sequences preferably correlate to sequences that are the most highly conserved and which differ by less than 6% across HIV clades A-D. The HIV Pol domains need not contain dominant CTL epitopes, however the invention also contemplates selecting sequences that are rich in dominant CTL epitopes. Preferably, the HIV Pol domains are selected irrespective of the presence or abundance of dominant CTL epitopes.

The HIV Pol sequences can also be selected from the same Clade and/or CRF, thereby targeting the AFP of the invention to a specific target population. Alternatively, the HIV Pol sequences can also be selected from different Clades or CRFs. The HIV Pol domains can comprise one or more Gag subdomains that comprise sequences that exhibit more or less than about 6% variability across HIV clades. The HIV Pol sequence can differ by about 0-10%, preferably about 0-8%, and more preferably, about 0-6%. Any HIV Pol sequence can be used in the AFPs of the invention, provided that the HIV Pol sequences are highly conserved and exhibit the desired variability among the HIV clades and target population to be delivered. Additionally, the selected HIV Pol sequences should lack enzymatic activity of one or all of protease, integrase, RNase, and reverse transcriptase.

HIVCON, a preferred embodiment of the invention, comprises three HIV Pol domains corresponding to: the first Pol domain comprises two subdomains correlating to amino acids 136-393 of SEQ ID NO: 2 or SEQ ID NO: 4; the second Pol domain comprises two subdomains correlating to amino acids 422-484 of SEQ ID NO: 2 or SEQ ID NO: 4; and the third Pol domain comprises four subdomains correlating to amino acids 522-723 of SEQ ID NO: 2 or SEQ ID NO: 4. The amino acids of each Pol subdomain are collectively shown in Table 1.

The HIV Vif domain of the AFPs of the present invention are preferably selected from sequences of the most highly conserved region or regions of Vif among the four most prevalent HIV clades A-D, with less than about 6% variability across clades. The HIV Vif sequence need not contain dominant CTL epitopes, and alternatively may comprise subdominant CTL epitopes. One of skill in the art can readily substitute regions of Vif that are rich in dominant CTL epitopes in order to target a cell-mediated immune response in a particular target population. Preferably, the HIV Vif sequence of the invention is selected irrespective of the presence or abundance of dominant CTL epitopes.

The HIV Vif sequence can be selected from across divergent HIV Clades and CRFs, in comparison to the other HIV sequences present in the AFPs of the invention. The HIV Vif domain can comprise sequences that exhibit more or less than about 6% variability across HIV clades. Preferably, the HIV Vif sequence differ by about 0-10%, preferably about 0-8%, and more preferably, about 0-6%. Any HIV Vif sequence can be used in the AFPs of the invention, provided that the Vif sequence is highly conserved and exhibit the desired variability among the HIV clades and target population to be delivered. The selected HIV Vif sequence should also preserve the desired immunogenicity.

A preferred embodiment of the invention, HIVCON, comprises an HIV Vif domain having amino acids 394-421 of SEQ ID NO: 2 or SEQ ID NO: 4 (Table 1).

The AFPs of the present invention preferably comprise at least two Env domains. The Env domains preferably correlate to sequences that are the most highly conserved and which exhibit less than 6% variability across HIV Clades A-D. The HIV Env domains need not contain dominant CTL epitopes, however the invention also contemplates selecting Env sequences that are rich in dominant CTL epitopes. Such a substitution could result in an enhanced cell-mediated immune response that can be targeted to a specific population where a particular Clade or CRF is predominant. Preferably, the HIV Env domains are selected irrespective of the presence or abundance of dominant CTL epitopes.

When designing an AFP that is targeted to a specific HIV Clade, the HIV Env sequences can also be selected from that HIV Clade or CRF, thereby targeting the AFP of the present invention to a specific target population. The HIV Env sequences can comprise sequences that exhibit less than about 6% variability across HIV Clades. The Env sequences can differ by about 0-10%, preferably about 0-8%, and more preferably, about 0-6%. Any HIV Env sequence can be used in the AFPs of the invention, with the proviso that the Env sequences are highly conserved and exhibit the desired variability among the HIV Clades and target population to be delivered, as well as preserve the desired immunogenicity.

Table 1 depicts each HIV domain of HIVCON, a preferred embodiment of the present invention, including subdomains of each domain, and the appropriate amino acids corresponding to SEQ ID NO: 2. The same amino acid sequences are found at the same positions in SEQ ID NO:2.

TABLE 1

HIV domains of HIVCON

| Domain | Subdomain | Amino Acid of SEQ ID NO: 2 | Clade |
|---|---|---|---|
| Gag | 1 | a.a. 1-56 | C |
|  | 2 | a.a. 57-96 | D |
|  | 3 | a.a. 97-135 | A |
| Pol Domain 1 | 1 | a.a. 136-265 | B |
|  | 2 | a.a. 266-393 | C |
| Pol Domain 2 | 1 | a.a. 422-457 | A |
|  | 2 | a.a. 458-484 | B |
| Pol Domain 3 | 1 | a.a. 522-556 | D |
|  | 2 | a.a. 557-629 | A |
|  | 3 | a.a. 630-676 | B |
|  | 4 | a.a. 677-723 | C |
| Vif | — | a.a. 394-421 | D |
| Env Domain 1 | — | a.a. 485-521 | C |
| Env Domain 2 | — | a.a. 724-777 | D |

The AFPs of the invention can have additional, non-HIV domains to aid in characterization and monitoring of the AFP. Preferably such domains are at the N and/or C-termini of the AFP, but they can also be interposed between the HIV domains of the AFP. For example, the additional domains can encode intra- or extracellular signals or sites that affect processing of the polypeptide (e.g., to include a protease cleavage site, signal sequence for intracellular localization or trafficking, or other such sequence), sites to aid protein purification and/or sites to aid protein localization. Sites useful for protein purification or localization include sequences that enable affinity binding. For example, epitopes recognized by antibodies (including, but not limited to, Pk, Flag, HA, myc, GST or His) that are well known in the art can be included (Harlow et al., Using Antibodies: A Laboratory Manual, Cold Spring Harbor Laboratory Press, 1998). In certain embodiments of the invention, such as in the HIVCON immunogen of SEQ ID NO:4, the Pk epitope tag is used. This is an epitope bound by a monoclonal antibody (mAB). The epitope is referred to either as Pk or Pk tag (from mAb clone "k") and is from the SV5 virus phosphoprotein P. The amino acid sequence of the Pk epitope is IPNPLLGLD (SEQ ID NO:6), and is the last 9 amino acids (amino acids 798-806) of SEQ ID NO:4. The additional domains can also be immunogenic in a laboratory animal (e.g., simian or murine CTL epitopes) and thereby provide an additional method of monitoring the AFP during developmental research, preclinical studies and possibly, during clinical use. When such additional immunogenic domains are used, the number of such domains should be minimized, preferably to no more than 3 or 4, to avoid interference with or competition for stimulation of HIV-specific immune responses.

In a preferred embodiment, the AFPs have a domain with at least one non-human CTL epitope that is recognized by the immune system of one or more laboratory animals, such as mice, non-human primates (including chimpanzees, rhesus macaques and other monkeys and the like), rabbits, rats, or other suitable laboratory animals. Major histocompatibility complex (MHC) molecules present these epitope peptides to T cells. For rhesus macaque (*Macaca mulata*), the MHC molecule is referred to as Mamu, for mice it is historically referred to as H-2, and for humans it is referred to as HLA. Inclusion of a non-human CTL epitope allows assessment of the quality, reproducibility, and/or stability of different batches of the AFPs using a laboratory test animal. Examples of such epitopes include the amino acid sequence STPESANL (SEQ ID NO:7) which is a Mamu-A*01-restricted epitope from simian immunodeficiency virus (SIV) tat protein that is recognized by rhesus monkey CTLs (hereinafter "the SIV tat CTL epitope"; Allen et al., (2000b) Nature 407: 386-390). Another example is SYIPSAEKI (SEQ ID NO:8) which is a murine H-2K$^d$-restricted CTL epitope from *Plasmodium berghei* and is also called the pb9 epitope (Romero et al., (1989) Nature 341: 323-326). Other suitable epitopes are known, e.g., the amino acid sequence ACTPYDINQML (SEQ ID NO:9), which contains an epitope from SIV Gag p27 recognized by rhesus macaque monkey CTLs (referred to herein as "the SIV Gag p27 epitope"). The ACTPYDINQML (SEQ ID NO:9) epitope is present in the HIVCON immunogen of SEQ ID NO:4 (amino acid positions 778-788. See FIG. 5). Another suitable epitope is CTPYDINQM (SEQ ID NO:10) (p11C, C-M)—the SIV gag p27 epitope presented to CD8 T cells by the Mamu-A*01 MHC. The CTPYDINQM (SEQ ID NO:10) epitope is present in the HIVCON immunogen of SEQ ID NO:4 (amino acid positions 779-787. See FIG. 5). Another suitable epitope has the sequence RGPGRAFVTI (SEQ ID NO:11), a murine H-2$^k$-restricted CTL epitope from HIV gp41 protein which is also known as the P18-I10 epitope, and referred to herein as "the P18-I10 epitope". The RGPGRAFVTI (SEQ ID NO:11) epitope is present in the HIVCON immunogen of SEQ ID NO:4 (amino acid positions 790-798. See FIG. 5). Suitable non-human CTL epitopes are known or can be readily determined by those of skill in the art using techniques known for identifying CTL in laboratory animals.

The AFPs can also comprise a domain that is a small tag or marker to allow for detection of expression, localization, quantification of the amount of AFP and/or purification of the AFP. Suitable tags include, but are not limited to, epitopes recognized by mAbs, such as the epitope IPNPLLGLD (SEQ ID NO:6) recognized by the Pk mAb (Hanke et al., (1992) J. Gen. Virol. 73:653-660). The IPNPLLGLD (SEQ ID NO:6) epitope is present in the HIVCON immunogen of SEQ ID NO:4 (amino acid positions 799-8-6. See FIG. 5). Other suitable tags include the epitope YPYDVPDYA (SEQ ID NO:12) recognized by HA antibody; the epitope DYKDDDDK (SEQ ID NO:13) recognized by Flag antibody; the epitope YTDIEMNRLGK (SEQ ID NO:14) recognized by the VSV-G Tag antibody and the epitope EYMPME (SEQ ID NO:15) recognized by the Glu-Glu antibody. Those of skill in the art can readily select suitable tags and markers for inclusion in an AFP.

The HIV domains of the AFPs can be contiguous within the protein. Alternatively, they can be separated by intervening amino acid sequences. The intervening amino acid sequences are generally non-HIV sequences, but can also comprise a small number of additional HIV amino acids. Intervening sequences, if present, range from 1-20 amino acids per intervening sequence domain and are preferably less than 10 amino acids, and even more preferably from 2-5 amino acids in length. For example, intervening sequences can be linkers, spacers or other sequences that optimize the expression levels of the AFPs. The intervening sequences can be used to optimize immunogenicity. Intervening sequences can also be added as a convenience to allow inclusion of useful restriction sites or to ensure that the domains of the AFPs are joined "in-frame" (e.g., for recombinantly-produced AFPs).

One example of an AFP of the invention is HIVCON. HIVCON is an AFP having 777 amino acids with 7 HIV domains (SEQ ID NO: 2, FIG. 3) and optionally, three additional domains (as in SEQ ID NO: 4, FIG. 5). A schematic diagram of HIVCON is shown in FIG. 1. The HIVCON protein, from amino to carboxyl terminus, comprises an HIV Gag domain, a first HIV Pol domain (comprising two HIV Pol subdomains), an HIV Vif domain, a second HIV Pol domain (comprising two HIV Pol subdomains), a first HIV Env domain, a third HIV Pol domain (comprising four HIV Pol subdomains), a second HIV Env domain, and optionally, the SIV p27 CTL epitope, the murine CTL epitope P10-I18, and the mAb epitope Pk. HIVCON does not contain intervening sequences. The correlation of domains for the 806 amino acids of HIVCON SEQ ID NO:4 (and SEQ ID NO:2 with the exception of the last three domains) are as follows, from N-terminus to C-terminus:

amino acids 1-135, the HIV Gag domain;
amino acids 136-393, the first HIV Pol domain (including both subdomains);
amino acids 394-421, the HIV Vif domain;
amino acids 422-484, the second HIV Pol domain (including both subdomains);
amino acids 485-521, the first HIV Env domain;
amino acids 522-723, the third HIV Pol domain (including all four subdomains);
amino acids 724-777, the second HIV Env domain;
amino acids 778-788, the SIV Gag p27 CTL epitope;
amino acids 789-798, the murine CTL epitope P18-I10; and
amino acids 799-806, the mAb epitope Pk.

The HIV domains in HIVCON are from HIV-1 Clades A-D consensus sequences. The corresponding amino acids to each domain, including each subdomain within each domain, as well as their corresponding HIV Clade, is shown in Table 1.

Another aspect of the invention relates to polypeptides and polypeptide libraries that comprise sequences that, in total, correspond to the entire length of the AFPs of the invention, advantageously SEQ ID NO: 2 or SEQ ID NO:4. Alternatively, the polypeptide or polypeptide libraries can correspond to a portion or fragment of the AFP of the present invention, advantageously SEQ ID NO: 2 or SEQ ID NO:4. Polypeptide libraries of the present invention can be used, inter alia, to delineate and further define the specific sequence or epitope of the AFP that binds to cellular receptors, such as major histocompatibility complex (MHC) Class I of the antigen-presenting cell. Polypeptide libraries can comprise pools of short amino acid sequences, which can range anywhere from a single amino acid, to as large as a hundred amino acids or longer. However, it is well-known in the art that MHC receptors recognize short amino acid sequences of approximately 8-15 amino acids in length. Therefore, it is preferable to synthesize polypeptides that range from 8 to 15 amino acids, preferably 15 successive amino acids, of SEQ ID NO: 2 or SEQ ID NO:4.

Each polypeptide can be synthesized with or without overlapping sequences. In some applications, especially when a specific sequence of an epitope is desired, the presence of overlapping sequences in the polypeptide can ensure that the entire amino acid sequence of SEQ ID NO: 2 or SEQ ID NO:4 is encompassed by the library of polypeptides. The overlapping sequences can comprise anywhere from one to 15 amino acids, depending on the length of the polypeptide. In a preferred embodiment of the present invention, each polypeptide comprises 15 successive nucleotides, wherein eleven of the amino acids are overlapping.

Synthesis of polypeptides can be either in vitro, such as by chemical peptide synthesis, solid phase synthesis, or through cell-free in vitro translation of an RNA encoding the short amino acid sequences (such as, but not limited to, rabbit reticulocyte lysate, wheat germ extract). Alternatively, the polypeptides may be synthesized recombinantly in producer cells, from a nucleic acid sequence encoding the polypeptide of interest. The polypeptides can be purified by methods known in the art, such as reverse-phase high performance liquid chromatography (HPLC), affinity chromatography, immunoprecipitation if a known epitope is contained within the polypeptide sequence and recognized by available monoclonal and/or polyclonal antibodies, ion exchange chromatography, ammonium sulfate or ethanol precipitation, acid extraction, anion or cation exchange chromatography, phosphocellulose chromatography, hydrophobic interaction chromatography, immuno-affinity chromatography, hydroxyapatite chromatography, lectin chromatography, molecular sieve chromatography, isoelectric focusing, gel electrophoresis, or combinations of these methods using monitoring techniques to follow the polypeptide at each purification step.

Each polypeptide corresponds to a specific portion or fragment of SEQ ID NO: 2 or SEQ ID NO:4, and the sum total of all of the polypeptides in the library correspond to the entire length of SEQ ID NO: 2 or SEQ ID NO:4. This is to ensure that the entire amino acid sequence of SEQ ID NO: 2 or SEQ ID NO:4 is encompassed by the polypeptides in the library, so as to "scan" the entire amino acid sequence to identify CTL epitopes of interest. The polypeptides are synthesized and pooled according to their sequence similarity. The pooled library of polypeptides can then be used to determine the specificity of the CTL response to HIV in cells or subjects receiving the AFPs of the invention, or in infected cells or infected subjects.

Accordingly, the present invention also provides a method of identifying a CTL epitope against HIV from the library of polypeptides of the present invention, in a cell expressing MHC Class I protein, comprising the steps of contacting the cell with the library of the invention, selectively binding the library with the MHC protein of the cell, isolating a polypeptide of the library that selectively binds to MHC, and sequencing the polypeptide, thereby identifying the CTL epitope.

Cells useful in the methods of the invention are antigen-presenting cells. Antigen-presenting cells express MHC Class I proteins, which are primarily involved in binding and restriction of epitopes that elicit T-lymphocyte-mediated responses to infection. MHC Class I molecules present peptides from pathogens, commonly viruses, to CD8+ CTLs, which are specialized to kill any cell that they specifically recognize. Such antigen-presenting cells include, but are not limited to, dendritic cells, macrophages, monocytes, mononuclear cells, CD8+ T-cells, and splenocytes. The cells can be derived from a subject who is infected with HIV, or can be cells infected or transfected with the virus or viral sequences in vitro. Preferably, the cells have been immunized or administered with the AFPs of the present invention. These cells that already received the AFP or other HIV sequence or virus are contacted with the library of the invention, preferably under cell or tissue culture conditions. When human cells are used, the MHC Class I receptor is human leukocyte antigen, or HLA. The invention also comprehends cells of non-human, preferably laboratory, animal species, such as, but not limited to, monkey cells, rat cells, or murine cells that are transiently or stably transfected with human MHC, or HLA. An example of a laboratory animal expressing human HLA is the HHD transgenic mouse described in Carmon, L., et al (2002) J. Clin. Invest. 110: 453-462. Different HLA/MHC subtypes and alleles can be used to further specify the nature of the interaction between the immunogenic polypeptides of the invention and the particular HLA/MHC allele that is known to be dominant in a particular population of interest. Alternatively, cells derived from many different subjects, each expressing different alleles of MHC, can be used in the methods of the invention.

The library of the present invention is then allowed to selectively bind to the MHC Class I receptor present on the cell surface, generally by addition of the library to the culture medium. Upon selective binding of a particular polypeptide of the library, the polypeptide that binds to MHC Class I is isolated and sequenced, thereby identifying the CTL epitope. Selective binding of the polypeptide of interest to the MHC Class I receptor of the cell can be monitored by flow cytometry, but also by determining the binding constant of the receptor-polypeptide interaction. This can be achieved by standard enzyme kinetic assays known in the art. Preferably flow cytometry (also known in the art as fluorescence activated cell sorting; FACS) is used. A method of using indirect FACS to measure peptide binding to cell-surface MHC receptors is described in Carmon, L., et al (2002) J. Clin. Invest. 110: 453-462. Briefly, cells that are loaded with the polypeptide libraries of the invention are incubated with anti-MHC antibodies. After washing, a secondary antibody with a fluorescent tag (i.e., fluorescein isothiocyanate, among others) is bound to the anti-MHC antibody, after which the amount of bound antibodies is measured by FACS analysis.

The resultant polypeptide of interest can be isolated by techniques known in the art, such as, but not limited to, reverse-phase HPLC, acetone precipitation, ammonium sulfate precipitation, trifluoroacetic acid precipitation, and chromatography methods discussed herein. The isolated polypeptide is then subjected to sequencing to determine the precise boundaries of the binding sequence to MHC. Sequencing methods known in the art include, without limitation, Edman degradation (also known as N-terminal sequencing), tandem mass spectrometry, and matrix-assisted laser desorption ionization (MALDI).

The invention also comprehends high-throughput automation of the methods to identify CTL epitopes using the libraries of the present invention. The library or libraries of polypeptides can be synthesized on a solid support, such as cellulose or on a silicon array, for subsequent detection of anti-MHC antibody binding by immunofluorescence. The relative fluorescence corresponding to binding of the polypeptide to the MHC Class I receptor can be measured in an automated fashion, allowing for efficient screening of hundreds or thousands of polypeptide sequences for suitable CTL epitopes.

The immunogenic polypeptides of the invention can also be used as an immunogen or antigen to elicit humoral responses to produce, for example, monoclonal and polyclonal antibodies in host animals against the AFPs of the invention. Such host animals may include but are not limited to rabbits, mice, and rats. Various adjuvants may be used to increase the immunologic response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*Bacille Calmette-Guerin*) and *Corynebacterium parvum*.

Another aspect of the invention relates to nucleic acid molecules encoding AFPs of the invention. "Nucleic acid molecules" or "nucleic acid" as used herein means any deoxyribonucleic acid (DNA) or ribonucleic acid (RNA), including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex. The nucleic acid molecules of the invention have a nucleotide sequence that encodes the AFPs and can be designed to employ codons that are used in highly-expressed genes of the subject in which the AFP gene is expressed (or to be expressed). Typically, the nucleic acid has the entire coding sequence of the AFP as a single open reading frame (ORF), that is, without introns.

Different cells vary in their usage of particular codons. This codon bias corresponds to a bias in the relative abundance of particular transfer RNAs (tRNAs) in a particular cell type. Many viruses, including HIV and other lentiviruses, use a large number of rare codons and, by altering these to correspond to commonly used mammalian codons, enhanced expression of the immunogen in cells can be achieved. By altering the codons in the sequence to match with the relative abundance of corresponding tRNAs, it is possible to increase expression of the AFP. Similarly, it is possible to decrease expression of the AFP by deliberately choosing codons for which the corresponding tRNAs are known to be rare in a particular cell type. Thus, an additional degree of translational control is available. The overall effect of codon optimization can be, for example, an increase in viral titer, i.e. if the AFP is expressed from a viral vector, and improved safety in a subject. Codon usage tables are known in the art for mammalian cells, as well as for a variety of other organisms.

In a preferred embodiment, the codons encoding the AFP are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the AFPs in human cells. In other embodiments, for example, when the AFP is expressed in bacteria, yeast or other expression system, the codon usage pattern is altered to represent the codon bias for highly expressed genes in the organism in which the AFP is being expressed. Codon usage patterns are known in the literature for highly expressed genes of many species (e.g., Nakamura et al., (1996) Nucl. Acids Res. 24: 214-215; Wang et al, (1998) Mol. Biotechnol. 10: 103-106; McEwan et al. (1998) Biotechniques 24:131-136).

The nucleic acid sequence for HIVCON is provided, in alternative forms with (SEQ ID NO:3) and without (SEQ ID NO: 1 or SEQ ID NO: 5) nucleotides encoding the last three additional domains. In one embodiment of the invention, the nucleic acid of the invention comprises the nucleotides encoding the HIVCON coding sequence provided in SEQ ID NO: 1 or SEQ ID NO:5 (beginning at nucleotide 1 of SEQ ID NO: 1 or nucleotide 30 of SEQ ID NO:5 and continuing to the stop codon). In another embodiment of the invention, the nucleic acid of the invention comprises the nucleotides encoding the HIVCON coding sequence provided in SEQ ID NO: 3 which includes the nucleotides including three additional epitopes (beginning at nucleotide 1 of SEQ ID NO: 3 and continuing to the stop codon). In another embodiment of the invention, the nucleic acids of the invention consists essentially of the sequences of SEQ ID NO: 1, SEQ ID NO: 3, or SEQ ID NO: 5, as shown in FIGS. 2, 4, and 6, respectively.

Nucleic acid molecules encoding the AFPs of the invention can be incorporated into expression vectors and used to immunize subjects or used to express the protein in vitro, typically for protein production or for RNA production.

As used herein, a "vector" is a tool that allows or facilitates the transfer of an entity from one environment to another. By way of example, some vectors used in recombinant DNA techniques allow entities, such as a segment of DNA (such as a heterologous DNA or cDNA segment), to be transferred into a target cell. The present invention comprehends recombinant vectors that can include viral vectors, bacterial vectors, protozoan vectors, DNA plasmid vectors, or recombinants thereof.

With respect to exogenous DNA for expression in a vector (e.g., encoding an epitope of interest and/or an antigen and/or a therapeutic) and documents providing such exogenous DNA, as well as with respect to the expression of transcription and/or translation factors for enhancing expression of nucleic acid molecules, and as to terms such as "epitope of interest", "therapeutic", "immune response", "immunological response", "protective immune response", "immunological composition", "immunogenic composition", and "vaccine composition", inter alia, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990,091 and WO 98/00166 and WO 99/60164 and documents cited therein and documents or record in the prosecution of that patent and those PCT applications, and other documents cited herein or otherwise incorporated herein by reference, can be consulted in the practice of this invention; and, all exogenous nucleic acid molecules, promoters, and vectors cited therein can be used in the practice of this invention. In this regard, mention is also made of U.S. Pat. Nos. 6,706,693; 6,716,823; 6,348,450; U.S. patent application Ser. Nos. 10/424,409; 10/052,323; 10/116, 963; 10/346,021; and WO9908713, published Feb. 25, 1999, from PCT/US98/16739.

Expression vectors are well-known in the art and for the present invention share the common feature of having a protein coding sequence "operably linked" to regulatory or nucleic acid control sequences that direct transcription and translation of the protein. As used herein, an AFP coding sequence and a nucleic acid control sequence are said to be "operably linked" when they are covalently linked in such a way as to place the expression or transcription and/or translation of the AFP coding sequence under the influence or control of the nucleic acid control sequence. A "nucleic acid control sequence" can be any nucleic acid element, such as, but not limited to promoters, enhancers, IRES, introns, and other elements described herein that direct the expression of a nucleic acid sequence or coding sequence that is operably linked thereto. Two DNA sequences are said to be operably linked if induction of a nucleic acid control sequence, such as a promoter, in the 5' gene expression sequence results in the transcription of the AFP sequence and if the nature of the linkage between the two DNA sequences does not (1) result in the introduction of a frame-shift mutation, (2) interfere with the ability of the promoter region to direct the transcription of the antigen sequence, or (3) interfere with the ability of the corresponding RNA transcript to be translated into a protein. Thus, a nucleic acid control sequence would be operably linked to an AFP nucleic acid sequence if the nucleic acid control sequence were capable of effecting transcription of that AFP nucleic acid sequence, such that the resulting transcript is translated into the desired protein or polypeptide.

The nucleic acid control sequences, such as promoters, enhancers and the like, in the expression vectors are often heterologous with respect to the host. The term "promoter" will be used here to refer to a group of transcriptional control modules that are clustered around the initiation site for RNA polymerase II and that when operationally linked to an AFP lead to the expression of the AFP. Promoters are generally composed of discrete functional modules, each consisting of approximately 7-20 bp of DNA, and containing one or more recognition sites for transcriptional activator proteins. At least one module in the promoter may function to position the transcription start site while other modules may regulate the frequency of transcriptional initiation. "Enhancers" may be described as genetic elements that increase transcription from a promoter located at distance in the same DNA molecule. Much like promoters, enhancers may be composed of many individual modules, each of which binds to one or more transcriptional proteins. While both promoter and enhancers have the same general function of activating transcription in the cell, there is clear distinction between their functions. Enhancers, by definition, stimulate transcription at a distance and need not direct transcriptional initiation at a particular site. Modules of a promoter, on the other hand, must direct transcriptional initiation from a particular site in a particular orientation.

The expression of the AFP nucleotide sequence in the expression vector can thus be under the control of a constitutive promoter or of an inducible promoter, which initiates transcription only when the host cell is exposed to some particular external stimulus, such as, without limitation, antibiotics such as tetracycline, hormones such as ecdysone, or heavy metals. In the case of a multicellular organism, such as an animal, the promoter can also be specific to a particular tissue or organ. Various promoters and enhancer elements that may be used in the construction of vectors as various embodiments of the invention are discussed in U.S. Pat. No. 6,835,866, the contents of which is hereby incorporated by reference Furthermore, any promoter/enhancer combinations as per the Eukaryotic Promoter Database (EPDB) may be used to drive the expression of AFP of the invention.

Expression vectors are known and available for many organisms, including bacteria, fungi, yeast, animals (including mammals and particularly humans), birds, insects, plants and the like. Animals include, but are not limited to, mammals (humans, primates, etc.), commercial or farm animals (fish, chickens, cows, cattle, pigs, sheep, goats, turkeys, etc.), research animals (mice, rats, rabbits, etc.) and pets (dogs, cats, parakeets and other pet birds, fish, etc.).

Accordingly, expression vectors of the present invention have the coding sequence for an AFP of the invention operably linked to transcriptional and/or translational nucleic acid control sequences, depending on whether protein is being expressed or RNA is being produced. The expression vectors of the invention are useful to achieve expression of the AFP or a nucleic acid encoding the AFP in a particular host cell, including production of DNA or RNA encoding the AFP. Similarly, the expression vectors of the invention include plasmid, liposomal, microorganism and viral vectors useful to deliver the AFP (as protein or nucleic acid) to a host subject.

Expression vectors of the invention include plasmids, viral vectors, bacterial vectors, protozoal vectors, insect vectors, yeast vectors, mammalian cell vectors and the like. Whether the expression vector is capable of replication or self-amplification depends on the vector employed and the reason for its selection. Such characteristics can be readily determined by the skilled artisan when considering the requirements for expressing the AFP under the identified circumstances.

Expression vectors of the invention include those used for the expression of the AFPs in a laboratory animal, a mammal or, preferably, a human subject. These vectors are particularly useful for immunizing the animal, mammal or human subject to stimulate an immune response against the encoded AFP. Expression vectors useful in this regard include bacterial vectors, viral vectors, plasmids and liposomal formulations using nucleic acid (from plasmids or viruses). For bacterial vectors, the preferred vectors are attenuated to prevent proliferation of the bacterial carrier in the host or to only allowed self-limiting proliferation that will not lead to disease or other detrimental pathological effect. Killed bacteria are also useful. Viral vectors are preferably attenuated or replication-defective, again to provide safety of use in the host. Plasmids, when used, can lack an origin of replication that functions in humans.

In certain preferred embodiments, the pTH or pTHr vectors are used. The construction of the pTH vector is described in Hanke et al, 1998 Vaccine 16, 426-435. pTH contains an expression efficient enhancer/promoter/intron A cassette of the human cytomegalovirus (hCMV) strain AD169 genome (Whittle et al, 1987 Protein Eng. 1, 499-505; Bebbington 1991 Methods 2, 136-145). The promoter region is followed by the pRc/CMV (Invitrogen)-derived polylinker and polyadenylation signal of the bovine growth hormone gene. The beta-lactamase gene conferring ampicillin resistance to transformed bacteria and prokaryotic origin of double-stranded DNA replication ColE1 are both derived from plasmid pUC19. The pTH vector does not contain an origin for replication in mammalian cells.

The pTHr vector is derived from pTH by deletion of the beta-lactamase/ampicillin resistance gene. It is propagated in bacteria using the repressor-titration system developed by Cobra Pharmaceuticals Ltd. (Keele, UK), which selects plasmid-carrying bacteria without the need for the presence of an antibiotic-resistance gene on the plasmid (See U.S. Pat. No. 5,972,708, and Williams et al, 1998 Nucl. Acids Res. 26, 2120-2124). The pTHr vector is particularly well suited to use in humans because it does not introduce into the human vaccinee large numbers of copies of an antibiotic resistance gene. Therefore, in one embodiment the nucleotides sequences encoding the HIVCON immunogens of the present invention are incorporated into the pTHr vector for administration of the vector to humans as a DNA vaccine.

Any plasmid vector safe for use in humans, mammals or laboratory animals is contemplated for use in accordance with the present invention, as well as any plasmid vector useful for protein purification from prokaryotic or eukaryotic expression systems.

Viral expression vectors are well known to those skilled in the art and include, for example, viruses such as adenoviruses, adeno-associated viruses (AAV), alphaviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected host humans or have been modified to render them non-pathogenic in the selected host. For example, replication-defective adenoviruses and alphaviruses are well known and can be used as gene delivery vectors. A preferred viral vector is MVA, which is a highly attenuated vaccinia strain which fails to replicate in most mammalian cells (Mayr et al., (1975) Infection 105:6-14). AFPs can be cloned into many sites of the MVA and used to immunize a subject, especially a human subject, and generate an HIV-specific immune response against the encoded AFP. Useful MVA cloning sites, for example include the thymidine kinase and deletion III loci (Chakrabarti et al., (1985) Mol. Cell. Biol. 5: 3403-3409; Meyer, H. et al (1991) J. Gen. Virol. 72: 1031-8; Altenburger, W. et al (1989) Arch. Virol. 105(1-2): 15-27).

It must be noted that certain poxviruses, such as MVA, NYVAC, and avipox, can only productively replicate in or be passaged through avian species or avian cell lines such as, for example, chicken embryonic fibroblasts. The recombinant poxviruses harvested from avian host cells, when inoculated into a non-avian vertebrate, such as a mammal, in a manner analogous to the inoculation of mammals by vaccinia virus, produce an inoculation lesion without productive replication of the avipox virus. Despite the failure of certain poxviruses, such as MVA, NYVAC, and avipox, to productively replicate in such an inoculated non-avian vertebrate, sufficient expression of the virus occurs so that the inoculated animal responds immunologically to the antigenic determinants of the recombinant poxvirus and also to the antigenic determinants encoded in exogenous genes therein. Thus, in one embodiment, when certain poxviruses or viral vectors (as disclosed above) are used, chicken embryonic fibroblasts are preferred as the cell permissive for viral vector replication.

The recombinant viral vectors and recombinant viruses can contain promoters that are operably linked to the AFPs of the present invention. When contained in a poxviral vector, the promoter is advantageously of poxviral origin, which may be, in particular, the promoter 7.5K of the vaccinia virus, 13L poxviral promoter, 11K poxviral promoter (U.S. Pat. No. 5,017,487), 42K poxviral promoter, H6 poxviral promoter, thymidine kinase poxviral promoter, E3L poxviral promoter, K3L poxviral promoter, or a synthetic poxviral promoter. The promoter can advantageously be an "early" promoter. An "early" promoter is known in the art and is defined as a promoter that drives expression of a gene that is rapidly and transiently expressed in the absence of de novo protein synthesis. The promoter can also be a "strong" or "weak" promoter. The terms "strong promoter" and "weak promoter" are known in the art and can be defined by the relative frequency of transcription initiation (times per minute) at the promoter. A "strong" or "weak" promoter can also be defined by its affinity to poxviral RNA polymerase.

The invention also provides for viral promoters that are mutated. Without being bound by theory, it is believed that high levels of expression of potentially toxic heterologous sequences expressed from viral vectors can preclude formation of stable viral recombinants. Therefore, the present invention also comprehends the use of a mutated viral promoter, such as, for example, a mutated H6 poxviral promoter useful when poxvirus recombinants are desired, such that the expression levels of the AFP sequences expressed from viral vectors are decreased compared with expression levels of the heterologous sequences under a wild type promoter. The mutated H6 promoter can be considered a weak promoter.

The mutated promoters can contain point mutations. The invention can also employ promoters other than H6, which contain point mutations that reduce their frequency of transcription initiation compared with the wild type promoter. In addition, other types of mutated promoters are suitable for use in the instant invention (see also Davison, A. et al (1989) J. Mol. Biol. 210: 749-769; Taylor J. et al., Vaccine, 1988, 6, 504-508; Guo P. et al. J. Virol., 1989, 63, 4189-4198; Perkus M. et al., J. Virol., 1989, 63, 3829-3836).

The viral vectors or viruses of the present invention can further comprise additional sequences to control transcription and translation of the AFPs. For example, when contained in a poxviral vector, such sequences can comprise a T5NT termination recognition signal, which can be recognized by poxviral RNA polymerase for termination of early RNA transcription.

The AFPs of the invention can also be delivered as adenovirus recombinants, which include E1-defective or deleted, E3-defective or deleted, and/or E4-defective or deleted adenovirus vectors, or the "gutless" adenovirus vector in which all viral genes are deleted. The adenovirus vectors can comprise mutations in E1, E3, or E4 genes, or deletions in these or all adenoviral genes. The E1 mutation raises the safety margin of the vector because E1-defective adenovirus mutants are said to be replication-defective in non-permissive cells, and are, at the very least, highly attenuated. The E3 mutation enhances the immunogenicity of the antigen by disrupting the mechanism whereby adenovirus down-regulates MHC class I molecules. The E4 mutation reduces the immunogenicity of the adenovirus vector by suppressing the late gene expression, thus may allow repeated re-vaccination utilizing the same vector. The present invention comprehends adenovirus vectors that are deleted or mutated in E1, E3, E4, E1 and E3, and E1 and E4. The present invention also comprehends adenoviruses of the human Ad5 strain.

The "gutless" adenovirus vector can also be used to express AFPs of the present invention. Its replication requires a helper virus and a special human 293 cell line expressing both E1a and Cre, a condition that does not exist in natural environment; the vector is deprived of all viral genes, thus the vector as a vaccine carrier is non-immunogenic and may be inoculated multiple times for re-vaccination. The "gutless" adenovirus vector also contains 36 kb space for accommodating transgenes, thus allowing co-delivery of a large number of heterologous genes into cells. Specific sequence motifs such as the RGD motif may be inserted into the H-I loop of an adenovirus vector to enhance its infectivity. This sequence has been shown to be essential for the interaction of certain extracellular matrix and adhesion proteins with a superfamily of cell-surface receptors called integrins. Insertion of the RGD motif may be advantageously useful in immunocompromised subjects. An adenovirus recombinant is constructed by cloning specific transgenes or fragments of transgenes into any of the adenovirus vectors such as those described above.

Other viral vectors useful for delivering the AFPs include alphavirus vectors, particularly those based on the replicons of Semliki Forest Virus (SFV), Sindbis virus and Venezuelan Equine Encephalitis virus (VEE) (see, e.g, Smerdou et al., (2000) Gene. Ther. Regul. 1:33-63; Lundstrom et al., (2002) Technol. Cancer Res. Treat. 1: 83-88; Hanke 2003). Alphavirus replicons are useful expression vectors and can refer to RNA or DNA comprising those portions of the alphavirus genomic RNA essential for transcription and export of a primary RNA transcript from the cell nucleus to the cytoplasm, for cytoplasmic amplification of the transported RNA and for RNA expression of a heterologous nucleic acid sequence, such as the AFPs of the present invention. Thus, the replicon encodes and expresses those non-structural proteins needed for cytoplasmic amplification of the alphavirus RNA and expression of the subgenomic RNA, as well as an AFP of the invention. It is further preferable that the alphavirus replicon cannot be encapsidated to produce alphavirus particles or virions. This can be achieved by replicons, which lack one or more of the alphavirus structural genes, and preferably all of the structural genes, such as occurs with a one-helper or two-helper alphavirus vector system. In a preferred embodiment, alphavirus replicons are capable of being transcribed from a eukaryotic expression cassette and processed into RNA molecules with authentic alphavirus-like 5' and 3' ends.

Alphavirus replicons and expression vectors containing them are well known in the art and many vectors containing a wide range of alphavirus replicons have been described. Examples of such replicons can be found, e.g., in U.S. Pat. Nos. 5,739,026; 5,766,602; 5,789,245; 5,792,462; 5,814,482; 5,843,723; and 6,531,313; and in Polo et al., (1998) Nature Biotechnol. 16: 517-518 and Berglund et al., (1998) Nature Biotechnol. 16: 562-565. Alphavirus replicons can be prepared from any alphavirus or any mixture of alphavirus nucleic acid sequences. In this regard, the preferred alphavirus replicons are derived from Sindbis virus, SFV, VEE or Ross River virus.

Other viral expression vectors include flaviviruses (WO02/072835), such as yellow fever virus, Dengue virus and Japanese encephalitis virus, poxviruses such as vaccinia virus (U.S. Pat. No. 5,505,941), avipoxviruses such as fowlpox virus (Kent) and canarypox virus (Clements-Mann et al., (1998) J. Infect. Dis. 177: 1230-1246; Egan et al., (1995) J. Infect. Dis. 171: 1623-1627; U.S. Pat. No. 6,340,462), including attenuated avipoxviruses such as TROVAC (U.S. Pat. No. 5,766,599) and ALVAC (U.S. Pat. No. 7,756,103), picornaviruses such as poliovirus (U.S. Pat. Nos. 6,780,618; 6,255,104; WO92/014489) and rhinovirus, herpesviruses (WO87/000862; WO 87/04463; WO97/014808) such as Varicella zoster virus (VZV; WO97/004804), NYVAC (New York vaccinia virus with 18 gene deletions selected to decrease pathogenicity) (Hel et al., (2001) J. Immunol. 167: 7180-7191; U.S. Pat. Nos. 5,494,807; 5,762,938; 5,364,773); Adenovirus (AdV; WO95/02697; WO95/11984; WO95/27071; WO95/34671), adeno-associated virus (AAV; U.S. Pat. Nos. 4,797,368; 5,474,935), influenza virus (WO03/068923; WO02/008434; WO00/053786), cauliflower mosaic virus (U.S. Pat. No. 4,407,956), tobacco mosaic virus (TMV) (Palmer et al, (1999) Arch. Virol. 144: 1345-1360; WO93/003161) and NS1 tubules of bluetongue virus (Adler et al., (1998) Med. Microbial. Immunol. (Berl) 187: 91-96). Many of these vectors are readily available and conditions applicable for their use are well-known to the skilled artisan.

Expression vectors of the invention also include bacterial expression vectors for administration to a laboratory animal, mammal or human subject. Such bacterial expression vectors (attenuated, invasive bacteria) are bacteria that contain a plasmid or an expression cassette encoding an AFP of the invention. The expression cassette can drive expression in the bacteria or in eukaryotic cells. In the former, expression is achieved before introducing the bacterial cells into the host, whereas in the latter, expression occurs in the host and can be driven by the host cellular machinery. U.S. Pat. Nos. 5,877,159; 6,150,170; 6,500,419 and 6,531,313 describe bacterial vectors that invade animal cells without establishing a productive infection or causing disease and thus permit the introduction of a expression cassette encoding an AFP into a eukaryotic cell to obtain expression of the AFP.

Suitable bacterial expression vectors include *Mycobacterium bovis*, *Bacillus Calmette Guerin* (BCG), and attenuated strains of *Salmonella* (especially the "double aro" mutants of *Salmonella* that are being developed as vaccines for diarrheal diseases), *Shigella* (see Shata et al., (2000) Mol. Med. Today 6: 66-71), *Neisseria* and *Listeria monocytogenes*. Preferred *Salmonella typhi* strains include CVD908Δasd, CVD908ΔhtraA and CVD915. The CVD908Δasd *Salmonella* strain derives from CVD908 (Tacket et al., (1992) Vaccine 10: 443-446) by deletion of the asd gene that encodes the aspartate b-semialdehyde dehydrogenase (asd), an enzyme necessary for the synthesis of diaminopimelic acid (DAP) from aspartate. CVD908ΔhtrA is a *S. typhi* strain with the htrA gene deleted. This mutation knocks out a heat shock gene that further attenuates the strain (Tacket et al., (1997) Infect. Immunol. 65:452-456). CVD915 is an attenuated *S. typhi* strain that has a deletion of the guaBA locus, resulting in its attenuation (Pasetti et al., Clin. Immunol. 92:76-89, 1999). This strain has been shown to be excellent for the delivery of DNA vaccines in animal studies. A preferred *Shigella* strain is *S. flexneri* CVD 1207. This strain has deletions of the sen, set, virG and guaBA genes that renders it well attenuated while preserving its immunogenicity (Kotloff et al., Infect. Immunol. 68:1034-1039, 2000).

Expression vectors of the invention are also used for preparation and purification of the AFPs of the invention. Vectors in this regard are typically used in bacteria, yeast, insect or mammalian cells. The nucleic acid control sequences directing expression of the nucleic acid molecule encoding the AFP are chosen based on the host cell (e.g., bacterial, yeast, insect or mammalian cells) from which the expression is being directed. Appropriate nucleic acid control sequences for a particular host cell and expression vector are well known. The expression vectors containing the AFP can be introduced into these cells by well-known methods in the art, which depend, inter alia, on the type of cell and whether the duration of expression is transient or stable. For example, calcium chloride transfection is commonly utilized for prokaryotic cells, whereas calcium phosphate treatment, lipofection, microinjection, particle bombardment, or electroporation is used for many eukaryotic cells. Any transfection, infection, transformation or suitable technique for introducing an expression vector into a cell, whether prokaryotic or eukaryotic, known to the skilled artisan can be used.

There are numerous *Escherichia coli* vectors and cells known to one of ordinary skill in the art that are useful for expression of the AFPs of the invention. Other microbial hosts suitable for use include bacilli, such as *Bacillus subtilis*, and other enterobacteria, such as *Salmonella, Serratia*, as well as various *Pseudomonas* species. These prokaryotic hosts can support expression vectors, which typically contain expression control sequences operable primarily in the host cell. Any number of a variety of well-known promoters can be present, such as the lactose promoter system, a tryptophan (Trp) promoter system, a β-lactamase promoter system, or a promoter system from phage λ. The promoters will typically control expression, optionally with an operator sequence and have ribosome binding site sequences for example, for initiating and completing transcription and translation. If necessary, an amino-terminal methionine can be provided by insertion of a Met codon 5' and in-frame with the protein. Among vectors preferred for use in bacteria include pQE70, pQE60 and pQE9, available from QIAGEN, Inc.; pBluescript vectors, Phagescript™ vectors, pNH8A, pNH16a, pNF118A, pNH46A, available from Stratagene Cloning Systems, Inc.; and ptrc99a, pKK223-3, pKK233-3, pDR540, pRIT5 available from Pharmacia Biotech, Inc. Other expression vector systems are based on β-galactosidase (p-gal; pEX), maltose binding protein (pMAL) and glutathione S-transferase (pGST) (see e.g., Smith, (1988) Gene 67: 31-40 and Abath. (1990) Peptide Research 3: 167-168).

Yeast cells can also be used to direct expression of the AFPs of the invention. There are several advantages to yeast expression systems that make use of the yeast system desirable in certain circumstances, including providing disulfide pairing, post-translational modifications, protein secretion and easy isolation when protease cleavage site is inserted upstream of from the AFP coding sequence. The *Saccharomyces cerevisiae* pre-pro-α-factor leader region (encoded by the MFa-I gene) is routinely used to direct protein secretion from yeast (Brake et al., (1984) Proc. Natl. Acad. Sci. USA 82: 4642-

4646; U.S. Pat. No. 4,870,008). The leader region of pre-pro-α-factor contains a signal peptide and a pro-segment, which includes a recognition sequence for a yeast protease encoded by the KEX2 gene. This enzyme cleaves the precursor protein on the carboxyl side of a Lys-Arg dipeptide cleavage-signal sequence. The AFP coding sequence can be fused in-frame to the pre-pro-α-factor leader region. This construct can then be put under the control of a strong transcriptional promoter, such as the alcohol dehydrogenase I promoter, actin, or a glycolytic promoter. Alternatively, inducible promoters can also be used, such as those dependent on the presence or absence of metal ions (i.e., CUP1 promoter, also known as metallothionein promoter), glucose, galactose (i.e., GAL1, GAL10), or other sugars. The fusion protein coding sequence can be followed by a translation termination codon, which can be followed by transcription termination signals. Vectors useful for expression in yeast include, without limitation, the 2μ circle plasmid (Broach, J. R. et al, (1979) Gene 8(1): 121-33) and the centromeric plasmid (Hsiao, C. L. and Carbon, J. (1981) Proc. Natl. Acad. Sci. 78(6): 3760-4).

Efficient post-translational modification and expression of recombinant proteins can also be achieved in Baculovirus systems in insect cells ("Baculovirus Expression Protocols," Humana Press Inc.; WO92/005264). These systems are well known in the art.

Mammalian cells are useful to express and purify the AFPs of the invention, especially when the protein is purified for administration to mammalian subjects. Vectors useful for the expression of proteins in mammalian cells often have strong viral promoters to direct expression and can also include other sequences that are useful for directing expression in human cells, such as enhancers, polyadenylation signals, and other signal sequences for promoting transcription, translation, i.e., internal ribosomal entry sites (IRES) and/or the processing of the AFPs of the invention. In certain embodiments of the invention where the use of IRES elements may be necessary, IRES elements may be derived from viruses, such as the picornavirus family (polio and encephalomyocarditis) IRES and the hepatitis C virus IRES, or from mammalian mRNA such as the mammalian BiP IRES. Alternatively or additionally, the plasmid in the DNA vaccine or immunogenic composition can further contain and express in a subject host cell a nucleotide sequence encoding a heterologous tPA signal sequence such as human tPA and/or a stabilizing intron, such as intron II of the rabbit β-globin gene.

Depending on the vector, selectable markers encoding antibiotic resistance may be present when used for in vitro purification, such as, but not limited to, ampicillin, tetracycline, neomycin, zeocin, kanamycin, bleomycin, hygromycin, chloramphenicol, among others. Selection systems that do not use antibiotic resistance genes can also be used in the expression vector and mammalian host system. Promoter sequences that can be used to direct expression of the AFPs include, but are not limited to, strong viral promoters, such as the promoter from human cytomegalovirus (CMV), the promoter from the thymidine kinase gene of herpes simplex virus (HSV), promoters from adenoviruses such as the Adenovirus 5E2 Collagenase promoter, β-actin promoter, Muscle Creatine Kinase promoter and composite promoters such as the EF-1a/HTLV promoter (InVitrogen) and the ferritin composite promoters comprised of the FerH or FerL core promoters (InVitrogen) among others. Among preferred eukaryotic expression vectors are pWLNEO, pSV2CAT, pOG44, pXTI and pSG available from Stratagene; and pSVK3, pBPV, pMSG and pSVL available from Pharmacia. The AFP coding sequence can be introduced into a mammalian cell line capable of synthesizing intact proteins have been developed in the art and include, but are not limited to, CHO, COS, 293, 293T, HeLa, NIH 3T3, Jurkat, myeloma and PER.C6 cell lines. Presence of the expression vector-derived RNA in the transfected cells can be confirmed by Northern blot analysis and production of a cDNA or opposite strand RNA corresponding to the protein coding sequence can be confirmed by Southern and Northern blot analysis, respectively.

Cell transformation techniques and gene delivery methods (such as those for in vivo use to deliver genes) are well known in the art. Any such technique can be used to deliver a nucleic acid or expression vector encoding an AFP of the invention to a cell or subject, respectively.

The AFPs of the invention can be purified from bacterial, yeast, insect or mammalian cells using techniques well-known in the art. For example, the AFPs can be purified or concentrated using ammonium sulfate or ethanol precipitation, acid extraction, anion or cation exchange chromatography, phosphocellulose chromatography, hydrophobic interaction chromatography, affinity chromatography, immunoaffinity chromatography, hydroxyapatite chromatography, lectin chromatography, molecular sieve chromatography, isoelectric focusing, gel electrophoresis, combinations of these methods using monitoring techniques to follow the distribution of the AFP at each purification step as well as the purity of the AFP. Some or all of the foregoing purification steps, in various combinations or with other known methods, can also be employed to provide substantially purified, isolated AFPs of the invention. If the AFP contains an epitope recognized by a monoclonal or polyclonal antibody, then immunoaffinity purification can be used alone or in conjunction with the above techniques. For immunoaffinity chromatography, the AFP (or a cellular extract or other mixture containing the AFP) can be purified by passage through a column containing a resin, which has bound thereto antibodies specific for the antigenic peptide. Immunoaffinity purification can also be conducted in batches when the affinity reagent is bound to a solid support. Such techniques are well known in the art.

IV. Immunogenic Compositions and Adjuvants

In yet another aspect, the invention provides an immunogenic composition comprising the AFPs, nucleic acids or expression vectors of the invention in admixture with a pharmaceutically acceptable carrier. Such carriers are also acceptable for immunological use. The immunogenic compositions of the invention are useful to stimulate an immune response against HIV as one or more components of a prophylactic or therapeutic vaccine against HIV for the prevention, amelioration or treatment of AIDS. The nucleic acids and vectors of the invention are particularly useful for providing genetic vaccines, i.e. vaccines for delivering the nucleic acids encoding the AFPs of the present invention to a subject such as a human, such that the AFPS are then expressed in the subject to elicit an immune response.

The compositions of the invention may be injectable suspensions, solutions, sprays, syrups or elixirs. To prepare such a composition, an AFP, nucleic acid or expression vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants include, but are not limited to mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et al (2002) Vaccine 20(29-30): 3498-508), JuvaVax™ (U.S. Pat. No. 6,693, 086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057, 540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689, 338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline.

Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the AFP of the invention or on separate expression vectors.

Cytokines that may be used in the present invention include, but are not limited to, granulocyte colony stimulating factor (G-CSF), granulocyte/macrophage colony stimulating factor (GM-CSF), interferon α (IFN α), interferon β (IFN β), interferon γ, (IFN γ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNF α), tumor necrosis factor β (TNF β), and transforming growth factor β (TGF β). It is understood that cytokines can be co-administered and/or sequentially administered with the immunogenic or vaccine composition of the present invention. Thus, for instance, a virus propagated in the instant invention can contain an exogenous nucleic acid molecule and express in vivo a suitable cytokine, e.g., a cytokine matched to this host to be vaccinated or in which an immunological response is to be elicited (for instance, an human cytokine for compositions to be administered to humans).

The immunogenic compositions can be designed to introduce the AFP, nucleic acid or expression vector to a desired site of action and release it at an appropriate and controllable rate. Methods of preparing controlled-release formulation are known in the art. For example, controlled release preparations can be produced by the use of polymers to complex or absorb the immunogen and/or immunogenic composition. A controlled-release formulations can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the AFP, nucleic acids and expression vectors of the invention (collectively, the immunogens) in the immunogenic composition of the invention can be readily determined by those of skill in the art. For example, the dosage of the immunogens can vary depending on the route of administration and the size of the subject. A suitable dose of AFP of the invention can range from about 1-10 μg to about 5000 mg, and is typically from about 500 pg to about 100 mg, depending inter alia on the molecular weight of the AFP, the route of delivery, the delivery means and the body mass of the recipient. A suitable dose of nucleic acid of the invention can range from about 1 μg to about 100 mg, and more typically from about 10-100 μg to about 1-10 mg again depending, inter alia, on the factors assessed for protein delivery, as well as the size of the nucleic acid molecule. The dosages for delivery of expression vectors of the invention depends additionally on the nature of the expression vector. When the vector is an RNA or DNA molecule (including plasmids or a plasmid incorporated in a lipid or other delivery particle), then the amount of expression vector in a dosage is similar to that of the nucleic acids of the invention. The dosage for bacterial expression vectors is conveniently characterized according to colony forming units (cfu). The dose will preferably range from about $10^4$ to about $10^{10}$ cfu and more preferably from about $10^6$ to about $10^{10}$ cfu, as well as from about $10^8$ to about $10^9$ cfu. The dosage for viral expression vectors depends on the nature of the vector, e.g., whether the vector is an alphavirus, an adenovirus, AAV, a poxvirus, a retrovirus and the like. Any of these doses can be calculated on a unit dosage basis or as an amount per kilogram body weight of the subject.

Doses for administering viral vectors are well known and can be determined by those of skill in the art if needed. By way of example, when the agent is a viral vector, such as a replication-defective adenovirus, the dosage can range from about $10^6$ to about $10^{12}$ plaque forming units (pfu), and is preferably between about $10^8$ to about $10^{10}$ pfu. For stable and efficient transduction using a recombinant AAV, the dosage can be from about $1\times10^5$ IU (infectious units) of AAV per gram body weight to about $1\times10^9$ IU AAV per gram body weight, and preferably from about $1\times10^6$ IU AAV per gram body weight to about $1\times10^7$ IU AAV per gram body weight. For poxviruses and MVA, dosages ranging from about $10^5$ to about $10^{10}$ pfu, are useful; dosages of about $10^7$ to about $10^8$ pfu are often used.

Other suitable doses can be determined by those of skill in the art. To determine appropriate doses, those of skill in the art can measure the immune response of subjects by conventional immunological techniques and adjust the dosages as appropriate. Such techniques include but are not limited to, e.g., chromium release assay, tetramer binding assays, IFN-γ ELISPOT assays and intracellular cytokine assays as well as other immunological detection assays, e.g., as detailed in Harlow.

The present invention provides methods for expressing an AFP of the invention in animal cells by introducing an expression vector of the invention into the animal cells and culturing those cells under conditions sufficient to express the AFP. The expression vector can be introduced by any appropriate method including, but not limited to, transfection, transformation, microinjection, infection, electroporation, particle bombardment and the like. Such techniques are standard in the art. After introducing the expression vector, the cells are maintained under the appropriate culture conditions (i.e., for a time and at the appropriate conditions) to maintain cell viability at least until the AFP is expressed. In some instances, for example with alphavirus replicon vectors, expression of the AFP includes production of an RNA molecule encoding the AFP.

In addition, the invention provides methods for introducing and expressing an AFP of the invention in an animal by delivering an expression vector of the invention in to the animal and thereby obtaining expression of the AFP in the animal. Any delivery method can be used including parenteral, subcutaneous, epicutaneous, oral, peroral, intramuscular, intravenous, intradermal, intranasal, mucosal, topical or other delivery method, such as the particle bombardment method by Powderject (a needle-less delivery system to the skin that is actuated by helium gas). Such techniques are well known to those of skill in the art. The expression vectors can be formulated as needed to improve stability and delivery efficiency. Once the expression vector is delivered, the ORF of the AFP is transcribed (if needed) and translated to express the encoded AFP. One of skill in the art is familiar with methods of in vitro and in vivo transcription and translation.

Such methods for expressing AFPs in animal cells and in animals are useful, for example, as clinical, diagnostic, or other research tools for studying the mechanisms of AFP expression, localization of AFPs, mechanisms of signal transduction pathways affected or induced in response to AFP expression, and the effects of various nucleic acid control elements on AFP expression and localization.

In accordance with the invention, the AFPs, nucleic acids and expression vectors of the invention can serve as immunogens for inducing immune responses in animals, particularly HIV specific CTL immune responses. Hence as used herein, the immunogen is the molecule that is delivered to the animal and that directly or indirectly leads to production of an immune response (either humoral or cellular). An HIV immunogen induces a response against HIV which response can be cellular or humoral. HIVCON, RENTA, and HIVA are examples of HIV protein immunogens (see WO 01/47955 for HIVA; PCT/US2004/037699 for RENTA). pTHr.HIVCON, pTHr.RENTA, and pTHr.HIVA are examples of DNA- or plasmid-vectored HIV immunogens. MVA.HIVCON, MVA.RENTA, and MVA.HIVA are examples of virally-vectored HIV immunogens.

The present methods are useful as research tools when immunizing laboratory animals to study the immune response to these immunogens either alone or in conjunction with other HIV immunogens, as well as with or without adjuvants. More particularly, the methods can be for prophylactic or therapeutic prevention, amelioration or treatment of HIV in humans. When provided prophylactically, the methods are ideally administered to a subject in advance of any evidence of HIV infection or in advance of any symptom due to AIDS, especially in high-risk subjects. The prophylactic administration of the immunogens can serve to prevent or attenuate AIDS in a human subject. When provided therapeutically, the methods can serve to ameliorate and treat AIDS symptoms and are advantageously used as soon after infection as possible, preferably before appearance of any symptoms of AIDS but may also be used at (or after) the onset of the disease symptoms.

The recombinant vectors express a nucleic acid molecule encoding AFPs of the present invention. In particular, the AFPs can be isolated, characterized and inserted into vector recombinants. The resulting recombinant vector is used to immunize or inoculate a subject. Expression in the subject of the AFPs can result in an immune response in the subject to the expression products of the AFP. Thus, the recombinant vectors of the present invention may be used in an immunological composition or vaccine to provide a means to induce an immune response, which may, but need not be, protective.

To induce or stimulate an immune response, an AFP or an expression vector of the invention or AFP of the invention is delivered one or more times into the subject so that the encoded AFP is expressed at a level sufficient to induce an immune response to the AFP, or the AFP is provided in an amount sufficient to induce an immune response to AFP. Any delivery method can be used including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes (especially for bacterial expression vectors, e.g., attenuated *Salmonella* or *Shigella* spp.) can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogen (whether an AFP or an expression vector). Hence, the immunogens can be administered one or more times to the subject. Preferably, there is a set time interval between administration of the immunogen. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of immunogen, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods include a variety of prime-boost regimens, especially DNA prime-MVA boost regimens. In these methods, one or more priming immunizations are followed by one or more boosting immunizations. The actual antigen can be the same or different for each immunization and the type of immunogen (e.g., protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a human by administering an AFP of the invention, a nucleic acid of the invention and/or an expression vector of the invention one or more times to a subject wherein the AFP is administered in an amount or expressed at a level sufficient to induce an HIV-specific CTL immune response in the subject. Such immunizations can be repeated multiple times at time intervals of at least 2, 4 or 6 weeks (or more) in accordance with a desired immunization regime.

The method can be used in combination with, including proteins or expression vectors that encode such other antigens. The compositions can be administered alone, or can be co-administered or sequentially administered with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. Many other HIV immunogens are known in the art, one such preferred immunogen is HIVA (described in WO 01/47955), which can be administered as a protein, on a plasmid (e.g., pTHr.HIVA) or in a viral vector (e.g., MVA.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an AFP of the invention, a nucleic acid encoding an AFP of the invention or an expression vector encoding an AFP of the invention, and wherein the immunogens are administered in an amount or expressed at a level sufficient to induce an HIV-specific immune response in the subject. The HIV-specific immune response can include an HIV-specific CTL immune response. Such immunizations can be done at intervals, preferably of at least 2-6 weeks.

In accordance with this method, pTHr.HIVCON is administered one or more times as the priming dose or MVA.HIVCON is administered one or more times as the boosting dose, with or without the priming dose having been pTHr.HIVCON. As an example of using another HIV immunogen in this method, the priming dose can be pTHr.HIVCON and the boosting dose can be MVA.HIVCON, MVA.RENTA, MVA.HIVA, or a mixture of MVA.HIVCON, MVA.RENTA and MVA.HIVA, and combinations thereof. When mixtures are used in the priming or boosting doses, the components can be mixed together for administration or administered separately. When administered separately, the components can be also be administered sequentially as multiple separate priming or boosting doses administered at an interval of 2-6 weeks from each other. One example of an immunization regimen of this method is to administer two priming doses at weeks 0 and 4, each dose being a mixture of pTHr.HIVCON and pTHr.RENTA or pTHr.HIVA, followed by administration of two boosting doses at weeks 8 and 12, each dose being a mixture of MVA.HIVCON, MVA.RENTA, and MVA.HIVA.

The immune response induced by the methods of the invention can be assessed by standard techniques known in the art. For CTL responses, such techniques include but are not limited to, intracellular IFN-γ staining assays, tetramer assays, ELISPOT assays (Beattie, T. et al (2004) AIDS 18(11): 1595-8), and $^{51}$Cr-release assays. A systematic comparison of CTL detection methods can be found in Sun, Y. et al (2003) J. Immunol. Meth. 272(1-2): 23-34; and in Shacklett, B. L. (2002) J. Clin. Immunol. 130(2): 172-82. Other immune responses can be assessed as described in Harlow.

The present invention also comprehends compositions and methods for making and using vectors, including methods for producing gene products and/or immunological products and/or antibodies in vivo and/or in vitro and/or ex vivo (e.g., the latter two being, for instance, after isolation therefrom from cells from a host that has had an administration according to the invention, e.g., after optional expansion of such cells), and uses for such gene and/or immunological products and/or antibodies, especially neutralizing antibodies to HIV (reviewed in Haigwood, N. L. and Stamatatos, L. (2003) 17 (Suppl 4: S67-71), including in diagnostics (reviewed in Truong, H. M. and Klausner, J. D. (2004) MLO Med Lab Obs. 36(7): 12-13, 16, 18-20), assays, therapies, treatments, and the like. The resulting neutralizing antibodies can be used separately, or in combination with the AFPs of the present invention to enhance or modulate immunogenic or immunological responses to HIV, SIV, or SIV/HIV hybrids. The neutralizing antibodies can be tailored for specificity to a particular Clade or CRF, or can be clade-universal. The AFPs of the present invention can be used, in particular, in developing neutralizing antibodies directed to a specific HIV protein sequence that are cross-clade or clade-universal.

The invention also includes the use of the vectors expressing AFPs in the research setting. The vectors can be used to transfect or infect cells or cell lines of interest to study, for example, cellular responses to gene products expressed from the heterologous sequences of interest, or signal transduction pathways mediated by proteins encoded by the heterologous sequences of interest. Such signal transduction pathways can include cytokine expression, or up- or downregulation of genes, such as but not limited to cellular receptors or cell-surface marker proteins, i.e., CD4, CCR5, CXCR5, MHC Class I and II, in response to expression of HIV proteins.

In the research setting, it is often advantageous to design recombinant vectors or viruses that comprise reporter genes that can be easily detected by laboratory assays and techniques. Reporter genes are well known in the art and can comprise resistance genes to antibiotics such as, but not limited to, ampicillin, tetracycline, neomycin, zeocin, kanamycin, bleomycin, hygromycin, chloramphenicol, among others. Reporter genes can also comprise green fluorescent protein, the lacZ gene (which encodes β-galactosidase), luciferase, and β-glucuronidase.

The invention further relates to the product of expression of the AFP and uses thereof, such as to produce a protein in vitro, or to form antigenic, immunological or vaccine compositions for treatment, prevention, diagnosis or testing; and, to DNA from the recombinant vectors, which are useful in constructing DNA probes, antisense RNA molecules, small interfering RNA molecules (siRNA), ribozymes, and PCR primers. The invention also comprehends producing synthetic peptides using the AFPs described herein (see above). The invention can encompass use of the AFPs to identify new or existing isolates, Clades, and CRFs of HIV arising in the environment, i.e. in the circulating population or geographic region, or in a single individual (Ito, Y. et al (2003) J. Clin. Microbiol. 41(5): 2126-31). The AFPs of the invention can also be used, for example, to determine specificity of responses, or mechanisms of resistance, to currently available anti-HIV drugs and therapies in cells or subjects infected with HIV. The efficacy of anti-HIV drugs is often dependent on the Clade or CRF of HIV present in the subject or population of subjects; thus a cross-clade or clade-universal AFP of the present invention can be used advantageously to develop new or optimized anti-HIV drugs or therapies that can be applied to all HIV Clades or CRFs. Additionally, the efficacy of currently available anti-HIV drugs and therapies, such as, for example, AZT, protease inhibitors, fusion inhibitors, and combination therapies thereof, among others, can be modulated or optimized by, inter alia, administering the drug or therapy to cells or subjects expressing the AFP.

The AFPs of the present invention can be used separately, or concurrently with existing anti-HIV therapies, including drug regimens or therapies such as HAART (highly active anti-retroviral therapy), neutralizing antibodies, but are not limited to these examples.

The AFPs of the present invention can also be altered or modified to include sequences from SIV, or from SIV/HIV hybrids, to produce an therapeutic or prophylactic immunogenic or immunological response in non-human primates. The AFPs of the invention can be modified for inclusion in non-human animal models of HIV. One of the skill in the art can easily modify the AFPs of the present invention to encompass SIV sequences and CTL epitopes to induce an immune response that may, but need not be, protective.

It is to be understood and expected that variations in the principles of invention herein disclosed in exemplary embodiments may be made by one skilled in the art and it is intended that such modifications, changes, and substitutions are to be included within the scope of the present invention. All of the patents and publications cited herein are hereby incorporated by reference.

The following examples are given for the purpose of illustrating various embodiments of the invention and are not meant to limit the present invention in any fashion.

EXAMPLES

Example 1

HIVCON Plasmid Construction

The HIVCON ORF (see SEQ ID NO: 1, FIG. 2, and SEQ ID NO: 5, FIG. 6) was designed to encode a chimeric protein derived from the highly conserved domains of HIV proteins. HIVCON chimeric protein contains the 14 most conserved protein domains of HIV with the domains having less than 6% variability between four major HIV Clades A-D. The HIVCON ORF is contained within the HIVCON gene fragment, which also can include the Mamu-A*01 (SIV Gag p27) epitope, the murine P18-I10 (H-$2^K$) epitope and the mAb epitope Pk. The HIVCON gene fragment was synthesized (geneART GmbH, Germany) using preferred human amino acid codon usage (Andre, S. et al (1998) J. Virol. 72(2): 1497-1503). The HIVCON ORF is preceded by a 12-nucleotide consensus Kozak sequence (Kozak, (1987) Nucleic Acid Res. 15:8125-8148) (see SEQ ID NO: 5, FIG. 6). The nucleotide sequences encoding the 14 conserved HIV protein domains were directly fused to each other with the Mamu-A*01 epitope, P18-I10 epitope, presented by H-$2^K$ (Romero et al), and the mAb epitope Pk fused to the C-terminal conserved protein fragment, thus creating the HIVCON coding sequence of SEQ ID NO. 3 (FIG. 4). The entire synthetic gene fragment was sequenced to verify the accuracy of gene synthesis. When a synthesis error was detected, the improper nucleotide(s) was replaced with the correct nucleotide using site-directed mutagenesis. The HIVCON gene fragment was inserted into plasmid pTH (Hanke 1998a) to generate the pTH expression vector. All recombinant DNA manipulations were performed using standard procedures (Sambrook et al., Molecular Cloning; A Laboratory Manual (2nd ed.), Cold Spring Harbor Press, Cold Spring Harbor, N.Y. 1989).

In the experiments presented herein, the pTH.HIVCON vector was used. However, it should be noted that for use in human patients, it is preferred that the β-lactamase gene (ampicillin resistance gene) from pTH is removed (for example by excising the plasmid at the BspHI sites and religating the linear fragment containing HIVCON) to generate the pTHr.HIVCON expression vector. The pTHr.HIVCON plasmid uses an auxotrophic repressor-titration system for bacterial selection and does not carry any antibiotic-resistance gene (Williams et al., (1998) Nucleic Acid Res. 26:2120-2124; U.S. Pat. No. 5,972,708). In the pTHr vector, HIVCON transcription is controlled by an efficient enhancer/promoter/intron A cassette derived from the human cytomegalovirus strain AD 169 (Whittle et al., (1987) Protein Eng. 1: 499-505) and a bovine polyadenylation site (Goodwin et al., (1992) J. Biol. Chem. 267: 16330-16334). Such a pTHr.HIV-CON vector will be particularly useful as a vector for use in humans, i.e. for GMP clinical vaccines.

HIVCONΔH is a version of the HIVCON gene in which the immunodominant mouse P18-I10 epitope of HIVCON gene (the coding sequence for which is present in SEQ ID NOs: 3, and the amino acids for which are those of nucleotide positions 789-798 of SEQ ID NO:4) was deleted by PCR. Similar to HIVCON, HIVCONΔH was inserted in the pTH plasmid thus resulting in the pTH.HIVCONΔH expression vector.

Example 2

Preparation of MVA.HIVCON and MVA.HIVCONΔH

The HIVCON fragment is excised out of pTHr.HIVCON using XmaI and ligated into the XmaI site of transfer vector pSC11 (Chakrabarti) to produce the vector pSC11.HIVCON used in the preparation of recombinant MVA.HIVCON. The plasmid pSC11.HIVCON carries the β-galactosidase gene.

The HIVCONΔH fragment fragment is cut out of pTHr.HIVCONΔH using XmaI and ligated into the XmaI site of transfer vector pSC11 (Chakrabarti) to produce the vector pSC11.HIVCONΔH used in the preparation of recombinant MVA.HIVCONΔH. The plasmid pSC11.HIVCONΔH carries the β-galactosidase gene.

The HIVCON- or HIVCONΔH-coding fragment is inserted into the thymidine kinase locus of the virus genome under the p7.5 early/late vaccinia promoter using plasmid pSC11, which co-delivers a β-galactosidase gene to facilitate screening, titration and stability studies of the recombinant MVA.HIVCON or MVA.HIVCONΔH (Chakrabarti). This marker enzyme is commonly expressed by human enteric bacteria and has been shown to be safe in several clinical trials, including healthy HIV-uninfected volunteers vaccinated with MVA.HIVA.

Briefly, recombinant MVA.HIVCON or MVA.HIV-CONΔH virions are produced from chicken embryonic fibroblasts (CEF) cells grown in Dulbeco's Modified Eagle's Medium (DMEM) supplemented with 10% fetal calf serum (FCS), penicillin/streptomycin and glutamine (DMEM 10) that are infected with parental MVA at a multiplicity of infection (MOI) of 1 and transfected using Superfectin (Qiagen, Germany) with 3 μg of endotoxin-free pSC11.HIVCON. Recombinants are identified by a blue color reaction of β-galactosidase in the presence of X-gal (5-bromo-4-chloro-3-indolyl-bD-galactoside). Recombinants are subjected to five rounds of plaque purification, after which a master virus stock is grown, purified on a 36% sucrose cushion, titered and stored at −80° C. until use. The presence of the correct ORF, either HIVCON or HIVCONΔH, is confirmed by sequencing and immunofluorescence detection of the protein in MVA.HIVCON- or MVA.HIVCONΔH-infected cells.

Example 3

HIVCON and HIVCONΔH Expression in Human Cells

HIVCON and HIVCONΔH expression was assessed in human 293T cells or HEK 293 cells transiently transfected with pTH.HIVCON or pTH.HIVCONΔH. HIVCON and HIVCOΔdH expression was assessed in human 293T cell infected with MVA.HIVCON or MVA.HIVCONΔH at an MOI of 5.

For immunofluorescence studies, six-well plates containing sterile slides pre-treated with poly-L-lysine (70,000-150,000 molecular mass; Sigma) were seeded with 293T cells ($2 \times 10^5$ cells per slide). Twenty four hours later, the cell monolayers were transfected with either pTH.HIVCON or pTH-.HIVCONΔH. To monitor the expression from the MVA constructs, the cell monolayers are infected with MVA.HIVCON or MVA.HIVCONΔH at an MOI of 5. After a 24-hour incubation at 37° C. with 5% $CO_2$, the cells were washed and their membranes were perforated. The slides were blocked with 2% FCS in phosphate-buffered saline (PBS) at 4° C. for 1 hour and incubated with a 1:200 dilution of the designated primary mAb at 4° C. overnight. The mAbs were against the Pk tag (Serotec, Oxford, UK). After incubation, the slides were washed once in PBS and incubated at 4° C. overnight with a 1:500 dilution of an Alexa Fluor 594-conjugated anti-mouse secondary antibody (Molecular Probes, Oregon, USA). The slides were again washed once with PBS, stained with DAPI (4, 6-diamidino-2-phenylindole 2HCl) nuclear stain (in Vectashield® mounting medium, Vector Laboratories, USA) and photographed on a Zeiss immunofluorescence microscope at 40× magnification.

Figure 7:
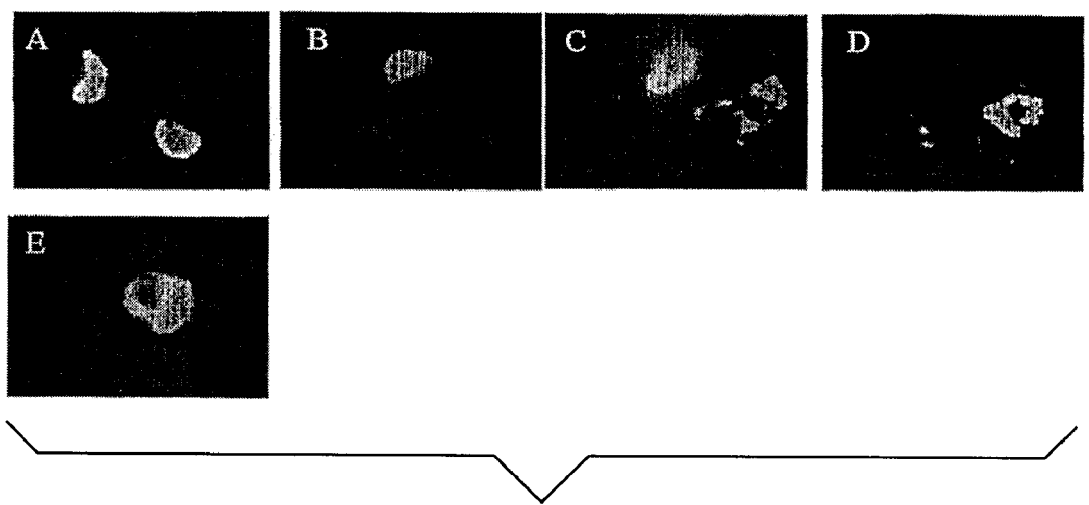
FIG. 7 demonstrates the expression of HIVCON and HIVCONΔH in 293T cells. The expression of the HIVCON protein from pTH.HIVCON plasmid DNA (A), pTH.HIVCONΔH plasmid DNA (B), MVA.HIVCON (C), MVA.HIVCONΔH (D) and Ad.HIVCON (E) in human 293T (A, B, C and D) or HEK 293 (E) cells was detected using immunofluorescence and mAb to the Pk tag of HIVCON. The nuclei are shown in blue (appears as pale gray in black & white), Pk in green (appears as bright/white in black and white) (A, B, C and D) or red (appears as bright/white in black and white) (E).

The immunofluorescence results demonstrate that HIV-CON and HIVCONΔH expression is detectable in human cells using m-Abs against the Pk epitope. FIG. 7 demonstrates the expression of HIVCON and HIVCONΔH in 293T cells. The expression of the HIVCON protein from pTH.HIV-CON plasmid DNA (A), pTH.HIVCONΔH plasmid DNA (B), MVA.HIVCON (C), MVA.HIVCONΔH (D) and Ad.HIVCON (E) in human 293T (A, B, C and D) or HEK 293 (E) cells was detected using immunofluorescence and mAb to the Pk tag of HIVCON. The nuclei are shown in blue (appears as pale gray in black & white), Pk in green (appears as bright/white in black and white) (A, B, C and D) or red (appears as bright/white in black and white) (E).

Example 4

Genetic Stability of MVA.HIVCON and MVA.HIVCONΔH

The genetic stability of the inserted HIVCON or HIVCONΔH ORFs and β-gal genes is confirmed by seven blind sequential passages of the MVA.HIVCON and MVA.HIV-CONdH in CEF cells. The original (passage 0) and the final (passage 7) virus stocks are then used to infect duplicate wells, of which one well is stained with neutral red to detect any MVA plaques (both empty MVA and MVA.HIVCON or MVA.HIVCONdH) and the other well is stained with 5-bromo-4-chloro-3-indolyl-β-D-galactopyranoside (X-gal) to detect the inserted β-gal gene (MVA.HIVCON or MVA-.HIVCONdH) respectively. Comparison of the two titers suggests that MVA.HIVCON and MVA.HIVCONdH are stable above the sensitivity of this assay. Immunofluorescence analysis of CEF cells infected with viral stocks from passages 0 and 7 indicates that the expression levels of HIVCON or HIVCONdH are comparable.

Example 5

Construction of Recombinant huAd5-GFP.HIVCON Vector

The HIVCON vaccine gene is inserted into Ad5 using the pAdEasy1 adenoviral vector system (Hermeking, H. (1997) Mol. Cell 1: 3-11; He, T. C. et al (1998) Proc. Natl. Acad. Sci. 95(5): 2509-14). This system employs efficient homologous recombination machinery in *E. coli* BJ5183 bacterial cells (Nakamura, N. et al (2000) Mol. Cell Biol. 20(23): 8969-8982), generating recombinant adenovirus genome by a double-recombination event between the co-transformed adenoviral backbone plasmid vector, pAdEasy1, and a shuttle vector pAd-TrackCMV, which carries the gene of interest. Viral production is conveniently followed with the aid of green fluorescent protein (GFP), encoded by a gene incorporated into the viral backbone. This system thus allows for the generation of homogenous viruses without the risk of empty adenovirus contamination.

Several PmeI-linearized, recombinant adenovirus DNA carrying the GFP and HIVCON genes are used to transfect six-well plates of HEK293 cells at 70-80% confluency. At 8 days post-transfection, wells are scraped, centrifuged, and re-suspended in 2 ml Hanks Balanced Salt Solution (HBSS; Sigma). The cells are then subjected to four freeze/thaw cycles in a dry ice/methanol bath and 50% of each viral supernatant are used to re-infect 50-70% confluent T-25 flasks of HEK293 cells. Two to 3 days after re-infection, virus is again harvested in a similar fashion and used to infect T-75 flasks and subsequently, T-175 flasks. This is repeated for several rounds over a 10-day period prior to purification.

Purification of AdGFP-HIVCON is performed using the Adenopure1 purification kit (Puresyn Inc.; USA) as per manufacturer's instruction. In brief, four T-175 cm$^2$ flasks infected with AdGFP-HIVCON are scraped, subjected to 3 freeze/thaw cycles in a dry ice/methanol bath and the supernatant obtained after pelleting of the cellular debris is passed over an absorber membrane with proprietary buffer formulations to isolate highly purified adenovirus preparations. Viral titer is determined by serial dilution of purified AdGFP-HIVCON in six-well plates seeded with HEK293 cells at 70-80% confluence and enumeration of GFP expressing cells 24-hours post-infection.

Example 6

HIVCON Immunogenicity in Mice

The immunogenicity of the pTH.HIVCON was assessed in mice using the P18-I10 epitope. Two groups of 5-6 week-old female BALB/c mice were injected into the anterior tibial muscles with 50 μg of endotoxin-free pTH.HIVCON in PBS under general anesthesia. Ten days later, the animals were sacrificed and their spleens were removed. Individual spleens were processed through a cell strainer (Falcon) using a 2-ml syringe rubber plunger. The splenocytes from each animal were washed twice and suspended in 10 ml of lymphocyte medium (RPMI 1640 supplemented with 10% FCS penicillin/streptomycin, 20 mM HEPES and 15 mM 2-mercaptoethanol). Eight ml of splenocyte suspension was used for a bulk CTL culture.

To prepare the bulk CTL cultures, 8 ml of the splenocyte suspension were incubated with 2 pg/ml of P18-I10 peptide in an humidified incubator in 5% $CO_2$ at 37° C. for 5 days. On the day of the CTL assay, the cells were washed 3 times with RPMI and resuspended at 10$^7$ cells per ml in R10 (RPMI 1640 supplemented with 10% FCS and penicillin/streptomycin) for use as effector cells in a $^{51}$Cr-release assay.

For each batch of splenocytes, the effector cells were diluted 2-fold in U-bottom wells of a 96-well plate (Costar) using R10 medium to yield effector to target ratios between 200:1 to 3:1 after addition of the target cells. Five thousand $^{51}$Cr-labeled P815 target cells in R10 medium with or without 2 pg/ml of P18-I10 peptide were added to the effectors and the mixture was incubated at 37° C. for 5 hours. Spontaneous and total chromium releases were estimated from wells containing target cells in medium alone or in medium with 5% Triton X-100, respectively. The percentage specific lysis was calculated as [(sample release-spontaneous release)/(total release-spontaneous release)]×100. The spontaneous release was lower than 5% of the total counts per minute.

Figure 8A:
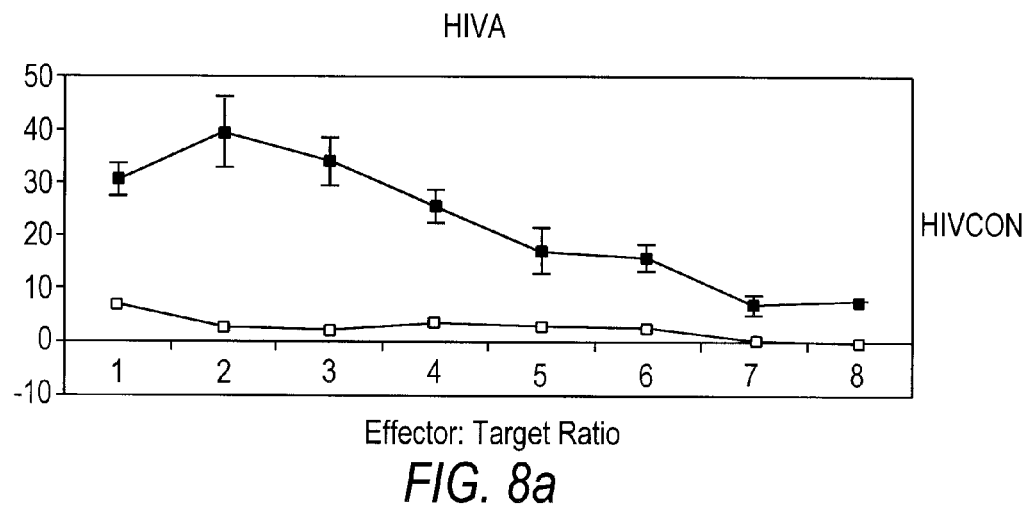
FIG. 8 is a killing assay that demonstrates the immunogenicity of pTHr.HIVCON as assessed by the elicitation of T-cell responses against the P18-I10 epitope of HIVCON. BALB/c mice were immunized with a single dose of 100 μg DNA intramuscularly. Splenocytes were harvested after 10 days, restimulated for 5 days in culture with the P18-I10 peptide and tested in a $^{51}$Cr-release assay. The figure graphically illustrates the percentage of specific lysis as a function of effector target cell ratio in a $^{51}$Cr-release assay for mice immunized with pTHr.HIVA (left panel) or pTHr.HIVCON (right panel) using P18-I10 peptide-pulsed (solid circle) or unpulsed (open circle) target cells.
Figure 8B:
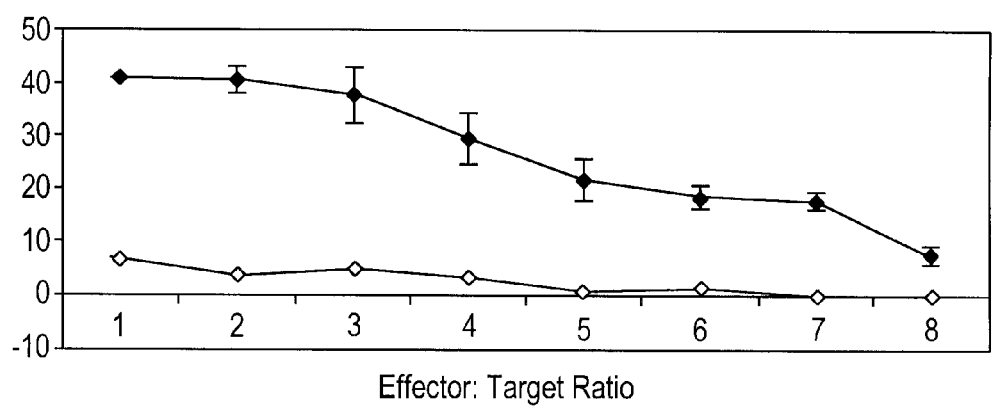

In FIG. 8, the left panel shows the results for mice immunized with pTHr.HIVA as control and the right panel shows the results for mice immunized pTHr.HIVCON in the $^{51}$Cr-release assay with peptide-pulsed (solid circle) or unpulsed (open circle) target cells. All animals responded to the immunization and relatively high levels of lytic activities were detected.

Example 7

Demonstration of Murine T-Cell Responses to the HIVCON Immunogen

The T-cell response induced against the HIVCON immunogen was examined when pTH.HIVCON was administered in BALB/c mice. Induction of specific immune responses to the P18-I10 epitope of HIVCON was demonstrated using an ex vivo intracellular cytokine staining assay. For this assay, mouse splenocytes isolated from mice treated with HIVA or HIVCON were stimulated with the appropriate P18-I10 peptide-pulsed P815 cells in the presence of anti-CD28/anti-CD49d mAbs for 90 minutes at 37° C. in 5% $CO_2$. Brefeldin A was then added to inhibit cytokine secretion and the samples were incubated for additional 6 hours before terminating the reaction with EDTA and FACS fix solution. The cells were permeabilized and incubated with phycoerythrin (PE)-conjugated anti-CD8 and fluorescein isothiocyanate (FITC)-conjugated anti-IFN-γ mAbs (BD PharMingen) and analyzed using FACS.

Figure 9:
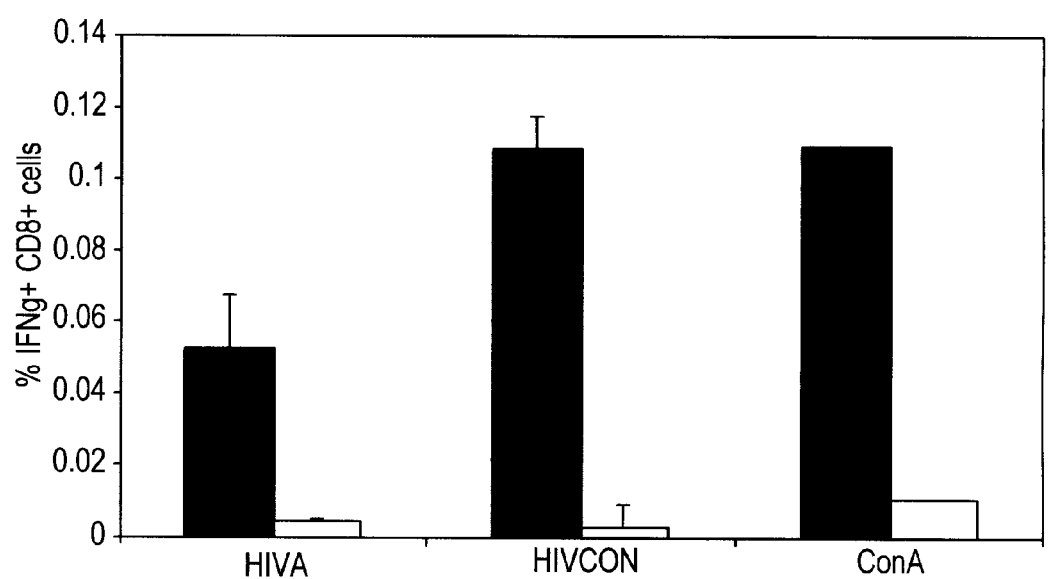
FIG. 9 shows a bar graph representation of FACS analyses of the percentages of CD8+ splenocytes producing IFN-γ among mouse splenocytes isolated from mice treated with HIVA or HIVCON immunogen and stimulated (filled bars) or unstimulated (open bars) with P18-I10 peptide.

The results in FIG. 9 demonstrate the CTL response induced by HIVCON immunogen. The percentage of CD8+ splenocytes producing IFN-γ are shown for mouse splenocytes isolated from mice treated with HIVA or HIVCON immunogen and stimulated with P18-I10 peptide. The results further demonstrate that the percentage of IFN-γ-producing CD8+ cells induced by the HIVCON immunogen is approximately two-fold higher in animals immunized with pTH.HIVCON compared to animals immunized with the control immunogen HIVA. The percentage of CD8+ cells in the ConA column of the graph serve as a positive control for CTL induction.

Example 8

Demonstration of Broad Murine T-Cell Responses to HIVCON

The breadth of the T-cell responses induced against the HIVCON or HIVCONΔH immunogens is examined when either HIVCON, in the form of pTH.HIVCON, pTHr.HIVCON, MVA.HIVCON or huAd5-GFP.HIVCON, or HIVCONΔH in the form of pTH.HIVCONΔH, pTHr.HIVCONΔH or MVA.HIVCONdΔH is administered in BALB/c mice. Induction of specific immune response to the P18-I10 epitope or specific epitopes of HIVCON is demonstrated using an ex vivo intracellular cytokine staining assay. For this assay, mouse splenocytes are isolated from mice treated with HIVCON or HIVCONdH and are subsequently stimulated with the appropriate P18-I10 peptide- or peptide pools pulsed P815 cells in the presence of anti-CD28/anti-CD49d mAbs for 90 minutes at 37° C. in 5% $CO_2$. Brefeldin A is then added to inhibit cytokine secretion and the samples are incubated for additional 6 hours before terminating the reaction with EDTA and FACS fix solution. The cells are permeabilized and incubated with PE-conjugated anti-CD8 and FITC-conjugated anti-IFN-γ mAbs (BD PharMingen) and analyzed using FACS.

The results demonstrate that multiple specificities of CTL are induced by the immunogens, where the percentage of CD8+ splenocytes producing IFN-γ from HIVCON or HIVCONdH immunized mice is significantly higher than the percentage of CD8+ splenocytes producing IFN-γ from naive (unimmunized) mice.

The peptide pools consist of 15-mer peptides overlapping by 11 amino acids across the entire length of the HIVCON immunogen. Each pool can include peptides that cover approximately 50-100 amino acids from the length of the HIVCON immunogen.

Example 9

In Vitro CFSE Proliferation Assay

Figure 10:
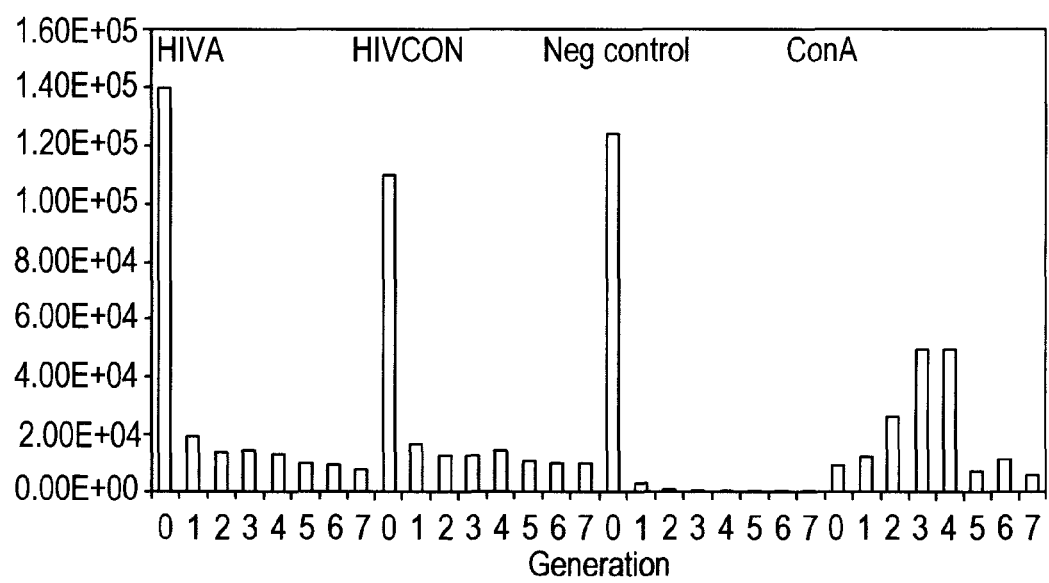
FIG. 10 shows the results of in vitro proliferation assay. BALB/c mice were immunized with a single dose of 100 μg DNA intramuscularly. Splenocytes were harvested after 10 days, stained with CFSE and restimulated for 5 days in culture with the P18-I10 peptide and analyzed on a FACS Calibur. FACS data acquisition was gated on lymphocytes and CD8+ populations. Data from representative mice is shown.

A carboxy-fluorescein diacetate succinimidyl ester (CFSE) staining assay was used to monitor the proliferative capacity of splenocytes from mice immunized with pTH.HIVA or pTH.HIVCON and restimulated with the P18-I10 peptide. BALB/c mice were immunized with a single shot of 100 μg DNA intramuscularly. Splenocytes were harvested after ten days and isolated splenocytes were stained with CFSE (Molecular Probes) at a final concentration of 2 μM at 37° C. for 10 min. The reaction was stopped by the addition of fetal calf serum. Cells were washed three times, resuspended in lymphocyte medium and restimulated with 2 μg/ml P18-I10 peptide. Splenocytes cultures were incubated at 37° C., 5% $CO_2$ for 5 days, analyzed on a FACScan (BD) and data analysis was performed using the CellQuest software (BD). The results presented in FIG. 10 demonstrate that the splenocytes from mice immunized with pTH.HIVCON continue to proliferate for multiple generations in culture, similar to splenocytes restimulated with pTH.HIVA or ConA (positive controls), and in contrast to splenocytes that were not restimulated with P18-I10 (negative control panel).

Example 10

Immunogenicity of HIVCON in Transgenic HHD Mice Expressing Human HLA

Transgenic HHD mice expressing interspecies HLA-A2 monochains have been described previously (Pascolo et al. (1997) J Exp Med 185:2043-2051). These mice constitute a versatile murine model for the study of HLA-A2.1 restricted CTL responses of potential human vaccines. The HHD transgenic animals express the interspecies recombinant transgenic molecule, N-terminus human β2m-HLA-A2.1 (α1α2)-mouse H-2$D^b$(α3), transmembrane, and cytoplasmic domains C-terminus, in the double knockout background H-2$D^{b-/-}$β2m$^{-/-}$. Two approaches are undertaken to identify novel HLA-A2 restricted CTL epitopes specific of the HIVCON AFP. First, prediction algorithms are used to identify potential peptides that may bind well to HLA-A2 protein (Tourdot et al. (2000) Eur J Immunol 30:3411-3421). Second, a library of 15-mer peptides that overlap by eleven amino acids and span the entire length of the HIVCON AFP are designed. The library of 15-mer peptides are distributed in a number of peptide pools based on sequence overlap that will reduce the number of functional assays that will be performed. Both the prediction based peptides and the 15-mer library peptides are synthesized and purified by standard proteins synthesis techniques. These peptides are tested for their ability to bind to the HHD single chain in an assay that measures peptide binding by stabilization of cell surface MHC molecules (Carmon et al. (2002) J Clin Invest 110:453-462). Upon identification of a peptide pool that induces the desired CTL response, fractionation of the peptide pools will identify the individual peptide that induces the CTL response.

HHD mice are immunized intramuscularly with pTH.HIVCON in PBS under general anesthesia. Splenocytes for bulk CTL culture are prepared essentially as described in Example 5. The ability of the prediction based peptides and the library peptides to induce broad CTL response are assessed in a variety of ways, including an ex vivo intracellular cytokine staining assay (essentially as described in Example 6) and an in vitro cytotoxicity assay that measures CTL induces cell lysis of target cells (essentially as described in Example 5).

Initially, the immunogenicity of the pTH.HIVCON and MVA.HIVCON vaccines in BALB/c are confirmed using a C-terminal H-2$D^d$-restricted epitope RGPGRAFVTI (called H). Using overlapping peptide across the whole HIVCON protein, the frequencies of immunogenic epitopes are estimated in various mouse strains. Because the above epitope is strongly immunodominant in the H-2$^d$ haplotype, experiments in BALB/c mice are carried out using HIVCONdH vaccines, from which the H epitope was deleted (Example 1). Immune splenocytes from HLA-A2 (HHD) and HLA-B27 transgenic mice are also tested on target cells matched for the appropriate HLA molecules pulsed with overlapping HIVCON peptides. Alternatively, HIVCON-induced T cells from the HLA-transgenic mice are tested on HLA-matched, phytohaemagglutinin (PHA)-blasted, HIV-1-infected human CD4+ cells. Second, the immunogenicity of the DNA-MVA/HIVCON in non-human primates is examined. Third, an important experiment is to assess if HIV-infected individuals have responses that can recognize HIVCON-derived peptides. This is performed with either fresh or in culture-expanded IFN-gamma ELISPOTs, intracellular cytokine staining or killing assays where autologous B-LCLs are available. Positive responses in the HIV-infected individuals would demonstrate that the HIV-infected cells indeed process and present epitopes from the conserved HIV regions.

Example 11

Immunogenicity in Non-Human Primates

Rhesus macaques (*Macaca mulatta*) positive for the Mamu-A*01 allele of MHC class I are immunized with a DNA prime-MVA boost regimen. Three macaques (monkeys 1-3) will receive immunizations with plasmids pTHr.HIV-CON at weeks 0 and 4, followed by immunization with recombinant MVA.HIVCON at weeks 20 and 24. Two macaques (monkeys 4 and 5) will receive the same priming immunizations but boosted with recombinant MVA.HIV-CON at weeks 8 and 12. The immunizations consist of 1 mg of each plasmid in 0.5 ml of 140 mM NaCl, 0.5 mM Tris-HCl, pH 7.7 and 0.05 mM EDTA delivered i.m. or $5 \times 10^7$ pfu of each MVA in 0.1 ml of 140 mM NaCl and 10 mM Tris-HCl, pH 7.7 delivered intradermally (i.d.). The HIVCON vaccines are delivered into the animals' arms. All immunizations and venipunctures are carried out under sedation with ketamine and the animals were regularly clinically examined.

Monkey PBMC are isolated from heparinized blood using the Lymphoprep™ cushion centrifugation (Nycomed Pharma AS). PBMCs are cultured for 2 weeks with peptides derived from the SIV Gag (CTPDYNQM) proteins for peptide-specific expansion. Tetrameric MHC/peptide complexes for Mamu-A*01/Gag are prepared as described elsewhere. Immunogenicity is assessed using PBMCs restimulated with the Gag peptide for 2 weeks at 37° C., 5% $CO_2$ with an addition of huIL-2 on day 3. On the day of the assay, the cells are reacted with phycoerythrin (PE)-conjugated Mamu-A*01/peptides tetrameric complexes and mouse anti-huCD8-PerCP mAb (BD PharMingen) and analyzed by FACS.

Using both the Mamu-A*01-restricted and overlapping peptides derived from the HIVA and RENTA immunogens, multi-specific responses are detected to the HIVCON vaccines in an IFN-γ ELISPOT assay ex vivo. The IFN-γ ELISPOT assay is carried out on DNA primed-MVA boosted animals using freshly isolated PBMC (drawn at week 22) for both the Mamu-A*01-restricted epitope peptides and overlapping pools of peptides across the HIVCON proteins. The procedures and reagents of the MABTECH kit (Mabtech AB) are used. Briefly, PBMC are isolated on a Lymphoprep cushion and incubated at 37° C., 5% $CO_2$ for 24 hours with the indicated peptide or peptide pool. The released IFN-γ is captured by a mAb immobilized on the bottom of assay wells, visualized by combination of a second mAb coupled to an enzyme and a chromogenic substrate. Spots are counted using an ELISPOT reader (Autoimmun Diagnostika GmbH, Germany) and expressed as spot-forming units per $10^6$ splenocytes.

For monkey bulk CTL cultures, $8 \times 10^6$ isolated PBMC are restimulated with 10 µm peptide (or peptide pool) in 100 µl of R20 in 5% $CO_2$ at 37° C. for 1 hour and resuspended in total of 4 ml of R20 supplemented with 25 ng/ml of huIL-7 in two 24-well-plate wells. On day 3, Lymphocult-T (Biotest AG) is added to the final concentration of 10% (v/v). On day 8, $5 \times 10^6$ peptide-pulsed irradiated autologous B lymphoblastoid cell lines (B-LCL) is added to the cultures followed by Lymphocult-T on day 11. Cytolytic tests were carried out on day 14.

For the $^{51}$Cr-release assay, the effector cells are diluted sequentially 2-fold in U-bottom wells 96-well plates (Costar) at effector to target ratios of 50:1, 25:1 and 12:1. Five thousand $^{51}$Cr-labelled autologous B-LCL pulsed (2 µg/ml) or unpulsed with peptide (Gag) or peptide pools (for HIVCON) are added to the effectors and incubated at 37° C. for 6 hours. Percent specific lysis is calculated as for the mouse lysis assays. Spontaneous release is for all samples below 20% of the total counts.

Example 12

Immunogenicity of HIVCON Vaccines in BALB/c Mice

See FIG. 11 (A) which shows immunogenicities of the individual vaccine components. Splenocytes from individual animals were tested ex vivo for the production of IFN-γ in an ELISPOT assay using the RGPGRAFVTI epitope. See FIG. 11(B), where experiments were performed as above (data in FIG. 11 (B)), but with higher doses for the MVA.HIVCON and Ad.HIVCON vaccines. FIG. 11 (C) demonstrates the immunogenicities of individual vaccine components compared to various prime-boost vaccination regimes, using an IFN-γ ELISPOT assay as above. FIG. 11 (D) demonstrates immunogenicities of individual vaccine components compared to a DNA prime-MVA boost vaccination regime. Splenocytes from individual animals were restimulated for 5 days in culture with the RGPGRAFVTI peptide and tested in a $^{51}$Cr-release assay on peptide pulsed (full) or unpulsed (open) targets.

Example 13

Immunogenicity of the HIVCON and HIVCONΔH Vaccines in BALB/c Mice

Figure 12A:
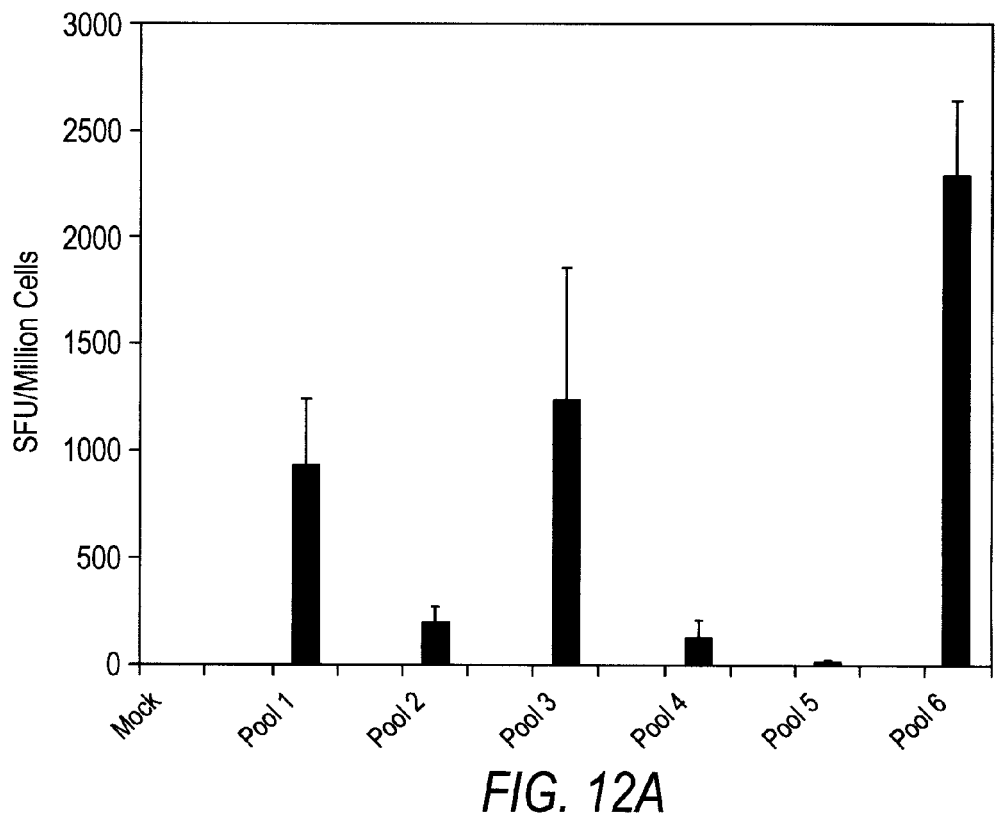
FIG. 12. Immunogenicity of the HIVCON and HIVCONΔH vaccines in BALB/c mice. (A) Splenocytes from individual animals were tested ex vivo for the production of IFN-γ in an ELISPOT assay using pools of overlapping peptides spanning the entire HIVCON sequence. Animals were immunized with 100 μg of pTH.HIVCON at 0 weeks, $10^8$ PFU of Ad.HIVCON at 2 weeks, and $10^7$ PFU of MVA.HIVCON at 8 weeks. Animals were sacrificed at 10 weeks. (B) As for (A), but using animals immunized with 100 µg of pTH-.HIVCONΔH at 0 weeks and 10⁷ PFU of MVA.HIVCONµH at 2 weeks. Animals were sacrificed at 4 weeks. The reactive peptides in pools 1, 3 and 4 were identified.
Figure 12B:
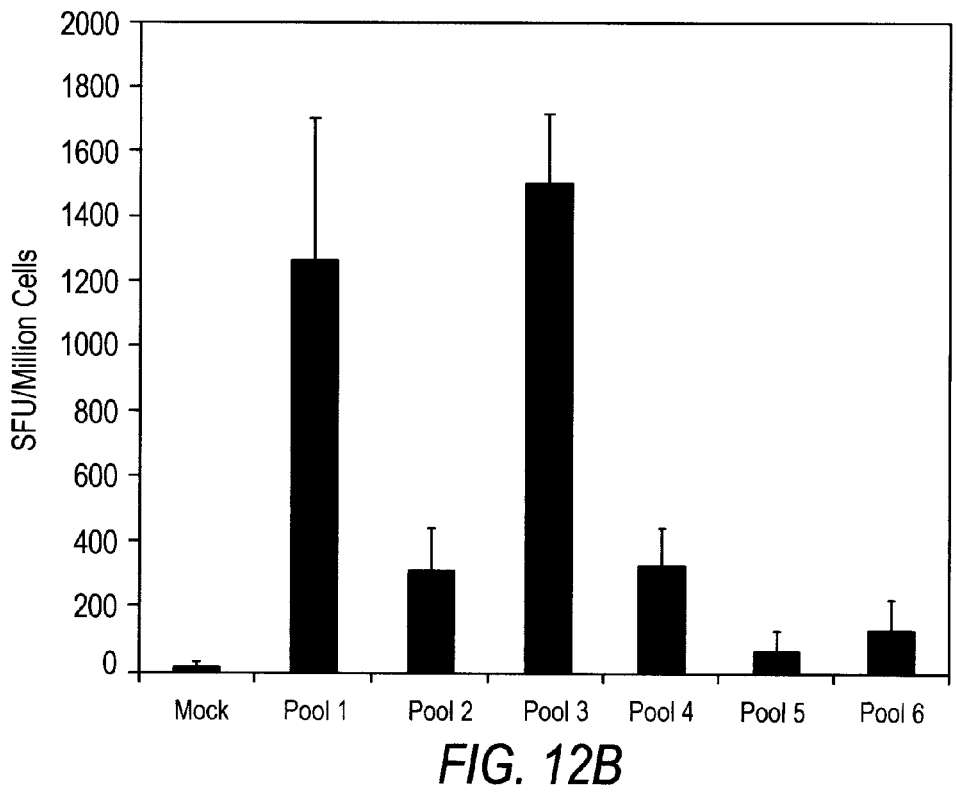

Splenocytes from individual animals were tested ex vivo for the production of IFN-γ in an ELISPOT assay using pools of overlapping peptides spanning the entire HIVCON sequence. Animals were immunized with 100 µg of pTH.HIVCON at 0 weeks, $10^8$ PFU of Ad.HIVCON at 2 weeks, and $10^7$ PFU of MVA.HIVCON at 8 weeks. Animals were sacrificed at 10 weeks. The results are illustrated in FIG. 12(A). A similar experiment was performed but using animals immunized with 100 µg of pTH.HIVCONΔH at 0 weeks and $10^7$ PFU of MVA.HIVCONµH at 2 weeks. Animals were sacrificed at 4 weeks. The results are illustrated in FIG. 12(B). The reactive peptides in pools 1, 3 and 4 were identified.

Example 14

Immunogenicity of the HIVCON Vaccine in HLA-A2 Transgenic Mice HHD

Figure 13:
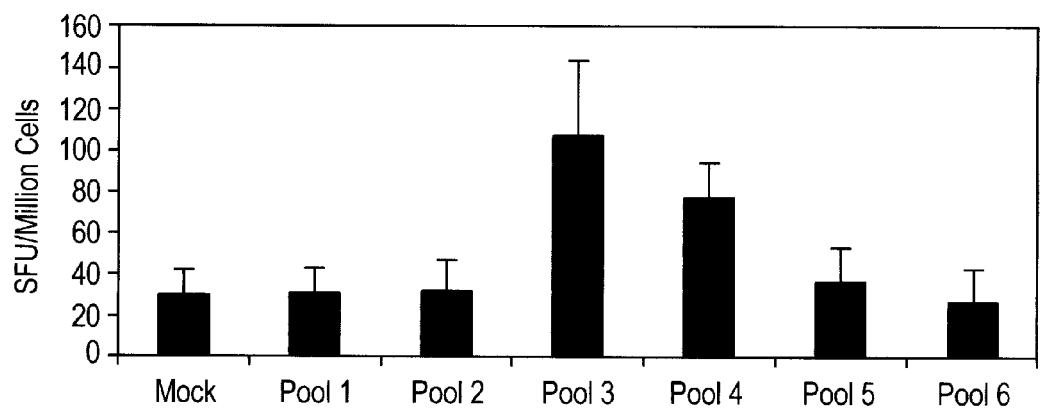
FIG. 13. Immunogenicity of the HIVCON vaccine in HLA-A2 transgenic mice HHD. Splenocytes from individual HHD animals were tested ex vivo for the production of IFN-γ in an ELISPOT assay using pools of overlapping peptides spanning the entire HIVCON sequence. Animals were immunized with 100 µg of pTH.HIVCON at week 0, 10⁸ PFU of Ad.HIVCON at week 2, and 10⁷ PFU of MVA.HIVCON at week 8. Animals were sacrificed at week 10. Reactive peptides in pools 3 and 4 were identified.

Splenocytes from individual HHD animals were tested ex vivo for the production of IFN-γ in an ELISPOT assay using pools of overlapping peptides spanning the entire HIVCON sequence. Animals were immunized with 100 µg of pTH.HIVCON at week 0, $10^8$ PFU of Ad.HIVCON at week 2, and $10^7$ PFU of MVA.HIVCON at week 8. Animals were sacrificed at week 10. The results are demonstrated in FIG. 13. Reactive peptides in pools 3 and 4 were identified.

REFERENCES

Gaschen, B., Taylor, J., Yusim, K., Foley, B., Gao, F., Lang, D., Novitsky, V., Haynes, B., Hahn, B. H., Bhattacharya, T., and Korber, B. (2002) "Diversity considerations in HIV-1 vaccine selection" Science 296(5577): 2354-60.

Pantaleo, G. et al., *Retroviral Immunology: Immune Response and Restoration (Infectious Disease)* (2001) Humana Press, Totowa, N.J., pp. 1-31.

Jung, A., Maier, R., Vartanian, J. P., Bocharov, G., Jung, V., Fischer, U., Meese, E., Wain-Hobson, S., and Meyerhans, A. (2002) "Multiply infected spleen cells in HIV patients" Nature 418(6894): 144.

Abbas, A. K. and Lichtman, A. H., *Cellular and Molecular Immunology* (2000) 4$^{th\ a}$Edition, W.B. Saunders Company, Philadelphia, Pa., p. 454.

Hanke, T., Blanchard, T. J., Schneider, J., Hannan, C. M., Becker, M., Gilbert, S. C., Hill, A. V., Smith, G. L., and McMichael, A. (1998a) "Enhancement of MHC class I-restricted peptide-specific T cell induction by a DNA prime/MVA boost vaccination regime" Vaccine 16(5): 439-45.

Schneider, J., Gilbert, S. C., Blanchard, T. J., Hanke, T., Robson, K. J., Hannan, C. M., Becker, M., Sinden, R., Smith, G. L., and Hill, A. V. (1998) "Enhanced immunogenicity for CD8+ T cell induction and complete protective efficacy of malaria DNA vaccination by boosting with modified vaccinia virus Ankara" Nat Med. 4(4): 397-402.

Kent, S. J., Zhao, A., Best, S. J., Chandler, J. D., Boyle, D. B., and Ramshaw, I. A. (1998) "Enhanced T-cell immunogenicity and protective efficacy of a human immunodeficiency virus type 1 vaccine regimen consisting of consecutive priming with DNA and boosting with recombinant fowlpox virus" J Virol. 72(12): 10180-8.

Hanke, T., Samuel, R. V., Blanchard, T. J., Neumann, V. C., Allen, T. M., Boyson, J. E., Sharpe, S. A., Cook, N., Smith, G. L., Watkins, D. I., Cranage, M. P., and McMichael, A. J. (1999) "Effective induction of simian immunodeficiency virus-specific cytotoxic T lymphocytes in macaques by using a multiepitope gene and DNA prime-modified vaccinia virus Ankara boost vaccination regimen" J Virol. 73(9): 7524-32.

Allen, T. M., Vogel, T. U., Fuller, D. H., Mothe, B. R., Steffen, S., Boyson, J. E., Shipley, T., Fuller, J., Hanke, T., Sette, A., Altman, J. D., Moss, B., McMichael, A. J., and Watkins, D. I. (2000a) "Induction of AIDS virus-specific CTL activity in fresh, unstimulated peripheral blood lymphocytes from rhesus macaques vaccinated with a DNA prime/modified vaccinia virus Ankara boost regimen" J Immunol. 164(9): 4968-78.

Amara, R. R., Villinger, F., Altman, J. D., Lydy, S. L., O'Neil, S. P., Staprans, S. I., Montefiori, D. C., Xu, Y., Herndon, J. G., Wyatt, L. S., Candido, M. A., Kozyr, N. L., Earl, P. L., Smith, J. M., Ma, H. L., Grimm, B. D., Hulsey, M. L., Miller, J., McClure, H. M., McNicholl, J. M., Moss, B., and Robinson, H. L. (2001) "Control of a mucosal challenge and prevention of AIDS by a multiprotein DNA/MVA vaccine" Science 292(5514): 69-74.

Allen, T. M., Jing, P., Calore, B., Horton, H., O'Connor, D. H., Hanke, T., Piekarczyk, M., Ruddersdorf, R., Mothe, B. R., Emerson, C., Wilson, N., Lifson, J. D., Belyakov, I. M., Berzofsky, J. A., Wang, C., Allison, D. B., Montefiori, D. C., Desrosiers, R. C., Wolinsky, S., Kunstman, K. J., Altman, J. D., Sette, A., McMichael, A. J., and Watkins, D. I. (2002) "Effects of cytotoxic T lymphocytes (CTL) directed against a single simian immunodeficiency virus (SIV) Gag CTL epitope on the course of SIVmac239 infection" J Virol. 76(20): 10507-11.

Shiver, J. W., Fu, T. M., Chen, L., Casimiro, D. R., Davies, M. E., Evans, R. K., Zhang, Z. Q., Simon, A. J., Trigona, W. L., Dubey, S. A., Huang, L., Harris, V. A., Long, R. S., Liang, X., Handt, L., Schleif, W. A., Zhu, L., Freed, D. C., Persaud, N. V., Guan, L., Punt, K. S., Tang, A., Chen, M., Wilson, K. A., Collins, K. B., Heidecker, G. J., Fernandez, V. R., Perry, H. C., Joyce, J. G., Grimm, K. M., Cook, J. C., Keller, P. M., Kresock, D. S., Mach, H., Troutman, R. D., Isopi, L. A., Williams, D. M., Xu, Z., Bohannon, K. E., Volkin, D. B., Montefiori, D. C., Miura, A., Krivulka, G. R., Lifton, M. A., Kuroda, M. J., Schmitz, J. E., Letvin, N. L., Caulfield, M. J., Bett, A. J., Youil, R., Kaslow, D. C., and Emini, E. A. (2002) "Replication-incompetent adenoviral vaccine vector elicits effective anti-immunodeficiency-virus immunity" Nature 415(6869): 331-5.

McConkey, S. J., Reece, W. H., Moorthy, V. S., Webster, D., Dunachie, S., Butcher, G., Vuola, J. M., Blanchard, T. J., Gothard, P., Watkins, K., Hannan, C. M., Everaere, S., Brown, K., Kester, K. E., Cummings, J., Williams, J., Heppner, D. G., Pathan, A., Flanagan, K., Arulanantham, N., Roberts, M. T., Roy, M., Smith, G. L., Schneider, J., Peto, T., Sinden, R. E., Gilbert, S. C., and Hill, A. V. (2003) "Enhanced T-cell immunogenicity of plasmid DNA vaccines boosted by recombinant modified vaccinia virus Ankara in humans" Nat Med. 9(6): 729-35.

Hanke, T., and McMichael, A. J. (2000) "Design and construction of an experimental HIV-1 vaccine for a year-2000 clinical trial in Kenya" Nat Med. 6(9): 951-5.

Hanke, T., McMichael, A. J., Mwau, M., Wee, E. G., Ceberej, I., Patel, S., Sutton, J., Tomlinson, M., and Samuel, R. V. (2002a) "Development of a DNA-MVA/HIVA vaccine for Kenya" Vaccine 20(15): 1995-8.

Hanke, T., Barnfield, C., Wee, E. G., Agren, L., Samuel, R. V., Larke, N., and Liljestrom, P. (2003) "Construction and immunogenicity in a prime-boost regimen of a Semliki Forest virus-vectored experimental HIV clade A vaccine" J Gen Virol. 84(Pt 2): 361-8.

Hanke, T., McMichael, A. J., Samuel, R. V., Powell, L. A., McLoughlin, L., Crome, S. J., and Edlin, A. (2002b) "Lack of toxicity and persistence in the mouse associated with administration of candidate DNA- and modified vaccinia virus Ankara (MVA)-based HIV vaccines for Kenya" Vaccine 21(1-2): 108-14.

Wee, E. G., Patel, S., McMichael, A. J., and Hanke, T. (2002) "A DNA/MVA-based candidate human immunodeficiency virus vaccine for Kenya induces multi-specific T cell responses in rhesus macaques" J. Gen. Virol. 83(Pt 1): 75-80.

Singh, R. A., Wu, L., and Barry, M. A. (2002) "Generation of genome-wide CD8 T cell responses in HLA-A*0201 transgenic mice by an HIV-1 ubiquitin expression library immunization vaccine" J Immunol. 168(1): 379-91.

Hanke, T., Schneider, J., Gilbert, S. C., Hill, A. V., and McMichael, A. (1998b) "DNA multi-CTL epitope vaccines for HIV and *Plasmodium falciparum*: immunogenicity in mice" Vaccine 16(4): 426-35.

Rowland-Jones, S. L., Dong, T., Fowke, K. R., Kimani, J., Krausa, P., Newell, H., Blanchard, T., Ariyoshi, K., Oyugi, J., Ngugi, E., Bwayo, J., MacDonald, K. S., McMichael, A. J., and Plummer, F. A. (1998) "Cytotoxic T cell responses to multiple conserved HIV epitopes in HIV-resistant prostitutes in Nairobi" J Clin Invest. 102(9): 1758-65.

Dorrell, L., Hessell, A. J., Wang, M., Whittle, H., Sabally, S., Rowland-Jones, S., Burton, D. R., and Parren, P. W. (2000) "Absence of specific mucosal antibody responses in HIV-exposed uninfected sex workers from the Gambia" AIDS 14(9): 1117-22.

Harlow, E. and Lane, D., *Using Antibodies: A Laboratory Manual* (1998) Cold Spring Harbor Laboratory Press, Cold Spring Harbor, N.Y.

Allen, T. M., O'Connor, D. H., Jing, P., Dzuris, J. L., Mothe, B. R., Vogel, T. U., Dunphy, E., Liebl, M. E., Emerson, C., Wilson, N., Kunstman, K. J., Wang, X., Allison, D. B., Hughes, A. L., Desrosiers, R. C., Altman, J. D., Wolinsky, S. M., Sette, A., and Watkins, D. I. (2000b) "Tat-specific cytotoxic T lymphocytes select for SIV escape variants during resolution of primary viraemia" Nature 407(6802): 386-90.

Romero, P., Maryanski, J. L., Corradin, G., Nussenzweig, R. S., Nussenzweig, V., and Zavala, F. (1989) "Cloned cytotoxic T cells recognize an epitope in the circumsporozoite protein and protect against malaria" Nature 341(6240): 323-6.

Hanke, T., Szawlowski, P., and Randall, R. E. (1992) "Construction of solid matrix-antibody-antigen complexes containing simian immunodeficiency virus p27 using tag-specific monoclonal antibody and tag-linked antigen" J Gen Virol. 73 (Pt 3): 653-60.

Andre, S., Seed, B., Eberle, J., Schraut, W., Bultmann, A., and Haas, J. (1998) "Increased immune response elicited by DNA vaccination with a synthetic gp120 sequence with optimized codon usage" J Virol. 72(2): 1497-503.

Nakamura, Y., Wada, K., Wada, Y., Doi, H., Kanaya, S., Gojobori, T., and Ikemura, T. (1996) "Codon usage tabulated from the international DNA sequence databases" Nucleic Acids Res. 24(1): 214-5.

Wang, T. T., Cheng, W. C., and Lee, B. H. (1998) "A simple program to calculate codon bias index" Mol Biotechnol. 10(2): 103-6.

McEwan, N. R., and Gatherer, D. (1998) "Adaptation of standard spreadsheet software for the analysis of DNA sequences" Biotechniques 24(1): 131-6.

Mayr, A., Hochstein-Mintzel, V., Stickl, H. (1975) "Abstammung, Eigenschaften und Verwendung des attenuierten Vaccinia-Stammes MVA" Infection 105: 6-14.

Chakrabarti, S., Brechling, K., and Moss, B. (1985) "Vaccinia virus expression vector: coexpression of beta-galactosidase provides visual screening of recombinant virus plaques" Mol. Cell. Biol. 5(12): 3403-9.

Smerdou, C. and Liljestrom, P. (2000) "Alphavirus vectors: from protein production to gene therapy" Gene Ther. Regul. 1: 33-63.

Lundstrom, K. (2002) "Alphavirus vectors as tools in cancer gene therapy" Technol Cancer Res Treat. 1(1): 83-8.

Polo, J. M., and Dubensky, T. W. Jr. (1998) "DNA vaccines with a kick". Nat. Biotechnol. 16(6): 517-8.

Berglund, P., Smerdou, C., Fleeton, M. N., Tubulekas, I., and Liljestrom, P. (1998) "Enhancing immune responses using suicidal DNA vaccines" Nat. Biotechnol. 16(6): 562-5.

Clements-Mann, M. L., Weinhold, K., Matthews, T. J., Graham, B. S., Gorse, G. J., Keefer, M. C., McElrath, M. J., Hsieh, R. H., Mestecky, J., Zolla-Pazner, S., Mascola, J., Schwartz, D., Siliciano, R., Corey, L., Wright, P. F., Belshe, R., Dolin, R., Jackson, S., Xu, S., Fast, P., Walker, M. C., Stablein, D., Excler, J. L., Tartaglia, J., and Paoletti, E. (1998) "Immune responses to human immunodeficiency virus (HIV) type 1 induced by canarypox expressing HIV-1MN gp120, HIV-1SF2 recombinant gp120, or both vaccines in seronegative adults" J. Infect Dis. 177(5): 1230-46.

Egan, M. A., Pavlat, W. A., Tartaglia, J., Paoletti, E., Weinhold, K. J., Clements, M. L., and Siliciano, R. F. (1995) "Induction of human immunodeficiency virus type 1 (HIV-1)-specific cytolytic T lymphocyte responses in seronegative adults by a nonreplicating, host-range-restricted canarypox vector (ALVAC) carrying the HIV-1MN env gene" J Infect Dis. 171(6): 1623-7.

Hel, Z., Tsai, W. P., Thornton, A., Nacsa, J., Giuliani, L., Tryniszewska, E., Poudyal, M., Venzon, D., Wang, X., Altman, J., Watkins, D. I., Lu, W., von Gegerfelt, A., Felber, B. K., Tartaglia, J., Pavlakis, G. N., and Franchini, G. (2001) "Potentiation of simian immunodeficiency virus (SIV)-specific CD4(+) and CD8(+) T cell responses by a DNA-SIV and NYVAC-SIV prime/boost regimen" J Immunol. 167(12): 7180-91.

Palmer, K. E., Thomson, J. A., and Rybicki, E. P. (1999) "Generation of maize cell lines containing autonomously replicating maize streak virus-based gene vectors" Arch Virol. 144(7): 1345-60.

Adler, S., Reay, P., Roy, P., and Klenk, H. D. (1998) "Induction of T cell response by bluetongue virus core-like particles expressing a T cell epitope of the M1 protein of influenza A virus" Med. Microbiol. Immunol (Berl). 187 (2): 91-6.

Shata, M. T., Stevceva, L., Agwale, S., Lewis, G. K., and Hone, D. M. (2000) "Recent advances with recombinant bacterial vaccine vectors" Mol Med Today 6(2): 66-71.

Tacket, C. O., Hone, D. M., Losonsky, G. A., Guers, L., Edelman, R., and Levine, M. M. (1992) "Clinical acceptability and immunogenicity of CVD 908 *Salmonella typhi* vaccine strain" Vaccine 10(7): 443-6.

Tacket, C. O., Sztein, M. B., Losonsky, G. A., Wasserman, S. S., Nataro, J. P., Edelman, R., Pickard, D., Dougan, G., Chatfield, S. N., and Levine, M. M. (1997) "Safety of live oral *Salmonella typhi* vaccine strains with deletions in htrA and aroC aroD and immune response in humans" Infect Immun. 65(2): 452-6.

Pasetti, M. F., Anderson, R. J., Noriega, F. R., Levine, M. M., and Sztein, M. B. (1999) "Attenuated deltaguaBA *Salmonella typhi* vaccine strain CVD 915 as a live vector utilizing prokaryotic or eukaryotic expression systems to deliver foreign antigens and elicit immune responses" Clin Immunol. 92(1): 76-89.

Kotloff, K. L., Noriega, F. R., Samandari, T., Sztein, M. B., Losonsky, G. A., Nataro, J. P., Picking, W. D., Barry, E. M., and Levine, M. M. (2000) "*Shigella flexneri* 2a strain CVD 1207, with specific deletions in virG, sen, set, and guaBA, is highly attenuated in humans" Infect Immun. 68(3): 1034-9.

Smith, D. B., and Johnson, K. S. (1988) "Single-step purification of polypeptides expressed in *Escherichia coli* as fusions with glutathione S-transferase" Gene 67(1): 31-40.

Abath, F. G., and Simpson, A. J. (1990) "A simple method for the recovery of purified recombinant peptides cleaved from glutathione-S-transferase-fusion proteins" Pept Res. 3(4): 167-8.

Brake, A. J., Merryweather, J. P., Coit, D. G., Heberlein, U. A., Masiarz, F. R., Mullenbach, G. T., Urdea, M. S., Valenzuela, P., and Barr, P. J. (1984) "Alpha-factor-directed synthesis and secretion of mature foreign proteins in *Saccharomyces cerevisiae*" Proc Natl Acad Sci USA. 81(15): 4642-6.

Boyer, J. D., Chattergoon, M., Muthumani, K., Kudchodkar, S., Kim, J., Bagarazzi, M., Pavlakis, G., Sekaly, R., and Weiner, D. B. (2002) "Next generation DNA vaccines for HIV-1" J. Liposome Res. 12(1-2): 137-42.

Barouch, D. H., Santra, S., Schmitz, J. E., Kuroda, M. J., Fu, T. M., Wagner, W., Bilska, M., Craiu, A., Zheng, X. X., Krivulka, G. R., Beaudry, K., Lifton, M. A., Nickerson, C. E., Trigona, W. L., Punt, K., Freed, D. C., Guan, L., Dubey, S., Casimiro, D., Simon, A., Davies, M. E., Chastain, M., Strom, T. B., Gelman, R. S., Montefiori, D. C., Lewis, M. G., Emini, E. A., Shiver, J. W., and Letvin, N. L. (2000) "Control of viremia and prevention of clinical AIDS in rhesus monkeys by cytokine-augmented DNA vaccination" Science 290(5491): 486-92.

Voller, A. *New Trends and Developments in Vaccines*, (1978) University Park Press, Baltimore, Md.

Remington, J. P. *Remington's Pharmaceutical Sciences*, 17th Edition, (1985) Mack Publishing Company, Easton, Pa.

Watanabe, M., Naito, M., Sasaki, E., Sakurai, M., Kuwana, T., and Oishi, T. (1994) "Liposome-mediated DNA transfer into chicken primordial germ cells in vivo" Mol Reprod Dev. 38(3): 268-74.

Robinson, H. L., Hunt, L. A., and Webster, R. G. (1993) "Protection against a lethal influenza virus challenge by immunization with a hemagglutinin-expressing plasmid DNA" Vaccine 11(9): 957-60.

Hoffman, S. L., Sedegah, M., and Hedstrom, R. C. (1994) "Protection against malaria by immunization with a *Plasmodium yoelii* circumsporozoite protein nucleic acid vaccine" Vaccine 12(16): 1529-33.

Xiang, Z. Q., Spitalnik, S., Tran, M., Wunner, W. H., Cheng, J., and Ertl, H. C. (1994) "Vaccination with a plasmid vector carrying the rabies virus glycoprotein gene induces protective immunity against rabies virus" Virology 199(1): 132-40.

Webster, R. G., Fynan, E. F., Santoro, J. C., and Robinson, H. (1994) "Protection of ferrets against influenza challenge with a DNA vaccine to the hemagglutinin" Vaccine 12(16): 1495-8.

Davis, H. L., Michel, M. L., Mancini, M., Schleef, M., and Whalen, R. G. (1994) "Direct gene transfer in skeletal muscle: plasmid DNA-based immunization against the hepatitis B virus surface antigen" Vaccine 12(16): 1503-9.

Davis, H. L., Michel, M. L., and Whalen, R. G. (1993) "DNA-based immunization induces continuous secretion of hepatitis B surface antigen and high levels of circulating antibody" Hum. Mol. Genet. 2(11): 1847-51.

Johnston, S. A., and Tang, D. C. (1994) "Gene gun transfection of animal cells and genetic immunization" Methods Cell Biol. 43 Pt A: 353-65.

Kozak, M. (1987) "An analysis of 5'-noncoding sequences from 699 vertebrate messenger RNAs" Nucleic Acids Res. 15(20): 8125-48.

Sambrook, J., and Russell, D. W. *Molecular Cloning: A Laboratory Manual*, (1989) 2nd Edition, Cold Spring Harbor Laboratory Press, Cold Spring Harbor, N.Y.

Williams, S. G., Cranenburgh, R. M., Weiss, A. M., Wrighton, C. J., Sherratt, D. J., Hanak, J. A. (1998) "Repressor titration: a novel system for selection and stable maintenance of recombinant plasmids" Nucleic Acids Res. 26(9): 2120-4.

Whittle, N., Adair, J., Lloyd, C., Jenkins, L., Devine, J., Schlom, J., Raubitschek, A., Colcher, D., and Bodmer, M. (1987) "Expression in COS cells of a mouse-human chimeric B72.3 antibody" Protein Eng. 1(6): 499-505.

Goodwin, E. C., and Rottman, F. M. (1992) "The 3'-flanking sequence of the bovine growth hormone gene contains novel elements required for efficient and accurate polyadenylation" J. Biol. Chem. 267(23): 16330-4.

Hanke, T., Blanchard, T. J., Schneider, J., Ogg, G. S., Tan, R., Becker, M., Gilbert, S. C., Hill, A. V., Smith, G. L., and McMichael, A. (1998c) "Immunogenicities of intravenous and intramuscular administrations of modified vaccinia virus Ankara-based multi-CTL epitope vaccine for human immunodeficiency virus type 1 in mice" J. Gen. Virol. 79 (Pt 1): 83-90.

Meyer, H., Sutter, G., and Mayr, A. (1991) "Mapping of deletions in the genome of the highly attenuated vaccinia virus MVA and their influence on virulence" J. Gen. Virol. 72 (Pt 5): 1031-8.

Altenburger, W., Suter, C. P., and Altenburger, J. (1989) "Partial deletion of the human host range gene in the attenuated vaccinia virus MVA" Arch. Virol. 105(1-2): 15-27.

Broach, J. R., Strathern, J. N., and Hicks, J. B. (1979) "Transformation in yeast: development of a hybrid cloning vector and isolation of the CAN1 gene" Gene 8(1): 121-33.

Richardson, C. D. *Baculovirus Expression Protocols: Methods in Molecular Biology, Volume* 39 (1995), Humana Press, Totowa, N.J.

Chuang, T. H., Lee, J., Kline, L., Mathison, J. C., and Ulevitch, R. J. (2002) "Toll-like receptor 9 mediates CpG-DNA signaling" J. Leukoc. Biol. 71(3): 538-44.

Ahmad-Nejad, P., Hacker, H., Rutz, M., Bauer, S., Vabulas, R. M., and Wagner, H. (2002) "Bacterial CpG-DNA and lipopolysaccharides activate Toll-like receptors at distinct cellular compartments" Eur. J. Immunol. 32(7): 1958-68.

Schellack, C., Egyed, A., Fritz, J., Brunner, S., Schmidt, W., Buschle, M., Lingnau, K. (2003) "IC31, a novel adjuvant, induces potent cellular and humoral immunity" Proceedings of the 34th Annual Meeting of the German Society of Immunology, Berlin, September 24-27.

Lingnau, K., Egyed, A., Schellack, C., Mattner, F., Buschle, M., and Schmidt, W. (2002) "Poly-L-arginine synergizes with oligodeoxynucleotides containing CpG-motifs (CpG-ODN) for enhanced and prolonged immune responses and prevents the CpG-ODN-induced systemic release of proinflammatory cytokines" Vaccine 20(29-30): 3498-508.

McSorley, S. J., Ehst, B. D., Yu, Y., and Gewirtz, A. T. (2002) Bacterial flagellin is an effective adjuvant for CD4+ T cells in vivo" J. Immunol. 169(7): 3914-9.

Veazey, R. S., Klasse, P. J., Ketas, T. J., Reeves, J. D., Piatak, M. Jr, Kunstman, K., Kuhmann, S. E., Marx, P. A., Lifson, J. D., Dufour, J., Mefford, M., Pandrea, I., Wolinsky, S. M., Doms, R. W., DeMartino, J. A., Siciliano, S. J., Lyons, K., Springer, M. S., and Moore, J. P. (2003) "Use of a small molecule CCR5 inhibitor in macaques to treat simian immunodeficiency virus infection or prevent simian-human immunodeficiency virus infection" J. Exp. Med. 198 (10): 1551-62.

Mowat, A. M., Donachie, A. M., Jagewall, S., Schon, K., Lowenadler, B., Dalsgaard, K., Kaastrup, P., and Lycke, N. (2001) "CTA1-DD-immune stimulating complexes: a novel, rationally designed combined mucosal vaccine adjuvant effective with nanogram doses of antigen" J Immunol. 167(6): 3398-405.

Allcock, H. R. (1998) "The synthesis of functional polyphosphazenes and their surfaces" Appl. Organometallic Chem. 12(10-11): 659-666.

Payne, L. G., Jenkins, S. A., Andrianov, A., and Roberts, B. E. (1995) "Water-soluble phosphazene polymers for parenteral and mucosal vaccine delivery" Pharm Biotechnol. 6: 473-93.

Green, T. D., Montefiori, D. C., and Ross, T. M. (2003) "Enhancement of antibodies to the human immunodeficiency virus type 1 envelope by using the molecular adjuvant C3d" J. Virol. 77(3): 2046-55.

Haigwood, N. L. and Stamatatos, L. (2003) "Role of neutralizing antibodies in HIV infection" AIDS 17 (Suppl 4): S67-71

Carmon, L., Bobilev-Priel, I., Brenner, B., Bobilev, D., Paz, A., Bar-Haim, E., Tirosh, B., Klein, T., Fidkin, M., Lemonnier, F., Tzehoval, E., Eisenbach, L. (2002) Characterization of novel breast carcinoma-associated BA46-derived peptides in HLA-A2.1/D(b)-beta2m transgenic mice. Clin Invest 110:453-462.

Pascolo, S., Bervas, N., Ure, J. M., Smith, A. G., Lemonnier, F. A., Perarnau, B. (1997) HLA-A2.1-restricted education and cytolytic activity of CD8(+) T lymphocytes from beta2 microglobulin (beta2m) HLA-A2.1 monochain transgenic H-2Db beta2m double knockout mice. J Exp Med. 185 (12): 2043-51.

Tourdot, S., Scardino, A., Saloustro, E., Gross, D. A., Pascolo, S., Cordopatis, P., Lemonnier, F. A., Kosmatopoulos, K., (2000) A general strategy to enhance immunogenicity of low-affinity HLA-A2.1-associated peptides: implication in the identification of cryptic tumor epitopes. Eur J Immunol. (12): 3411-21.

Thomson, M. M., Perez-Alvarez, L., and Najera, R. (2002) "Molecular epidemiology of HIV-1 genetic forms and its significance for vaccine development and therapy" Lancet Infect Dis. 2(8): 461-71.

Cao, H., Kanki, P., Sankale, J. L., Dieng-Sarr, A., Mazzara, G. P., Kalams, S. A., Korber, B., Mboup, S., and Walker, B. D. (1997) "Cytotoxic T-lymphocyte cross-reactivity among different human immunodeficiency virus type 1 clades: implications for vaccine development" J. Virol. 71(11): 8615-23.

Ferrari, G., Berend, C., Ottinger, J., Dodge, R., Bartlett, J., Toso, J., Moody, D., Tartaglia, J., Cox, W. I., Paoletti, E., and Weinhold, K. J. (1997) "Replication-defective canarypox (ALVAC) vectors effectively activate anti-human immunodeficiency virus-1 cytotoxic T lymphocytes present in infected patients: implications for antigen-specific immunotherapy" Blood 90(6): 2406-16.

Walker, B. D., and Korber, B. T. (2001) "Immune control of HIV: the obstacles of HLA and viral diversity" Nat Immunol. 2(6): 473-5.

Burrows, S. R., Rodda, S. J., Suhrbier, A., Geysen, H. M., and Moss, D. J. (1992) "The specificity of recognition of a cytotoxic T lymphocyte epitope" Eur J Immunol. 22(1): 191-5.

McMichael, A., and Hanke, T. (2002) "The quest for an AIDS vaccine: is the CD8+ T-cell approach feasible?" Nat Rev Immunol. 2(4): 283-91.

Yewdell, J. W., and Bennink, J. R. (1999) "Immunodominance in major histocompatibility complex class I-restricted T lymphocyte responses" Annu Rev Immunol. 17: 51-88.

Gallimore, A., Dumrese, T., Hengartner, H., Zinkernagel, R. M., and Rammensee, H. G. (1998) "Protective immunity does not correlate with the hierarchy of virus-specific cytotoxic T cell responses to naturally processed peptides" J Exp Med. 187(10): 1647-57.

Wilson, C. C., McKinney, D., Anders, M., MaWhinney, S., Forster, J., Crimi, C., Southwood, S., Sette, A., Chesnut, R., Newman, M. J., and Livingston, B. D. (2003) "Development of a DNA vaccine designed to induce cytotoxic T lymphocyte responses to multiple conserved epitopes in HIV-1" J. Immunol. 171(10): 5611-23.

Altschul, S. F., Gish, W., Miller, W., Myers, E. W., and Lipman, D. J. (1990) "Basic local alignment search tool" J. Mol. Biol. 215(3): 403-10.

Davison, A. J., and Moss, B. (1989) "Structure of vaccinia virus early promoters" J. Mol. Biol. 210(4): 749-69.

Taylor, J., Weinberg, R., Kawaoka, Y., Webster, R. G., and Paoletti, E. (1988) "Protective immunity against avian influenza induced by a fowlpox virus recombinant" Vaccine 6(6): 504-8.

Guo, P. X., Goebel, S., Davis, S., Perkus, M. E., Languet, B., Desmettre, P., Allen, G., and Paoletti, E. (1989) "Expression in recombinant vaccinia virus of the equine herpesvirus 1 gene encoding glycoprotein gp13 and protection of immunized animals" J. Virol. 63(10): 4189-98.

Perkus, M. E., Limbach, K., and Paoletti, E. (1989) "Cloning and expression of foreign genes in vaccinia virus, using a host range selection system" J. Virol. 63(9): 3829-36.

He, T. C., Zhou, S., da Costa, L. T., Yu, J., Kinzler, K. W., and Vogelstein, B. (1998) "A simplified system for generating recombinant adenoviruses" Proc Natl Acad Sci USA 95(5): 2509-14.

Hermeking, H., Lengauer, C., Polyak, K., He, T. C., Zhang, L., Thiagalingam, S., Kinzler, K. W., & Vogelstein, B. (1997) "14-3-3 sigma is a p53-regulated inhibitor of G2/M progression" Mol. Cell 1: 3-11.

Nakamura, N., Ramaswamy, S., Vasquez, F., Signoretti, S., Loda, M., and Sellers, W. (2000) "Forkhead transcription factors are critical effectors of cell death and cell cycle arrest downstream of PTEN" Mol. Cell Biol. 20(23): 8969-8982.

Truong, H. M. and Klausner, J. D. (2004) "Diagnostic assays for HIV-1 infection" MLO Med Lab Obs. 36(7): 12-3, 16, 18-20.

Zuber, A. K., Brave, A., Engstrom, G., Zuber, B., Ljungberg, K., Fredriksson, M., Benthin, R., Isaguliants, M. G., Sandstrom, E., Hinkula, J., and Wahren, B. (2004) "Topical delivery of imiquimod to a mouse model as a novel adjuvant for human immunodeficiency virus (HIV) DNA" Vaccine 22(13-14): 1791-8.

Beattie, T., Kaul, R., Rostron, T., Dong, T., Easterbrook, P., Jaoko, W., Kimani, J., Plummer, F., McMichael, A., and Rowland-Jones, S. (2004) "Screening for HIV-specific T-cell responses using overlapping 15-mer peptide pools or optimized epitopes" AIDS 18(11): 1595-8.

Ito, Y., Grivel, J. C., and Margolis, L. (2003) "Real-time PCR assay of individual human immunodeficiency virus type 1 variants in coinfected human lymphoid tissues" J. Clin. Microbiol. 41(5): 2126-31.

Sun, Y., Iglesias, E., Samri, A., Kamkamidze, G., Decoville, T., Carcelain, G., Autran, B. (2003) "A systematic comparison of methods to measure HIV-1 specific CD8 T cells" J. Immunol. Meth. 272(1-2): 23-34.

Shacklett, B. L. (2002) "Beyond $^{51}$Cr release: New methods for assessing HIV-1-specific CD8+ T cell responses in peripheral blood and mucosal tissues" Clin. Exp. Immunol. 130(2): 172-82.

Hsiao, C. L. and Carbon, J. (1981) "Direct selection procedure for the isolation of functional centromeric DNA". Proc Natl Acad Sci USA 78(6): 3760-4.

The invention is further described by the following numbered paragraphs:

1. An artificial fusion protein (AFP) comprising an HIV Gag domain; one or more HIV Pol domains; an HIV Vif domain; and one or more HIV Env domains.

2. The AFP of Paragraph 1, wherein each of the HIV Gag, Pol, Vif, and Env are selected so that the AFP induces an immune response to a pre-determined HIV Clade.

3. The AFP of Paragraph 2, wherein the HIV Clade is selected from the group consisting of Clade A, A1, A2, B, C and D.

4. The AFP of Paragraph 1, wherein the amino acid sequences for each of the HIV Gag, Pol, Vif, and Env domains are from an HIV consensus sequence for the same HIV Clade.

5. The AFP of Paragraph 4, wherein the HIV Clade is selected from the group consisting of Clade A, A1, A2, B, C and D.

6. The AFP of Paragraph 1, wherein the amino acid sequences for each of the HIV Gag, Pol, Vif, and Env domains are from HIV consensus sequences for different HIV Clades.

7. The AFP of Paragraph 6, wherein the HIV Clade is selected from the group consisting of Clade A, A1, A2, B, C and D.

8. The AFP of Paragraph 6, wherein the amino acid sequences for each of HIV Gag, Pol, Vif, and Env vary by from about 0% to about 10% between HIV Clades.
9. The AFP of Paragraph 8, wherein the amino acid sequences for each of HIV Gag, Pol, Vif, and Env vary by from about 0% to about 8% between HIV Clades.
10. The AFP of Paragraph 9, wherein the amino acid sequences for each of HIV Gag, Pol, Vif, and Env vary by from about 0% to about 6% between HIV Clades.
11. The AFP of Paragraph 1, wherein the domains are present from N- to C-terminus in any order that does not recreate a naturally-occurring HIV protein.
12. The AFP of Paragraph 11, wherein the domains are joined with or without intervening sequences.

13. The AFP of Paragraph 1, wherein the domains are present from N- to C-terminus in order of: HIV Gag domain, a first HIV Pol domain, HIV Vif domain, a second HIV Pol domain, a first HIV Env domain, a third HIV Pol domain, and a second HIV Env domain.

14. The AFP of Paragraph 13, wherein the domains are joined with or without intervening sequences.

15. The AFP of Paragraph 1, wherein the HIV Gag domain comprises a sequence of amino acids from an HIV isolate or an HIV consensus sequence corresponding to amino acids 1-135 of SEQ ID NO: 2.

16. The AFP of Paragraph 15, wherein the HIV Gag domain comprises amino acids 1-135 of SEQ ID NO: 2.

17. The AFP of Paragraph 1, wherein the HIV Gag domain comprises three HIV Gag subdomains.

18. The AFP of Paragraph 17, wherein each of the three HIV Gag subdomains comprise a sequence of amino acids that are from the same HIV Clade.

19. The AFP of Paragraph 17, wherein each of the three HIV Gag subdomains comprise a sequence of amino acids that are from different HIV Clades.

20. The AFP of Paragraph 17, wherein the first HIV Gag subdomain comprises a sequence of amino acids corresponding to amino acids 1-56 of SEQ ID NO: 2 and wherein the sequence is from HIV Clade C.

21. The AFP of Paragraph 17, wherein the second HIV Gag subdomain comprises a sequence of amino acids corresponding to amino acids 57-96 of SEQ ID NO: 2 and wherein the sequence is from HIV Clade D.

22. The AFP of Paragraph 17, wherein the third HIV Gag subdomain comprises a sequence of amino acids corresponding to amino acids 97-135 of SEQ ID NO: 2 and wherein the sequence is from HIV Clade A.

23. The AFP of Paragraph 1, which comprises three HIV Pol domains.

24. The AFP of Paragraph 23, wherein the first HIV Pol domain comprises a sequence of amino acids from an HIV isolate or an HIV consensus sequence corresponding to amino acids 136-393 of SEQ ID NO: 2, wherein the second HIV Pol domain comprises a sequence of amino acids from an HIV isolate or an HIV consensus sequence corresponding to amino acids 422-484 of SEQ ID NO: 2, and wherein the third HIV Pol domain comprises a sequence of amino acids from an HIV isolate or an HIV consensus sequence corresponding to amino acids 522-723 of SEQ ID NO: 2.

25. The AFP of Paragraph 24, wherein the first HIV Pol domain comprises amino acids 136-393 of SEQ ID NO: 2 and the second HIV Pol domain comprises amino acids 422-484 of SEQ ID NO: 2 and the third HIV Pol domain comprises amino acids 522-723 of SEQ ID NO: 2.

26. The AFP of Paragraph 24, wherein each HIV Pol domain comprises at least two HIV Pol subdomains.

27. The AFP of Paragraph 26, wherein each of the at least two HIV Pol subdomains comprise a sequence of amino acids that are from the same HIV Clade.

28. The AFP of Paragraph 26, wherein each of the at least two HIV Pol subdomains comprise a sequence of amino acids that are from different HIV Clades.

29. The AFP of Paragraph 26, wherein the first HIV Pol domain comprises two HIV Pol subdomains.

30. The AFP of Paragraph 29, wherein the first HIV Pol subdomain comprises a sequence of amino acids corresponding to amino acids 136-265 of SEQ ID NO: 2 and wherein the sequence is from HIV Clade B.

31. The AFP of Paragraph 29, wherein the second HIV Pol subdomain comprises a sequence of amino acids corresponding to amino acids 266-393 of SEQ ID NO: 2 and wherein the sequence is from HIV Clade C.

32. The AFP of Paragraph 26, wherein the second HIV Pol domain comprises two HIV Pol subdomains.

33. The AFP of Paragraph 32, wherein the first HIV Pol subdomain comprises a sequence of amino acids corresponding to amino acids 432-467 of SEQ ID NO: 2 and wherein the sequence is from HIV Clade A.

34. The AFP of Paragraph 32, wherein the second HIV Pol subdomain comprises a sequence of amino acids corresponding to amino acids 468-494 of SEQ ID NO: 2 and wherein the sequence is from HIV Clade B.

35. The AFP of Paragraph 26, wherein the third HIV Pol domain comprises four HIV Pol subdomains.

36. The AFP of Paragraph 35, wherein the first HIV Pol subdomain comprises a sequence of amino acids corresponding to amino acids 522-556 of SEQ ID NO: 2 and wherein the sequence is from HIV Clade D.

37. The AFP of Paragraph 35, wherein the second HIV Pol subdomain comprises a sequence of amino acids corresponding to amino acids 557-629 of SEQ ID NO: 2 and wherein the sequence is from HIV Clade A.

38. The AFP of Paragraph 35, wherein the third HIV Pol subdomain comprises a sequence of amino acids corresponding to amino acids 630-676 of SEQ ID NO: 2 and wherein the sequence is from HIV Clade B.

39. The AFP of Paragraph 35, wherein the fourth HIV Pol subdomain comprises a sequence of amino acids corresponding to amino acids 677-723 of SEQ ID NO: 2 and wherein the sequence is from HIV Clade C.

40. The AFP of Paragraph 1, wherein the HIV Vif domain comprises a sequence of amino acids from an HIV isolate or an HIV consensus sequence corresponding to amino acids 394-421 of SEQ ID NO: 2.

41. The AFP of Paragraph 40, wherein the HIV Vif domain comprises amino acids 394-421 of SEQ ID NO: 2.

42. The AFP of Paragraph 40, wherein the HIV Vif domain comprises a sequence from HIV Clade D.

43. The AFP of Paragraph 1, wherein the first Env domain comprises a sequence of amino acids from an HIV isolate or an HIV consensus sequence corresponding to amino acids 485-521 of SEQ ID NO: 2, and wherein the second HIV Env domain comprises a sequence of amino acids from an HIV isolate or an HIV consensus sequence corresponding to amino acids 724-777 of SEQ ID NO: 2.

44. The AFP of Paragraph 1, wherein the first HIV Env domain comprises amino acids 485-521 of SEQ ID NO: 2, and wherein the second HIV Env domain comprises amino acids 724-777 of SEQ ID NO: 2.

45. The AFP of Paragraph 43, wherein the first Env domain comprises a sequence from HIV Clade C.

46. The AFP of Paragraph 43, wherein the second Env domain comprises a sequence from HIV Clade D.

47. The AFP of Paragraph 1, comprising amino acids 1-777 of SEQ ID NO: 2.
48. The AFP of Paragraph 1, further comprising one or more non-human CTL domains for monitoring immune responses to the AFP in a laboratory mammal.
49. The AFP of Paragraph 48, wherein the one or more non-human CTL domains is selected from the group consisting of the SIV tat CTL epitope, the pb9 epitope, the P118-I10 epitope and the SIV Gag p27 epitope.
50. The AFP of Paragraph 49, wherein the additional domains are the SIV Gag p27 CTL epitope and the P18-I10 epitope.
51. The AFP of Paragraph 48, further comprising a marker domain.
52. The AFP of Paragraph 51, wherein the marker domain encodes an epitope for a monoclonal antibody selected from the group consisting of Pk, Flag, HA, myc, GST or His epitopes.
53. The AFP of Paragraph 52, wherein the marker domain encodes the Pk epitope.
54. The AFP of Paragraph 1, comprising amino acids 1-806 of SEQ ID NO: 2.
55. An isolated nucleic acid having a nucleotide sequence encoding the AFP of any one of Paragraphs 1-47.
56. An isolated nucleic acid having a nucleotide sequence encoding the AFP of Paragraph 50.
57. An isolated nucleic acid having a nucleotide sequence encoding the AFP of Paragraph 53.
58. An isolated nucleic acid having a nucleotide sequence encoding the AFP of Paragraph 55.
59. An isolated nucleic acid, wherein the nucleic acid has a nucleotide sequence comprising SEQ ID NO: 1.
60. An expression vector comprising a nucleic acid having a nucleotide sequence encoding the AFP of any one of Paragraphs 1-47 operably linked to at least one nucleic acid control sequence.
61. An expression vector comprising a nucleic acid having a nucleotide sequence encoding the AFP of Paragraph 50 operably linked to at least one nucleic acid control sequence.
62. An expression vector comprising a nucleic acid having a nucleotide sequence encoding the AFP of Paragraph 53 operably linked to at least one nucleic acid control sequence.
63. An expression vector comprising a nucleic acid having a nucleotide sequence encoding the AFP of Paragraph 55 operably linked to at least one nucleic acid control sequence.
64. The expression vector of Paragraph 60, wherein the vector is a plasmid vector, a viral vector, an insect vector, a yeast vector or a bacterial vector.
65. The expression vector of Paragraph 64, wherein the plasmid vector is pTH or pTHr.
66. The expression vector of Paragraph 64, wherein the viral vector is an alphavirus replicon vector, an adeno-associated virus vector, an adenovirus vector, a retrovirus vector or a poxvirus vector.
67. The expression vector of Paragraph 66, wherein the vector is a poxvirus vector selected from the group consisting of vaccinia virus and avipox virus.
68. The expression vector of Paragraph 66, wherein the poxvirus is an attenuated poxvirus selected from the group consisting of modified vaccinia Ankara (MVA), NYVAC, TROVAC, and ALVAC.
69. The expression vector of Paragraph 64, wherein the bacterial vector is a live, attenuated *Salmonella* or a *Shigella* vector.
70. The expression vector of Paragraph 60, wherein the nucleic acid control sequence is a cytomegalovirus (CMV) immediate early promoter.
71. The expression vector of any one of Paragraphs 60-68, wherein the codons encoding the AFP are those of highly expressed genes for a target subject or host cell in which the AFP is to be expressed.
72. The expression vector of Paragraph 71, wherein the target subject or host cell is a human.
73. The expression vector of Paragraph 65, wherein the expression vector and nucleic acid together is pTHr.HIV-CON.
74. The expression vector of Paragraph 68, wherein the expression vector and nucleic acid together is MVA.HIV-CON.
75. A host cell comprising the expression vector of Paragraph 60.
76. A host cell comprising the expression vector of Paragraph 61.
77. A host cell comprising the expression vector of Paragraph 62.
78. A host cell comprising the expression vector of Paragraph 63.
79. A host cell comprising the expression vector of Paragraph 71.
80. A host cell comprising the expression vector of Paragraph 72.
81. A host cell comprising the expression vector of Paragraph 73.
82. A method of preparing an AFP, which comprises (a) culturing the host cell of any one of Paragraphs 75-81 for a time and under conditions to express the AFP; and (b) recovering the AFP.
83. A method for introducing into and expressing an AFP in an animal, which comprises delivering an expression vector of Paragraph 60 into the animal and thereby obtaining expression of the AFP in the animal.
84. A method for introducing into and expressing an AFP in an animal, which comprises delivering an expression vector of Paragraph 61 into the animal and thereby obtaining expression of the AFP in the animal.
85. A method for introducing into and expressing an AFP in an animal, which comprises delivering an expression vector of Paragraph 62 into the animal and thereby obtaining expression of the AFP in the animal.
86. A method for introducing into and expressing an AFP in an animal, which comprises delivering an expression vector of any one of Paragraphs 63-70, 73, or 74 into the animal and thereby obtaining expression of the AFP in the animal.
87. A method for expressing an AFP in animal cells, which comprises (a) introducing an expression vector of Paragraph 60 into the animal cells; and (b) culturing those cells under conditions sufficient to express the AFP.
88. A method for expressing an AFP in animal cells, which comprises (a) introducing an expression vector of Paragraph 61 into the animal cells; and (b) culturing those cells under conditions sufficient to express the AFP.
89. A method for expressing an AFP in animal cells, which comprises (a) introducing an expression vector of Paragraph 62 into the animal cells; and (b) culturing those cells under conditions sufficient to express the AFP.
90. A method for expressing an AFP in animal cells, which comprises (a) introducing an expression vector of Paragraph 63-70, 73 or 74 into the animal cells; and (b) culturing those cells under conditions sufficient to express the AFP.
91. A method for inducing an immune response in an animal, which comprises delivering an expression vector of Paragraph 60 into the animal, wherein the AFP is expressed at a level sufficient to induce an immune response to the AFP.

92. A method for inducing an immune response in an animal, which comprises delivering an expression vector of Paragraph 61 into the animal, wherein the AFP is expressed at a level sufficient to induce an immune response to the AFP.
93. A method for inducing an immune response in an animal, which comprises delivering an expression vector of Paragraph 62 into the animal, wherein the AFP is expressed at a level sufficient to induce an immune response to the AFP.
94. A method for inducing an immune response in an animal, which comprises delivering an expression vector of any one of Paragraphs 63-70, 73 or 74 into the animal, wherein the AFP is expressed at a level sufficient to induce an immune response to the AFP.
95. A method for inducing an immune response in an animal, which comprises delivering an AFP of any one of Paragraphs 1-47 into the animal in an amount sufficient to induce an immune response to the AFP.
96. A method for inducing an immune response in an animal, which comprises delivering an AFP of Paragraph 48 into the animal in an amount sufficient to induce an immune response to the AFP.
97. A method for inducing an immune response in an animal, which comprises delivering an AFP of Paragraph 51 into the animal in an amount sufficient to induce an immune response to the AFP.
98. A method for inducing an immune response in an animal, which comprises delivering an AFP of Paragraph 54 into the animal in an amount sufficient to induce an immune response to the AFP.
99. A method of inducing an immune response against HIV in a human subject, which comprises administering an immunogen one or more times to a subject, wherein the immunogen is selected from the group consisting of (i) an AFP of any one of Paragraphs 1-47 or 54, (ii) a nucleic acid encoding the AFP, and (iii) an expression vector encoding the AFP; and wherein the AFP is administered in an amount or expressed at a level sufficient to induce an HIV-specific CTL immune response in the subject.
100. The method of Paragraph 99, wherein the subject receives at least two administrations of the immunogen at intervals of at least two weeks or at least four weeks.
101. The method of Paragraph 100, wherein another HIV immunogen is administered at the same time or at different times as part of an overall immunization regime.
102. A method of inducing an immune response against HIV in a human subject, which comprises administering to the subject at least one priming dose of an HIV immunogen and at least one boosting dose of an HIV immunogen, wherein the immunogen in each dose can be the same or different, provided that at least one of the immunogens is an AFP of any one of Paragraphs 1-47 or 54 or is a nucleic acid or an expression vector encoding the AFP, wherein the immunogens are administered in an amount or expressed at a level sufficient to induce an HIV-specific T-cell immune response in the subject.
103. The method of Paragraph 102, wherein the interval between each dose is at least two weeks or at least four weeks.
104. The method of Paragraph 102, wherein pTHr.HIVCON is administered one or more times as a priming dose.
105. The method of Paragraph 102, wherein MVA.HIVCON is administered one or more times as a boosting dose.
106. The method of Paragraph 104, wherein MVA.HIVCON is administered one or more times as a boosting dose.
107. The method of Paragraph 102, which comprises administering two priming doses and administering two boosting doses, wherein the immunogen used for the priming doses is a plasmid vector and the immunogen used for the boosting doses is a viral vector.
108. The method of Paragraph 104, wherein the viral vector is an MVA vector.
109. The method of Paragraph 107, wherein each of the priming doses is a mixture of vectors selected from the group consisting of pTHr.HIVA, pTHr.RENTA, and pTHr.HIVCON and each of the boosting doses is a mixture of vectors selected from the group consisting of MVA.RENTA, MVA.HIVA, and MVA.HIVCON.
110. An immunogenic composition comprising an AFP of any one of Paragraphs 1-47 or 54, or a nucleic acid encoding the AFP, or an expression vector encoding the AFP; and a pharmaceutically acceptable carrier.
111. An immunogenic composition comprising an AFP of Paragraph 48, or a nucleic acid encoding the AFP, or an expression vector encoding the AFP; and a pharmaceutically acceptable carrier.
112. An immunogenic composition comprising an AFP of Paragraph 51, or a nucleic acid encoding the AFP, or an expression vector encoding the AFP; and a pharmaceutically acceptable carrier.
113. An immunogenic composition comprising an expression vector of any one of Paragraphs 63-70, 73 or 74; and a pharmaceutically acceptable carrier.
114. The composition of Paragraph 110, which further comprises an adjuvant.
115. The composition of Paragraph 111, which further comprises an adjuvant.
116. The composition of Paragraph 112, which further comprises an adjuvant.
117. The composition of Paragraph 113, which further comprises an adjuvant.
118. The composition of any of Paragraphs 114-117, wherein the adjuvant is selected from the group consisting of mineral salts, polynucleotides, polyarginines, ISCOMs, saponins, monophosphoryl lipid A, imiquimod, CCR-5 inhibitors, toxins, polyphosphazenes, cytokines, immunoregulatory proteins, immunostimulatory fusion proteins, co-stimulatory molecules, and combinations thereof.
119. A library of immunogenic polypeptides, comprising a plurality of polypeptides comprising at least 15 successive amino acids of SEQ ID NO: 2, wherein each immunogenic polypeptide corresponds to at least a portion or a fragment of SEQ ID NO: 2.
120. The library of Paragraph 119, wherein the plurality of immunogenic polypeptides correspond in total to the entire length of SEQ ID NO: 2.
121. The library of Paragraph 119, wherein each polypeptide comprises overlapping amino acid sequences.
122. The library of Paragraph 121, wherein the sequences overlap by at least eleven amino acids.
123. A method of identifying a CTL epitope against HIV from the library of Paragraph 119 in a cell expressing MHC Class I protein, comprising the steps of:
a. Contacting the cell with the library of Paragraph 119;
b. Selectively binding the library with the MHC protein of the cell;
c. Isolating a polypeptide of the library that selectively binds to MHC, and;
d. Sequencing the polypeptide, thereby identifying the CTL epitope.
124. The method of Paragraph 123, wherein the cell is an antigen-presenting cell.

125. The method of Paragraph 124, wherein the cell is a splenocyte.

126. The method of Paragraph 123, wherein the cell is a human cell.

127. The method of Paragraph 126, wherein the MHC Class I protein is human leukocyte antigen (HLA).

128. The method of Paragraph 123, wherein selective binding is measured by flow cytometry.

129. The method of Paragraph 123, wherein the polypeptide is isolated by chromatography.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A HIVCON immunogen comprising the amino acid sequence of SEQ ID NO: 2.

2. A HIVCON immunogen comprising the amino acid sequence of SEQ ID NO: 4.

* * * * *